(12) United States Patent
Liao et al.

(10) Patent No.: US 10,476,006 B2
(45) Date of Patent: Nov. 12, 2019

(54) COMPOUND AND ORGANIC ELECTRONIC DEVICE USING THE SAME

(71) Applicant: NICHEM FINE TECHNOLOGY CO., LTD., Jhubei, Hsinchu County (TW)

(72) Inventors: Liang-Di Liao, Jhubei (TW); Hui-Ling Wu, Jhubei (TW); Shwu-Ju Shieh, Jhubei (TW); Chi-Chung Chen, Jhubei (TW)

(73) Assignee: SHANGHAI NICHEM FINE CHEMICAL CO., LTD., Shanghai (CN)

( * ) Notice: Subject to any disclaimer, the term of this patent is extended or adjusted under 35 U.S.C. 154(b) by 197 days.

(21) Appl. No.: 15/670,479

(22) Filed: Aug. 7, 2017

(65) Prior Publication Data
US 2018/0047908 A1 Feb. 15, 2018

Related U.S. Application Data

(60) Provisional application No. 62/528,230, filed on Jul. 3, 2017, provisional application No. 62/372,417, filed on Aug. 9, 2016.

(51) Int. Cl.
*H01L 51/00* (2006.01)
*C07B 59/00* (2006.01)
(Continued)

(52) U.S. Cl.
CPC ........ *H01L 51/0057* (2013.01); *C07B 59/002* (2013.01); *C07C 255/50* (2013.01);
(Continued)

(58) Field of Classification Search
CPC ............ C07C 2603/97; C07C 2603/98; H01L 51/0057
See application file for complete search history.

(56) References Cited

FOREIGN PATENT DOCUMENTS

CN 103833507 A 6/2014
CN 103833790 A 6/2014
(Continued)

OTHER PUBLICATIONS

Computer-generated English-language translation of CN103833507A.*
(Continued)

*Primary Examiner* — Vu A Nguyen
(74) *Attorney, Agent, or Firm* — Birch, Stewart, Kolasch & Birch, LLP

(57) ABSTRACT

Provided are a novel compound and an organic electronic device using the same. The novel compound is represented by the following Formula (I):

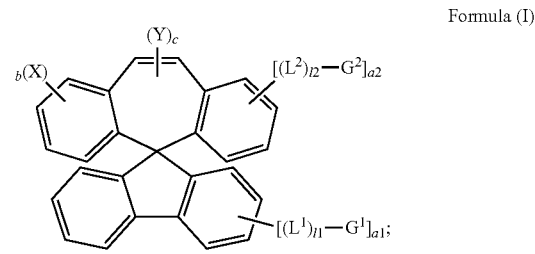

Formula (I)

Wherein,
a1 and a2 are each independently an integral from 0 to 4; the total of a1 and a2 is not less than 1;
l1 and l2 are each independently an integral from 0 to 3;
$L^1$ and $L^2$ are each independently a substituted or unsubstituted arylene group having 6 to 60 carbon atoms;
b is an integral of 0 to 4;
c is an integral of 0 to 2.

14 Claims, 26 Drawing Sheets

| Cathode | —18 |
| EIL | —17 |
| ETL | —16 |
| EL | —15 |
| HTL | —14 |
| HIL | —13 |
| Anode | —12 |
| Substrate | —11 |

(51) Int. Cl.
| | | |
|---|---|---|
| | *C07D 239/26* | (2006.01) |
| | *C07D 251/24* | (2006.01) |
| | *C07C 255/50* | (2006.01) |
| | *C07C 255/51* | (2006.01) |
| | *C07D 239/74* | (2006.01) |
| | *C07D 401/04* | (2006.01) |
| | *C07D 401/10* | (2006.01) |
| | *C07D 403/04* | (2006.01) |
| | *C07D 235/18* | (2006.01) |
| | *C09K 11/06* | (2006.01) |
| | *H01L 51/50* | (2006.01) |
| | *H01L 51/52* | (2006.01) |

(52) U.S. Cl.
CPC .......... *C07C 255/51* (2013.01); *C07D 235/18* (2013.01); *C07D 239/26* (2013.01); *C07D 239/74* (2013.01); *C07D 251/24* (2013.01); *C07D 401/04* (2013.01); *C07D 401/10* (2013.01); *C07D 403/04* (2013.01); *C09K 11/06* (2013.01); *H01L 51/006* (2013.01); *H01L 51/0052* (2013.01); *H01L 51/0058* (2013.01); *H01L 51/0067* (2013.01); *H01L 51/0072* (2013.01); *C07B 2200/05* (2013.01); *C07C 2603/94* (2017.05); *C09K 2211/1007* (2013.01); *C09K 2211/1011* (2013.01); *C09K 2211/1029* (2013.01); *C09K 2211/1044* (2013.01); *C09K 2211/1059* (2013.01); *H01L 51/001* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5206* (2013.01); *H01L 51/5221* (2013.01)

(56) References Cited

FOREIGN PATENT DOCUMENTS

| | | |
|---|---|---|
| CN | 103936720 A | 7/2014 |
| CN | 103833507 B * | 8/2016 |
| JP | 2010024149 A * | 2/2010 |
| JP | 2010-24149 A | 6/2014 |
| KR | 10-2012-0093076 A | 8/2012 |
| WO | WO 2016/102414 A1 | 6/2016 |

OTHER PUBLICATIONS

SciFinder Search Results, Apr. 12, 2019.*
Extended European Search Report issued in European Application No. 17185262.7 dated Nov. 27, 2017.
Korean Office Action issued in Korean Application No. 10-2017-0100469 dated Jan. 22, 2018, together with an English translation.

* cited by examiner

COMPOUND AND ORGANIC ELECTRONIC DEVICE USING THE SAME

CROSS-REFERENCE TO RELATED APPLICATION

Pursuant to 35 U.S.C. § 119(e), this application claims the benefits of the priority to U.S. Provisional Patent Application No. 62/372,417, filed Aug. 9, 2016 and the priority to U.S. Provisional Patent Application No. 62/528,230, filed Jul. 3, 2017. The contents of the prior applications are incorporated herein by its entirety.

BACKGROUND OF THE INVENTION

1. Field of the Invention

The present invention relates to a novel compound and an organic electronic device using the same, more particularly to a novel compound as electron transport layer and an organic electronic device using the same.

2. Description of the Prior Arts

With the advance of technology, various organic electronic devices that make use of organic materials have been energetically developed. Examples of organic electronic devices include organic light emitting devices (OLEDs), organic phototransistors, organic photovoltaic cells, and organic photodetectors.

OLED was initially invented and proposed by Eastman Kodak Company through a vacuum evaporation method. Dr. Ching M. Tang and Steven Van Slyke of Kodak Company deposited an electron transport material such as tris(8-hydroxyquinoline)aluminum(III) (abbreviated as $Alq_3$) on a transparent indium tin oxide glass (abbreviated as ITO glass) formed with a hole transport layer of organic aromatic diamine thereon, and subsequently deposited a metal electrode onto an electron transport layer to complete the fabrication of the OLED. OLEDs have attracted lots of attention due to their numerous advantages, such as fast response speed, light weight, compactness, wide viewing angle, high brightness, higher contrast ratio, no need of backlight, and low power consumption. However, the OLEDs still have the problems such as low efficiency and short lifetime.

To overcome the problem of low efficiency, one of the approaches is to interpose some interlayers between the cathode and the anode. With reference to FIG. 1, a modified OLED 1 may have a structure of a substrate 11, an anode 12, a hole injection layer 13 (abbreviated as HIL), a hole transport layer 14 (abbreviated as HTL), an emission layer 15 (abbreviated as EL), an electron transport layer 16 (abbreviated as ETL), an electron injection layer 17 (abbreviated as EIL), and a cathode 18 stacked in sequence. When a voltage is applied between the anode 12 and the cathode 18, the holes injected from the anode 12 move to the EL via HIL and HTL and the electrons injected from the cathode 18 move to the EL via EIL and ETL. Recombination of the electrons and the holes occurs in the EL to generate excitons, thereby emitting a light when the excitons decay from excited state to ground state.

Another approach is to modify the materials of ETL for OLEDs to render the electron transport materials to exhibit hole-blocking ability. Examples of conventional electron transport materials include 3,3'-[5'-[3-(3-pyridinyl)phenyl][1,1':3',1''-terphenyl]-3,3''-diyl]bispyridine (TmPyPb), 1,3,5-tris(1-phenyl-1H-benzimidazol-2-yl)benzene (TPBi), tris(2,4,6-trimethyl-3-(pyridin-3-yl)phenyl)borane (3TPYMB), 1,3-bis(3,5-dipyrid-3-yl-phenyl)benzene (BmPyPb), and 9,10-bis(3-(pyridin-3-yl)phenyl)anthracene (DPyPA).

However, even using the foresaid electron transport materials, the current efficiency of OLEDs still needs to be improved. Therefore, the present invention provides a novel compound to mitigate or obviate the problems in the prior art.

SUMMARY OF THE INVENTION

An objective of the present invention is to provide a novel compound useful for an organic electronic device.

Another objective of the present invention is to provide an organic electronic device using the novel compound, so as to improve the efficiency of the organic electronic device.

To achieve the foresaid objectives, the present invention provides a novel compound represented by the following Formula (I):

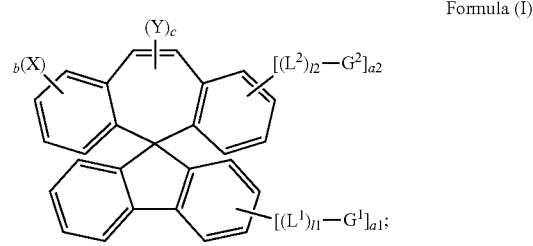

Formula (I)

Wherein, a1 and a2 are each independently an integral from 0 to 4; the total of a1 and a2 is not less than 1;

l1 and l2 are each independently an integral from 0 to 3;

$L^1$ and $L^2$ are each independently a substituted or unsubstituted arylene group having 6 to 60 carbon atoms;

$G^1$ and $G^2$ are each independently selected from the group consisting of: a heteroaryl group having 3 to 60 ring carbon atoms, an alkyl group having 1 to 40 carbon atoms and substituted with at least one functional group, an alkenyl group having 2 to 40 carbon atoms and substituted with at least one functional group, an alkynyl group having 2 to 40 carbon atoms and substituted with at least one functional group, a cycloalkyl group having 3 to 60 ring carbon atoms and substituted with at least one functional group, a heterocycloalkyl group having 3 to 60 ring carbon atoms and substituted with at least one functional group, an alkoxy group having 1 to 40 carbon atoms and substituted with at least one functional group, an aryl group having 6 to 60 ring carbon atoms and substituted with at least one functional group, an aryloxy group having 6 to 60 ring carbon atoms and substituted with at least one functional group, an alkylsilyl group having 1 to 40 carbon atoms and substituted with at least one functional group, an arylsilyl group having 6 to 60 ring carbon atoms and substituted with at least one functional group, an alkylboron group having 1 to 40 carbon atoms and substituted with at least one functional group, an arylboron group having 6 to 60 ring carbon atoms and substituted with at least one functional group, a phosphine group having 1 to 40 carbon atoms and substituted with at least one functional group, a phosphine oxide group having 1 to 40 carbon atoms and substituted with at least one functional group, any isomeric groups thereof, and any deuterated analogs thereof, wherein the functional group is selected from the group consisting of: a cyano group, a nitro group, a trifluoromethyl group, a fluoro group, and a chloro group;

b is an integral of 0 to 4;

X is selected from the group consisting of: a deuterium atom, a fluoro group, a chloro group, a bromo group, an unsubstituted aryl group having 6 to 60 carbon atoms, an unsubstituted alkyl group having 1 to 12 carbon atoms, an unsubstituted alkenyl group having 2 to 12 carbon atoms, and an unsubstituted alkynyl group having 2 to 12 carbon atoms;

c is an integral of 0 to 2;

Y is selected from the group consisting of: a deuterium atom, a substituted or unsubstituted aryl group having 6 to 60 carbon atoms, and a substituted or unsubstituted heteroaryl group having 3 to 60 carbon atoms.

The compound attached with at least one specific group $[(L^1\text{-}G^1) \text{ or } (L^2\text{-}G^2)]$ is suitable as an electron transport material for any color OLEDs, and allows the OLEDs using the same to have low driving voltage and improved current efficiency and external quantum efficiency (EQE).

Preferably, only one specific group is attached on the upper part or the lower part of the main skeletal structures. That is, in one embodiment, a1 is an integral of 1, and a2 is an integral of 0. In the other embodiment, a1 is an integral of 0, and a2 is an integral of 1.

Preferably, the specific groups $[(L^1\text{-}G^1) \text{ and } (L^2\text{-}G^2)]$ are respectively attached on the lower part and the upper part of the main skeletal structures, but there is only one specific group attached on the upper part of the main skeletal structure and only one specific group attached on the lower part of the main skeletal structure. That is, in the other embodiment, a1 and a2 both are an integral of 1.

More preferably, the compound is represented by any one of the following formulae:

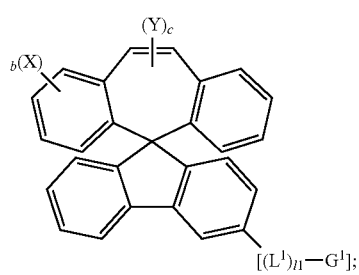

Formula (I-I)

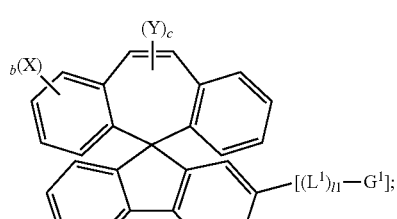

Formula (I-II)

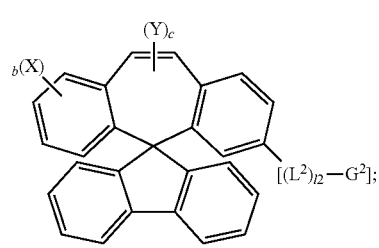

Formula (I-III)

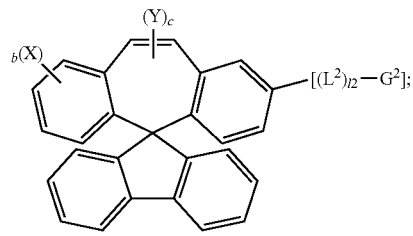

Formula (I-IV)

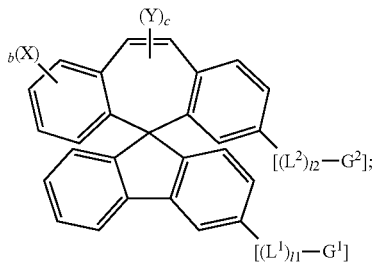

Formula (I-V)

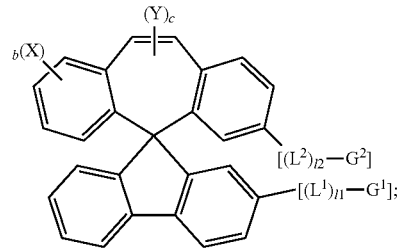

Formula (I-VI)

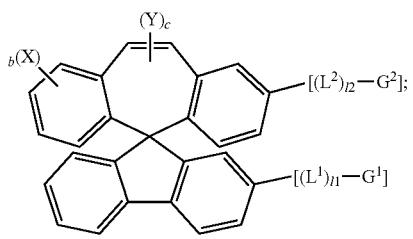

Formula (I-VII)

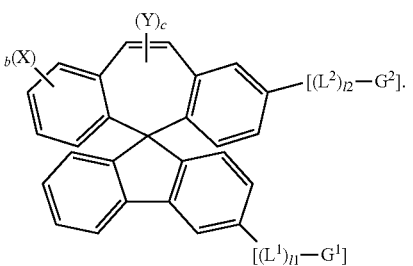

Formula (I-VIII)

Preferably, the heteroaryl groups having 3 to 60 ring carbon atoms of $G^1$ and $G^2$ are each selected from the group consisting of: a substituted or unsubstituted furyl group, a substituted or unsubstituted pyrrolyl group, a substituted or unsubstituted thiophenyl group, a substituted or unsubstituted imidazolyl group, a substituted or unsubstituted pyrazolyl group, a substituted or unsubstituted triazolyl group, a substituted or unsubstituted tetrazolyl group, a substituted or unsubstituted oxazolyl group, a substituted or unsubstituted isoxazolyl group, a substituted or unsubstituted thiazolyl group, a substituted or unsubstituted isothiazolyl group, a substituted or unsubstituted oxadiazolyl group, a substituted or unsubstituted thiadiazolyl group; a substituted or unsubstituted pyridyl group, a substituted or unsubstituted pyridazinyl group, a substituted or unsubstituted pyrimidinyl group, a substituted or unsubstituted pyrazinyl group, a substituted or unsubstituted triazinyl group; a substituted or unsubstituted indolyl group, a substituted or unsubstituted isoindolyl group, a substituted or unsubstituted benzofuranyl group, a substituted or unsubstituted isobenzofuranyl group, a substituted or unsubstituted benzothiophenyl group, a substituted or unsubstituted isobenzothiophenyl group, a substituted or unsubstituted indolizinyl group, a substituted or unsubstituted quinolizinyl group, a substituted or unsubstituted quinolyl group, a substituted or unsubstituted isoquinolyl group, a substituted or unsubstituted cinnolyl group, a substituted or unsubstituted phthalazinyl group, a substituted or unsubstituted quinazolinyl group, a substituted or unsubstituted quinoxalinyl group, a substituted or unsubstituted benzimidazolyl group, a substituted or unsubstituted benzoxazolyl group, a substituted or unsubstituted benzothiazolyl group, a substituted or unsubstituted indazolyl group, a substituted or unsubstituted benzotriazinyl group, a substituted or unsubstituted dipyridyl group, a substituted or unsubstituted benzisoxazolyl group, a substituted or unsubstituted benzisothiazolyl group; a substituted or unsubstituted dibenzofuranyl group, a substituted or unsubstituted dibenzothiophenyl group, a substituted or unsubstituted carbazolyl group, a substituted or unsubstituted biscarbazolyl group, a substituted or unsubstituted coumarinyl group, a substituted or unsubstituted chromenyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted phenothiazinyl group, a substituted or unsubstituted phenoxazinyl group, a substituted or unsubstituted azatriphenylenyl group, a substituted or unsubstituted diazatriphenylenyl group, a substituted or unsubstituted xanthenyl group, a substituted or unsubstituted azacarbazolyl group, a substituted or unsubstituted azadibenzofuranyl group, a substituted or unsubstituted azadibenzothiophenyl group, a substituted or unsubstituted benzofuranobenzothiophenyl group, a substituted or unsubstituted benzothienobenzothiophenyl group, a substituted or unsubstituted dibenzofuranonaphthyl group, a substituted or unsubstituted dibenzothienonaphthyl group, a substituted or unsubstituted dinaphthothienothiophenyl group, a substituted or unsubstituted dinaphtho carbazolyl group, a substituted or unsubstituted dibenzo[b,f]azepin group, a substituted or unsubstituted tribenzo[b,d,f]azepin group, a substituted or unsubstituted dibenzo[b,f]oxepin group, a substituted or unsubstituted tribenzo[b,d,f]oxepin group, any isomeric groups thereof, and any deuterated analogs thereof.

More preferably, $G^1$ and $G^2$ are each independently selected from the group consisting of: a substituted or unsubstituted pyridyl group, a substituted or unsubstituted pyridazinyl group, a substituted or unsubstituted pyrimidinyl group, a substituted or unsubstituted pyrazinyl group, a substituted or unsubstituted triazinyl group, a substituted or unsubstituted indolizinyl group, a substituted or unsubstituted quinolizinyl group, a substituted or unsubstituted quinolyl group, a substituted or unsubstituted isoquinolyl group, a substituted or unsubstituted phthalazinyl group, a substituted or unsubstituted quinazolinyl group, a substituted or unsubstituted quinoxalinyl group, a substituted or unsubstituted benzimidazolyl group, a substituted or unsubstituted indazolyl group, a substituted or unsubstituted benzotriazinyl group, a substituted or unsubstituted dipyridyl group, a substituted or unsubstituted pyrrolyl group, a substituted or unsubstituted imidazolyl group, a substituted or unsubstituted pyrazolyl group, a substituted or unsubstituted triazolyl group, a substituted or unsubstituted benzopyrrolyl group, a substituted or unsubstituted benzoimidazolyl group, a substituted or unsubstituted benzotriazolyl group, and any deuterated analogs thereof.

Specifically, $G^1$ and $G^2$ are each independently selected from the group consisting of:

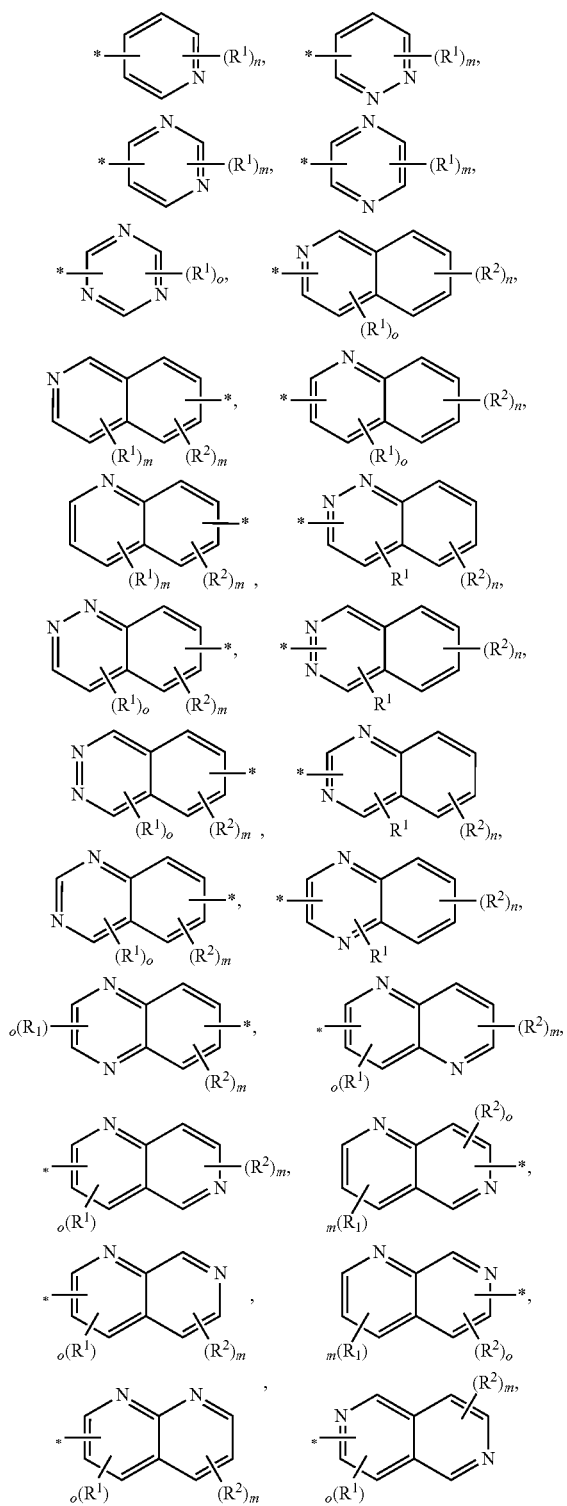

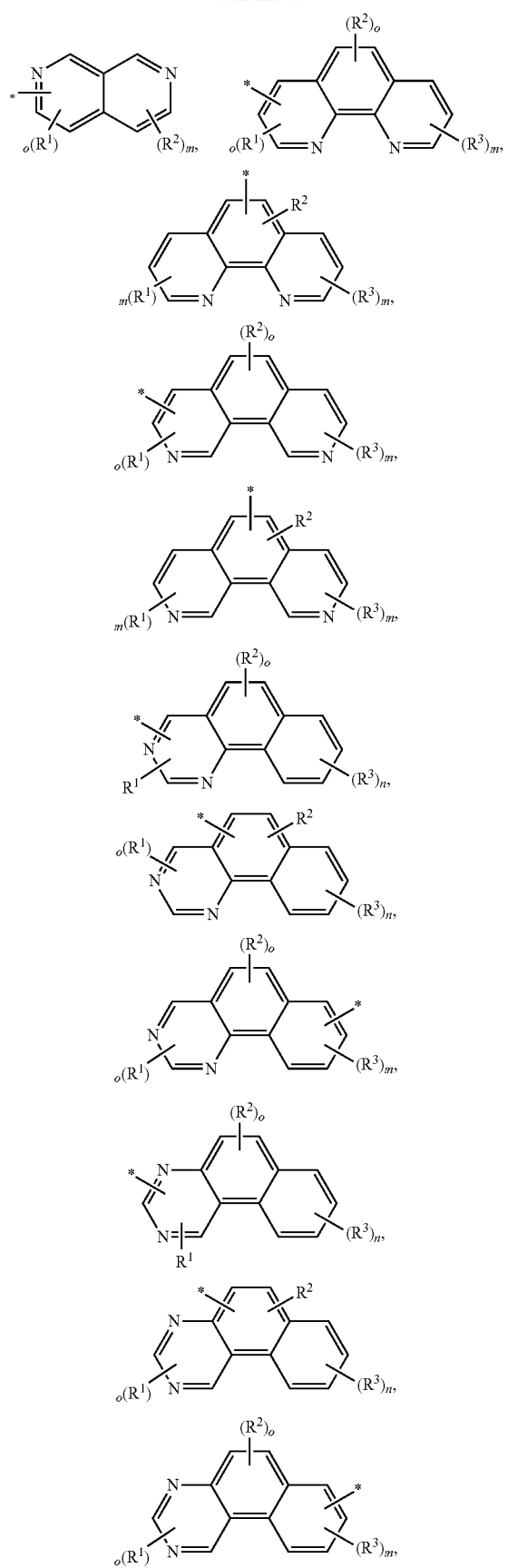
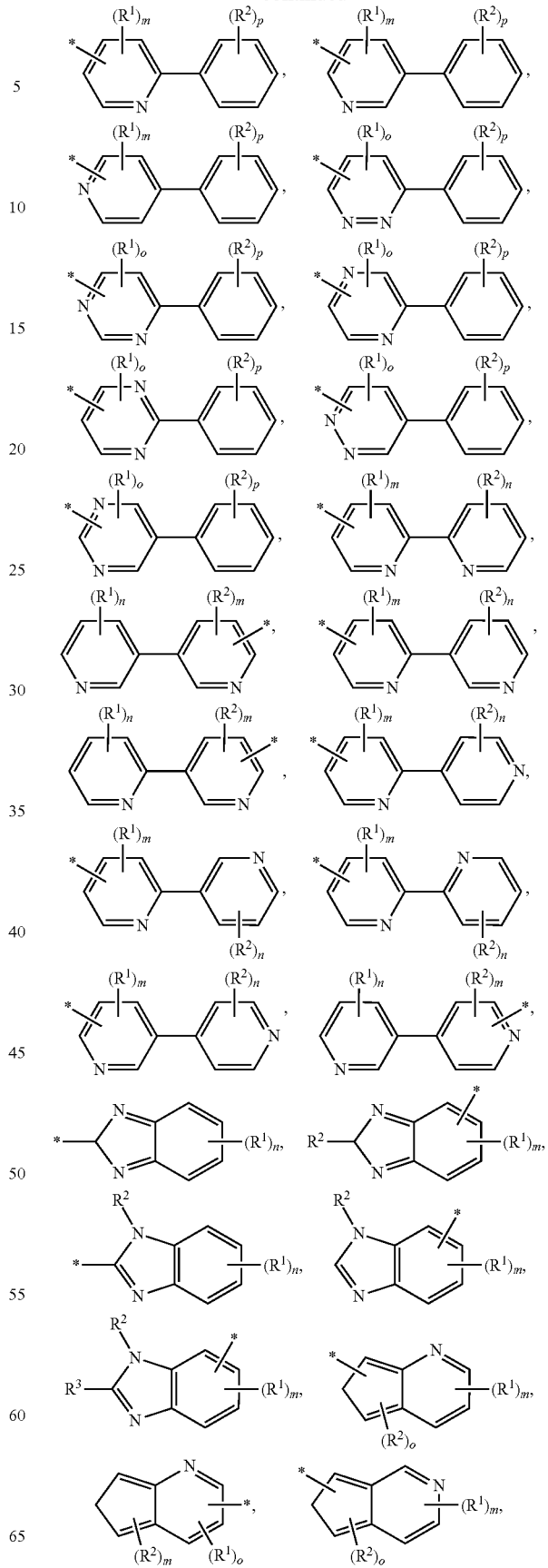

-continued
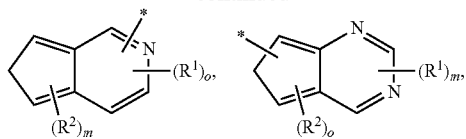
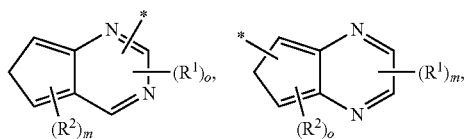
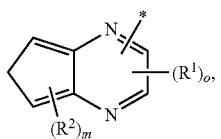
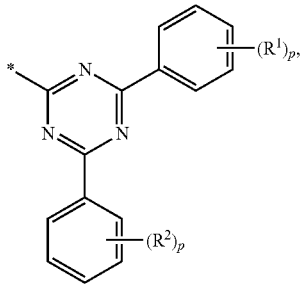
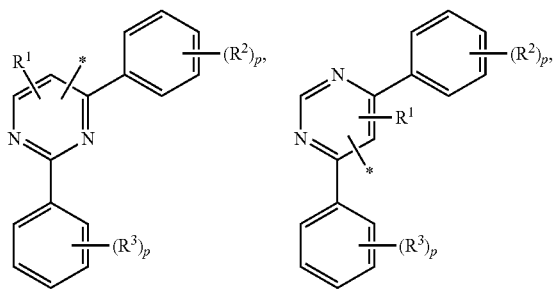
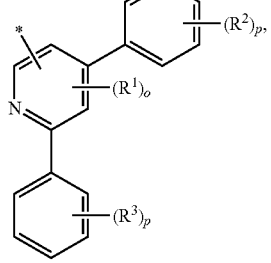
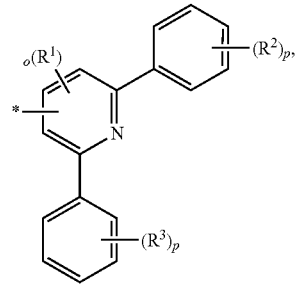
-continued
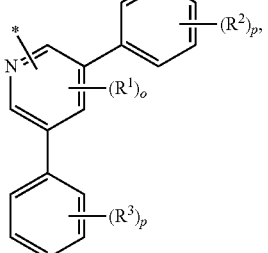
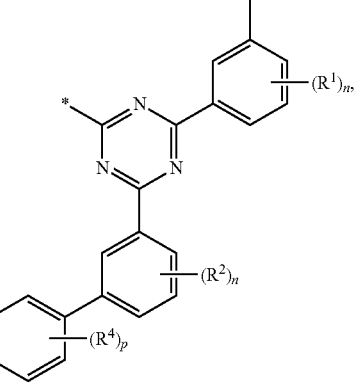
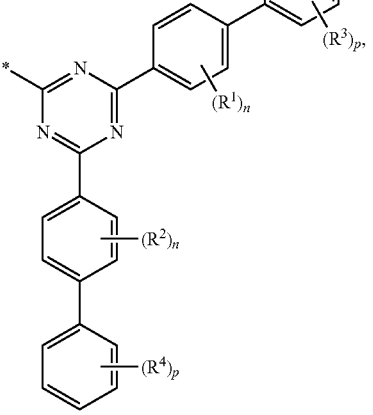
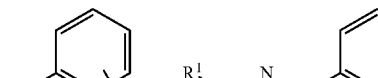
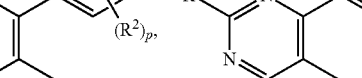

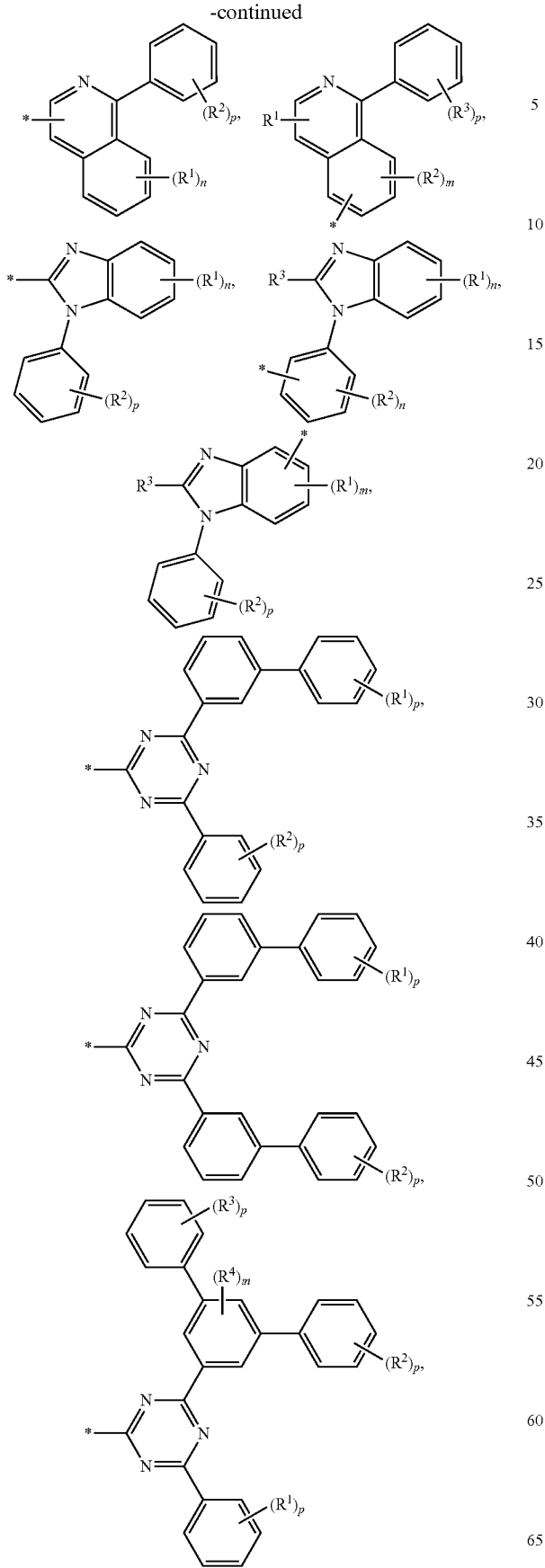
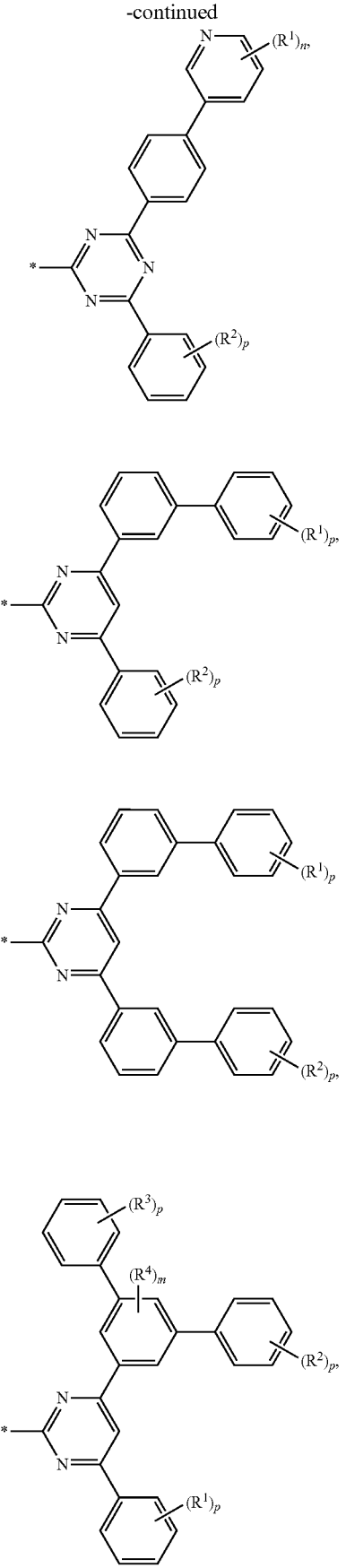

-continued
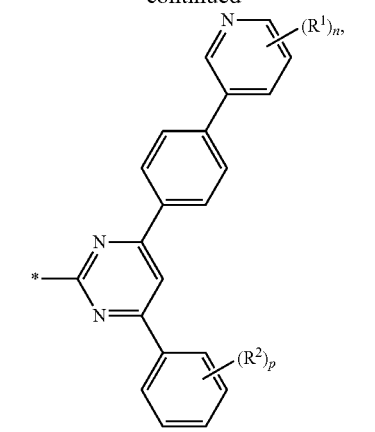
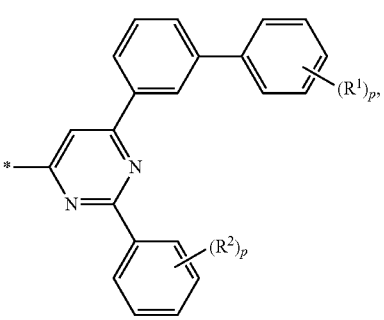
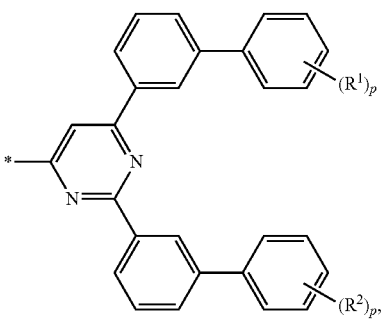
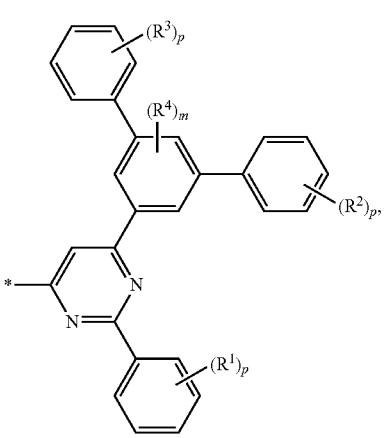
-continued
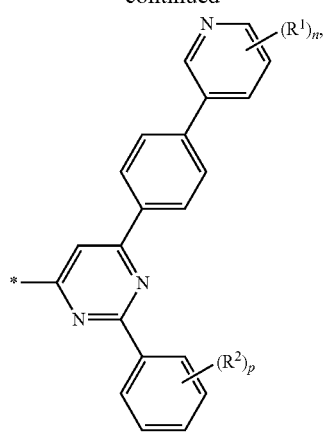
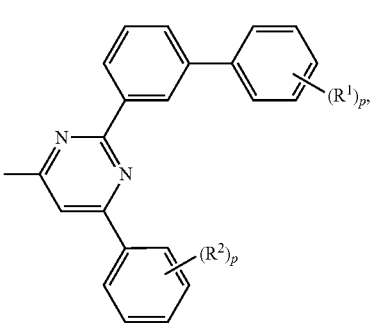
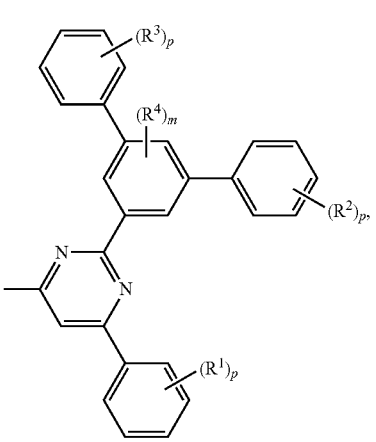
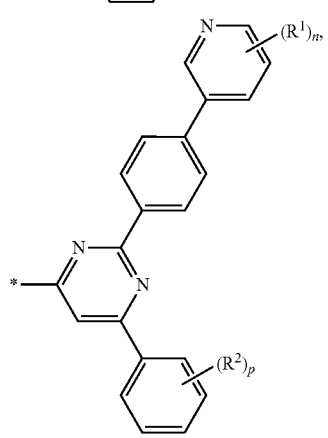

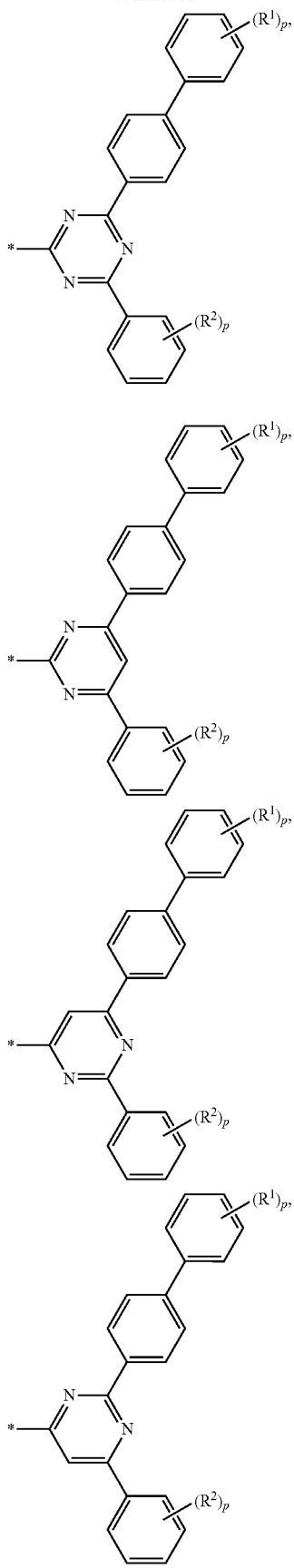
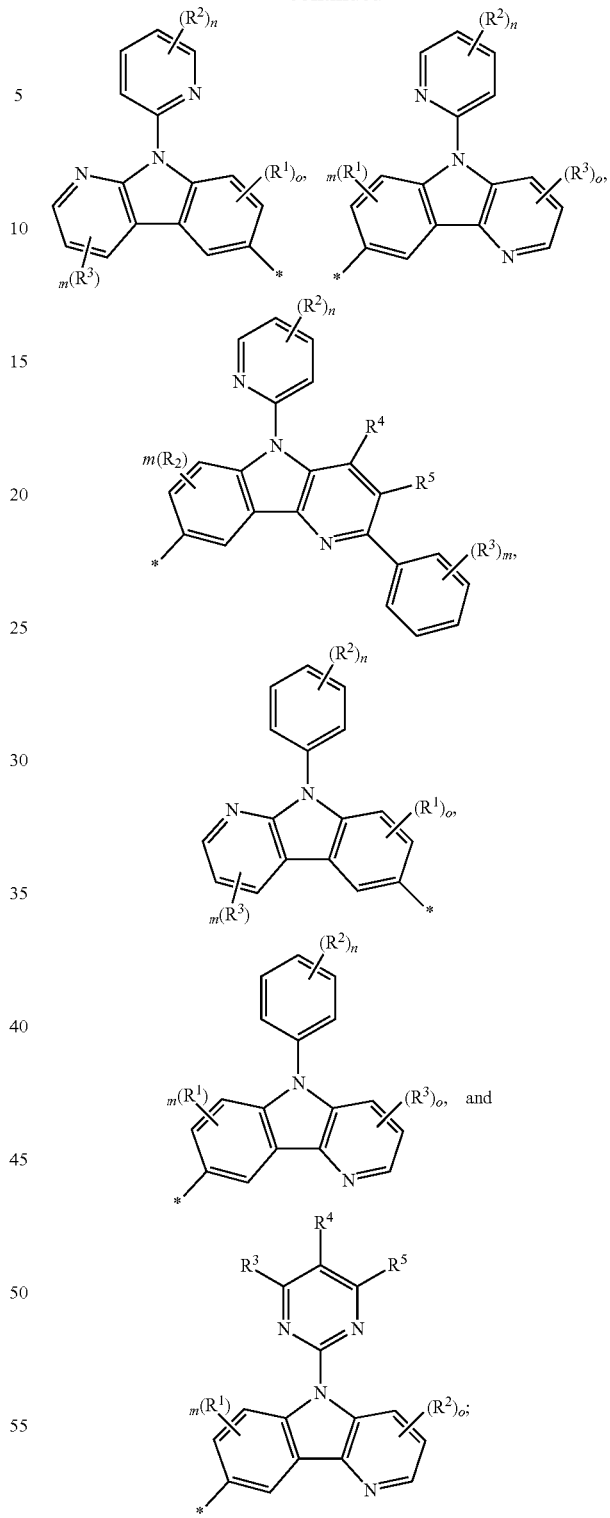
wherein o is an integral from 0 to 2; m is an integral from 0 to 3; n is an integral from 0 to 4; p is an integral from 0 to 5;
wherein $R^1$ to $R^4$ are each independently selected from the group consisting of: a deuterium atom, a halogen group, a cyano group, a nitro group, a trifluoromethyl group, an alkyl group having 1 to 12 carbon atoms, an alkenyl group having 2 to 12 carbon atoms, an alkynyl group having 2 to 12 carbon atoms, a cycloalkyl group having 3 to 30 carbon atoms, a heterocycloalkyl group having 3 to 30 carbon atoms, an aryl group having 6 to 30 carbon atoms, a heteroaryl group having 3 to 30 carbon atoms, an alkoxy group having 1 to 40 carbon atoms, an aryloxy group having 6 to 30 carbon atoms, an alkylsilyl group having 1 to 40 carbon atoms, an arylsilyl group having 6 to 30 carbon atoms, an alkylboron group having 1 to 30 carbon atoms, an arylboron group having 6 to 30 carbon atoms, a phosphine group having 1 to 30 carbon atoms, and a phosphine oxide group having 1 to 30 carbon atoms.

Preferably, the aryl groups having 6 to 60 ring carbon atoms and substituted with at least one functional group of $G^1$ and $G^2$ are each selected from the group consisting of: a phenyl group substituted with the at least one functional group, a biphenyl group substituted with the at least one functional group, a terphenyl group substituted with the at least one functional group, a naphthyl group substituted with the at least one functional group, a phenanthryl group substituted with the at least one functional group, an anthracenyl group substituted with the at least one functional group, a benzanthryl group substituted with the at least one functional group, a fluorenyl group substituted with the at least one functional group, a chrycenyl group substituted with the at least one functional group, a fluoranthenyl group substituted with the at least one functional group, and any deuterated analogs thereof.

More preferably, the aryl groups having 6 to 60 ring carbon atoms and substituted with at least one functional group of $G^1$ and $G^2$ are each selected from the group consisting of: a phenyl group substituted with the at least one functional group and a biphenyl group substituted with the at least one functional group.

Specifically, the aryl group having 6 to 60 carbon atoms and substituted with the at least one functional group of $G^1$ and $G^2$ are each independently selected from the group consisting of:

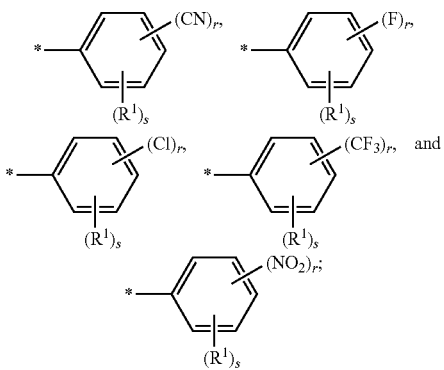

wherein r is an integral from 1 to 5; s is an integral from 0 to 4; the total of r and s is not more than 5;

wherein $R^1$ is selected from the group consisting of: a deuterium atom, an alkyl group having 1 to 12 carbon atoms, an alkenyl group having 2 to 12 carbon atoms, an alkynyl group having 2 to 12 carbon atoms, a cycloalkyl group having 3 to 30 carbon atoms, a heterocycloalkyl group having 3 to 30 carbon atoms, an aryl group having 6 to 30 carbon atoms, a heteroaryl group having 3 to 30 carbon atoms, an alkoxy group having 1 to 12 carbon atoms, an aryloxy group having 6 to 30 carbon atoms, an alkylsilyl group having 1 to 12 carbon atoms, an arylsilyl group having 6 to 30 carbon atoms, an alkylboron group having 1 to 12 carbon atoms, and an arylboron group having 6 to 30 carbon atoms.

Preferably, X is selected from the group consisting of: a deuterium atom, a fluoro group, a chloro group, a bromo group, a phenyl group, a biphenyl group, a terphenyl group, a naphthyl group, a phenanthryl group, an anthracenyl group, a benzanthryl group, a fluorenyl group, a chrycenyl group, a fluoranthenyl group, a deuterated phenyl group, a deuterated biphenyl group, a deuterated terphenyl group, a deuterated naphthyl group, a deuterated phenanthryl group, a deuterated anthracenyl group, a deuterated benzanthryl group, a deuterated fluorenyl group, a deuterated chrycenyl group, and a deuterated fluoranthenyl group.

More preferably, X is selected from the group consisting of: a deuterium atom, a fluoro group, a chloro group, a bromo group, a phenyl group, a biphenyl group, a deuterated phenyl group, and a deuterated biphenyl group.

Preferably, Y is selected from the group consisting of: a deuterium atom, an unsubstituted phenyl group, an unsubstituted biphenyl group, an unsubstituted terphenyl group, an unsubstituted naphthyl group, an unsubstituted phenanthryl group, an unsubstituted anthracenyl group, an unsubstituted benzanthryl group, an unsubstituted fluorenyl group, an unsubstituted chrycenyl group, an unsubstituted fluoranthenyl group, a deuterated phenyl group, a deuterated biphenyl group, a deuterated terphenyl group, a deuterated naphthyl group, a deuterated phenanthryl group, a deuterated anthracenyl group, a deuterated benzanthryl group, a deuterated fluorenyl group, a deuterated chrycenyl group, a deuterated fluoranthenyl group; an unsubstituted furyl group, an unsubstituted pyrrolyl group, an unsubstituted thiophenyl group; an unsubstituted imidazolyl group, an unsubstituted pyrazolyl group, an unsubstituted triazolyl group, an unsubstituted tetrazolyl group, an unsubstituted oxazolyl group, an unsubstituted isoxazolyl group, an unsubstituted thiazolyl group, an unsubstituted isothiazolyl group, an unsubstituted oxadiazolyl group, an unsubstituted thiadiazolyl group; an unsubstituted pyridyl group, an unsubstituted pyridazinyl group, an unsubstituted pyrimidinyl group, an unsubstituted pyrazinyl group, an unsubstituted triazinyl group; an unsubstituted indolyl group, an unsubstituted isoindolyl group, an unsubstituted benzofuranyl group, an unsubstituted isobenzofuranyl group, an unsubstituted benzothiophenyl group, an unsubstituted isobenzothiophenyl group, an unsubstituted indolizinyl group, an unsubstituted quinolizinyl group, an unsubstituted quinolyl group, an unsubstituted isoquinolyl group, an unsubstituted cinnolyl group, an unsubstituted phthalazinyl group, an unsubstituted quinazolinyl group, an unsubstituted quinoxalinyl group, an unsubstituted benzimidazolyl group, an unsubstituted benzoxazolyl group, an unsubstituted benzothiazolyl group, an unsubstituted indazolyl group, an unsubstituted benzisoxazolyl group, an unsubstituted benzisothiazolyl group, an unsubstituted dibenzofuranyl group, an unsubstituted dibenzothiophenyl group, an unsubstituted carbazolyl group, an unsubstituted biscarbazolyl group, an unsubstituted coumarinyl group, an unsubstituted chromenyl group, an unsubstituted phenanthridinyl group, an unsubstituted acridinyl group, an unsubstituted phenanthrolinyl group, an unsubstituted phenazinyl group, an unsubstituted phenothiazinyl group, an unsubstituted phenoxazinyl group, an unsubstituted azatriphenylenyl group, an unsubstituted diazatriphenylenyl group, an unsubstituted xanthenyl group, an unsubstituted azacarbazolyl group, an unsubstituted azadibenzofuranyl group, an unsubstituted azadibenzothiophenyl group, an unsubstituted benzofuranobenzothiophenyl group, an unsubstituted benzothienobenzothiophenyl group, an unsubstituted dibenzofuranonaphthyl group, an unsubstituted dibenzothienonaphthyl group, an unsubstituted dinaphthothienothiophenyl group, an unsubstituted dinaphtho carbazolyl group, an unsubstituted dibenzo[b,f]azepin group, an unsubstituted tribenzo[b,d,f]azepin group, an unsubstituted dibenzo[b,f]oxepin group, an unsubstituted tribenzo[b,d,f]oxepin group, a phenyl group substituted with a functional group, a biphenyl group substituted with a functional group, a terphenyl group substituted with a functional group, a naphthyl group substituted with a functional group, a phenanthryl group substituted with a functional group, an anthracenyl group substituted with a functional group, a benzanthryl group substituted with a functional group, a fluorenyl group substituted with a functional group, a chrycenyl group substituted with a functional group, and a fluoranthenyl group substituted with a functional group; wherein the functional group is selected from the group consisting of: a cyano group, a nitro group, a trifluoromethyl group, a fluoro group, and a chloro group.

More preferably, Y is selected from the group consisting of: an unsubstituted phenyl group, an unsubstituted biphenyl group, a phenyl group substituted with a functional group, and a biphenyl group substituted with a functional group; wherein the functional group is selected from the group consisting of: a cyano group, a nitro group, a trifluoromethyl group, a fluoro group, and a chloro group.

Preferably, $L^1$ and $L^2$ are each independently selected from the group consisting of:

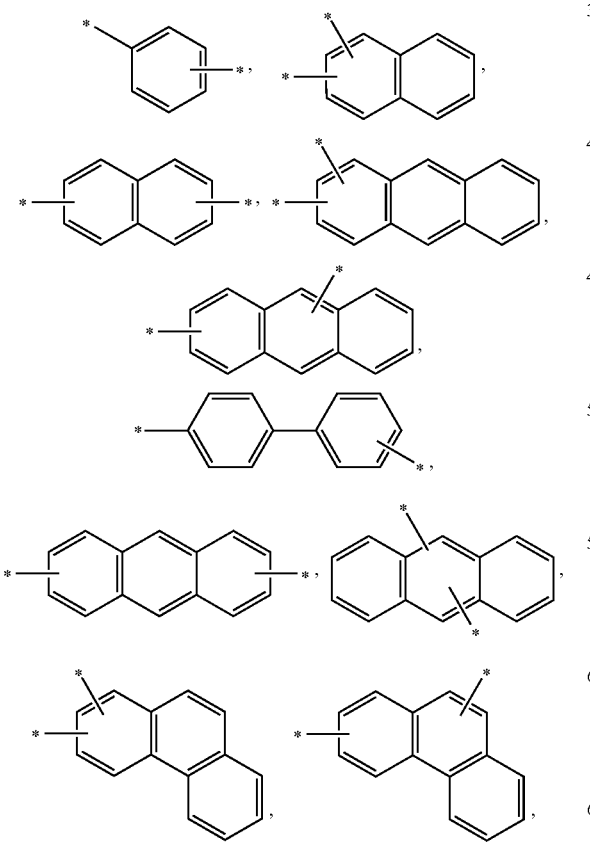

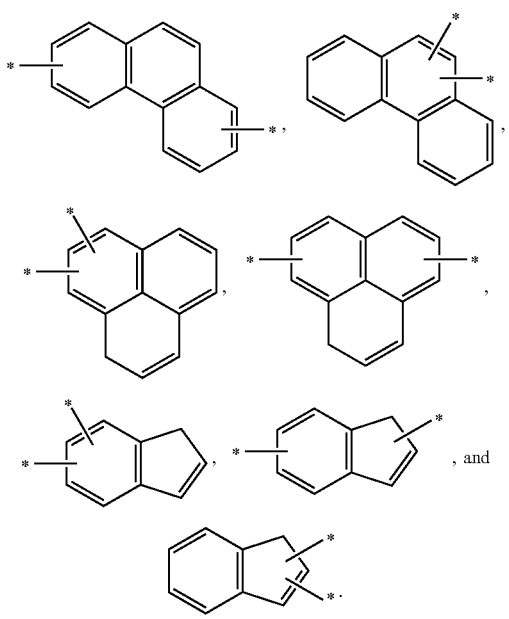

More preferably, $L^1$ and $L^2$ are each independently selected from the group consisting of:

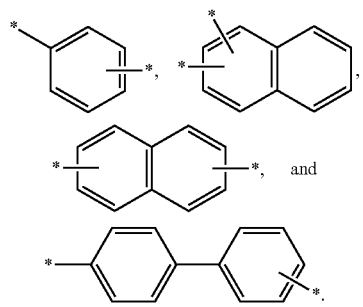

Specifically, the compound may contain a specific group ($L^1$-$G^1$) attached on the lower part of the main skeletal structures, such as:

Compound 1

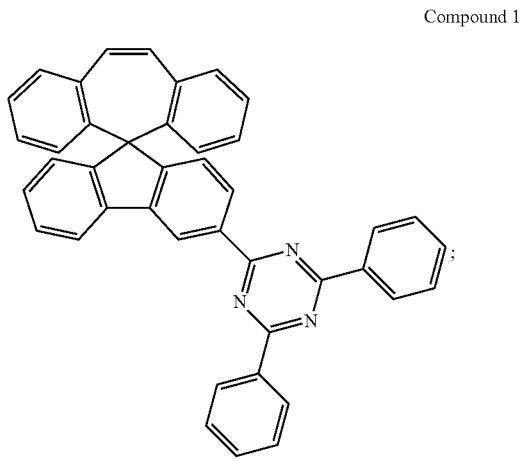

Compound 2
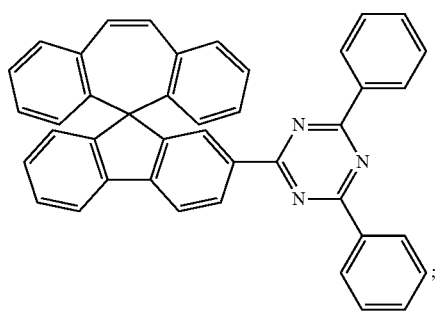
Compound 3
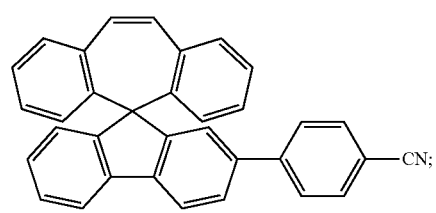
Compound 4
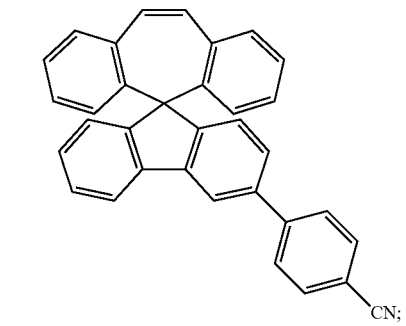
Compound 5
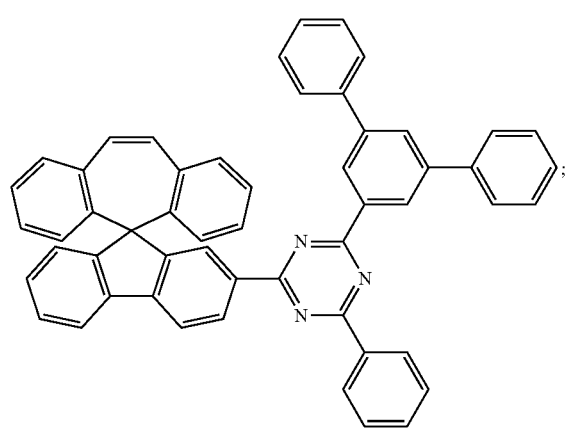
Compound 6
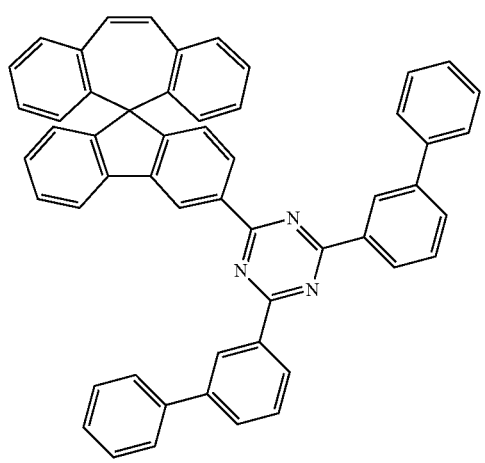
Compound 7
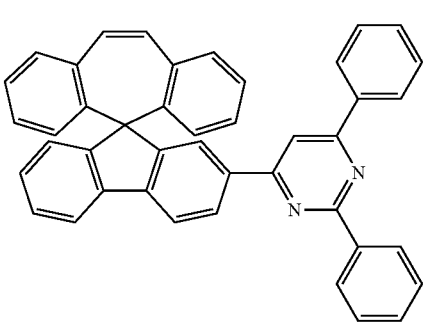
Compound 8
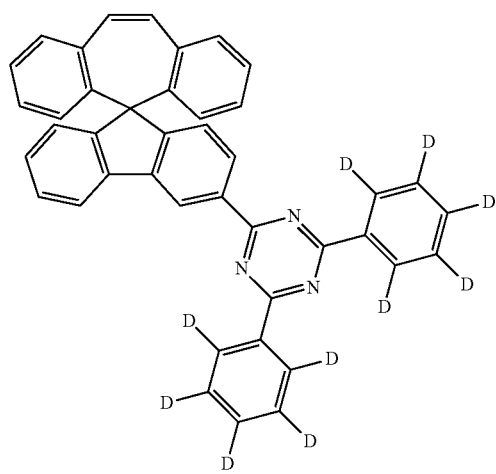
Compound 9
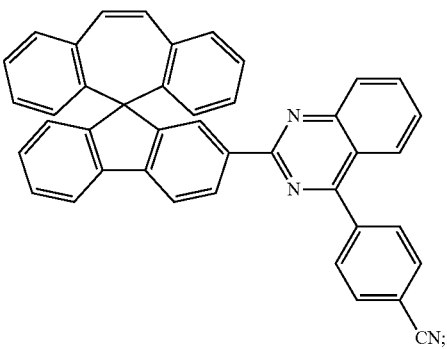

Compound 10
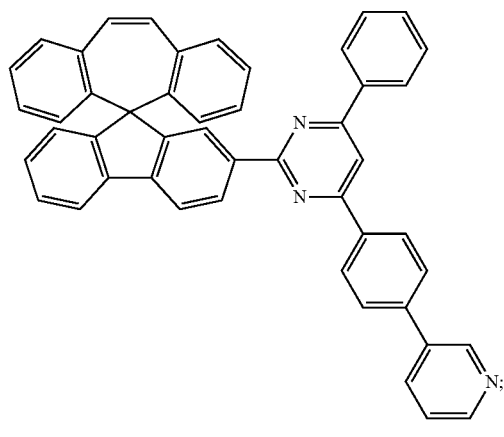
Compound 11
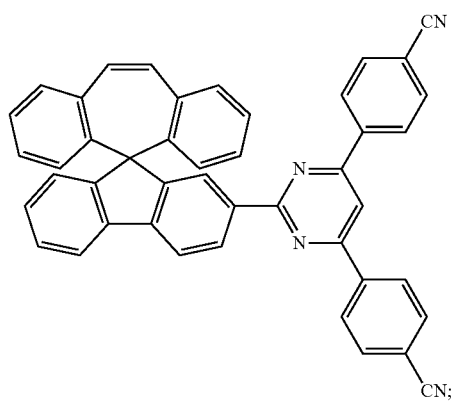
Compound 12
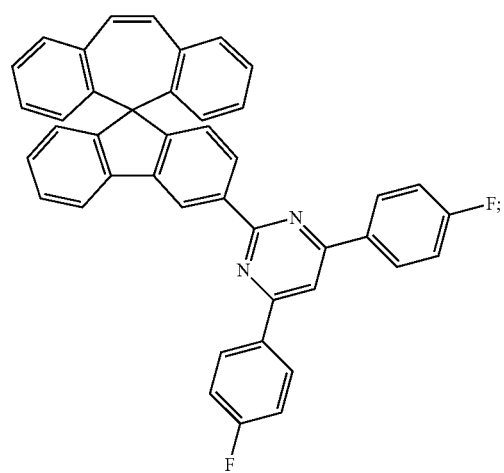
Compound 26
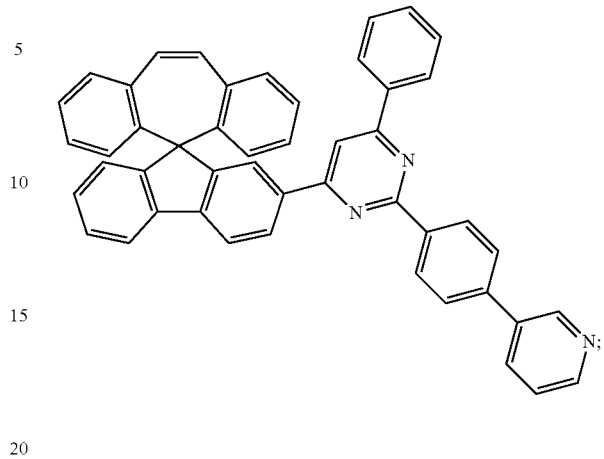
Compound 29
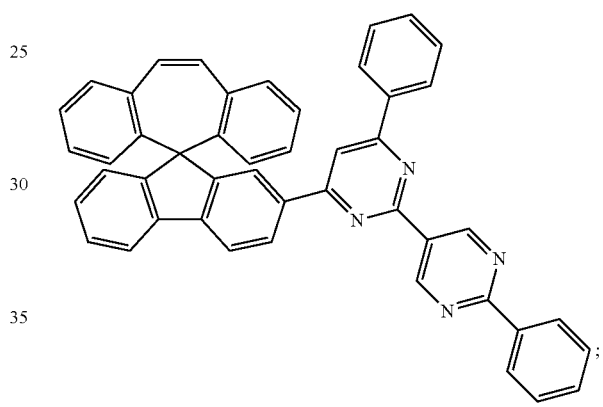
Compound 33
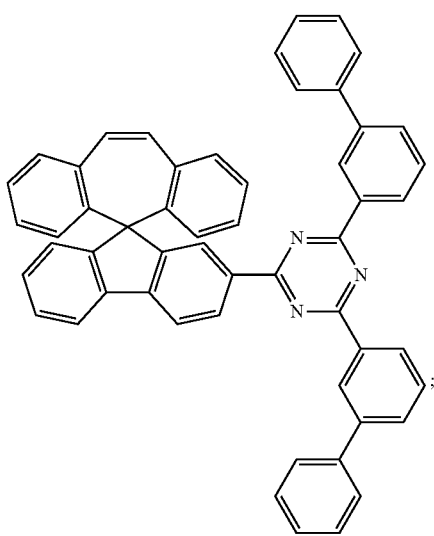

Compound 36
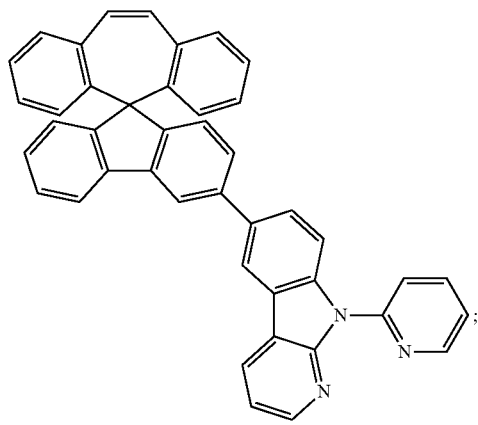
Compound 37
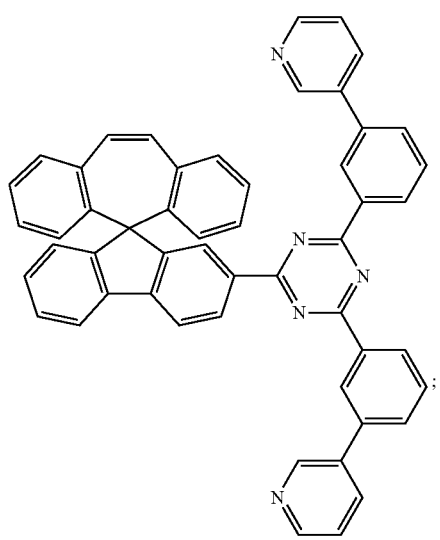
Compound 38
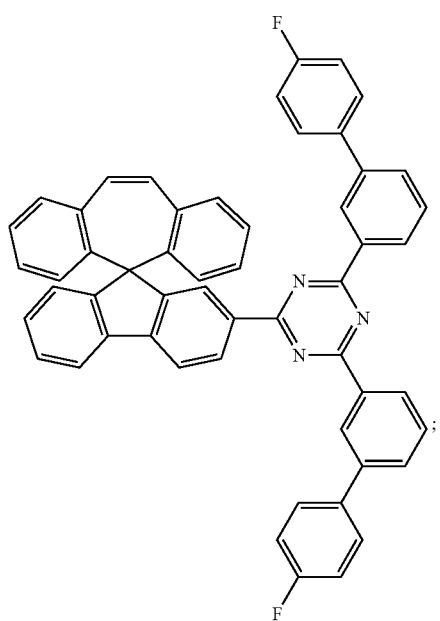
Compound 39
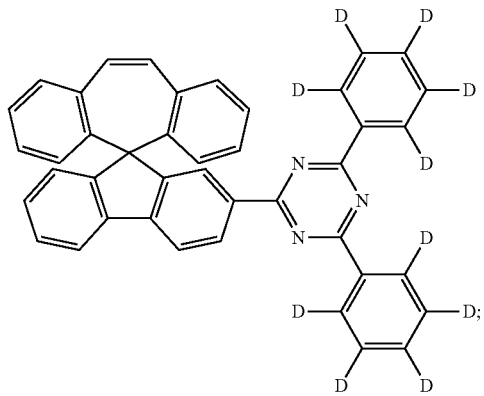
Compound 40
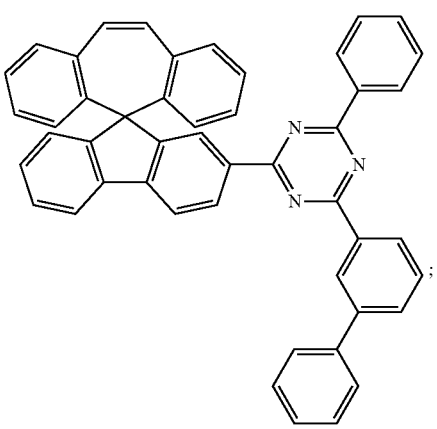
Compound 41
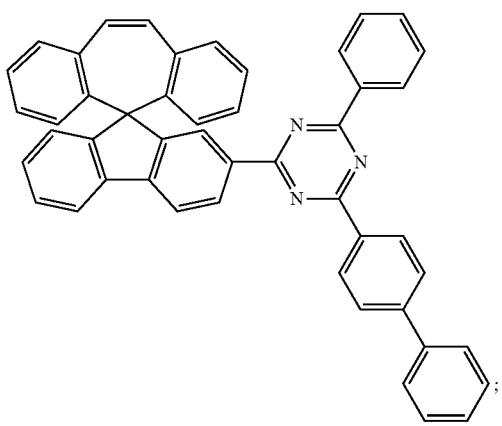

Compound 42
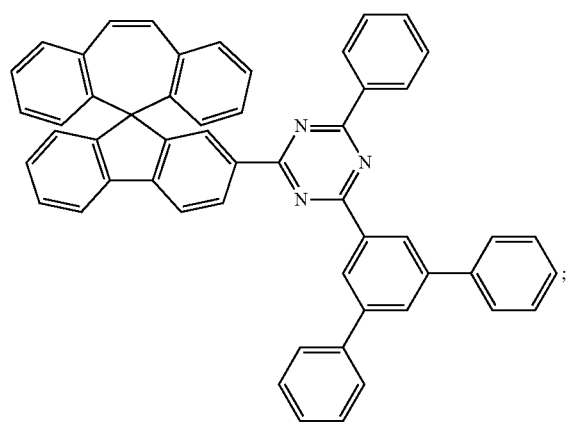
Compound 43
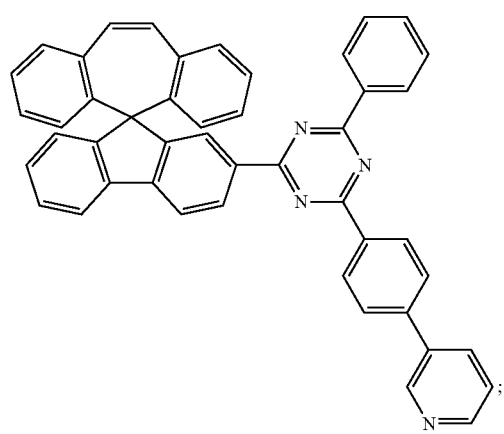
Compound 44
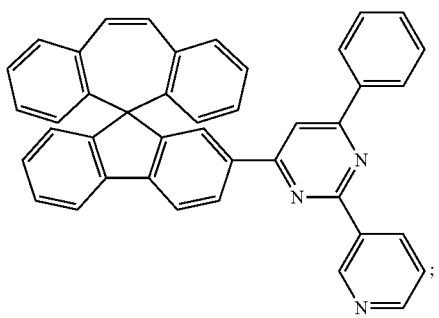
Compound 45
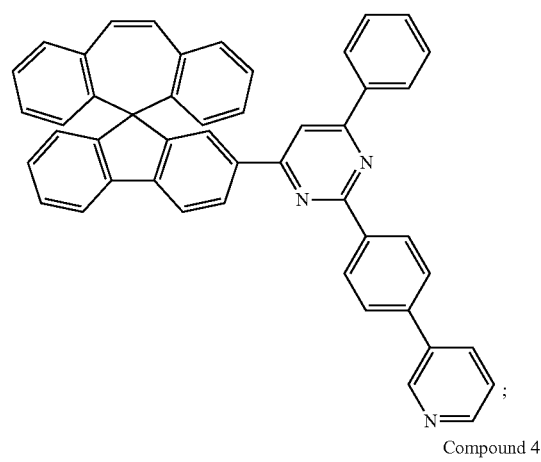
Compound 46
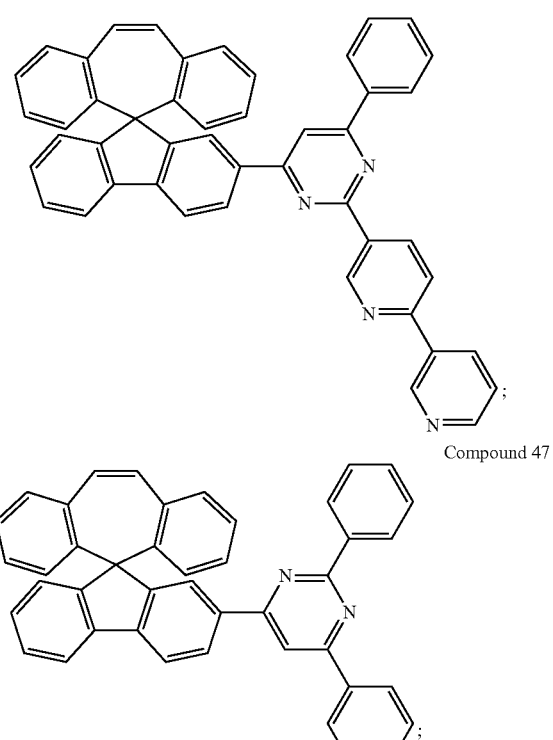
Compound 47
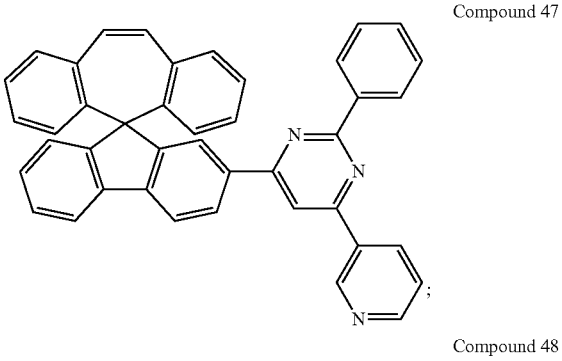
Compound 48
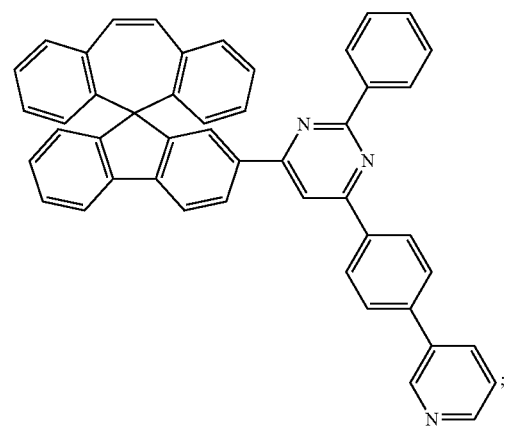

Compound 49
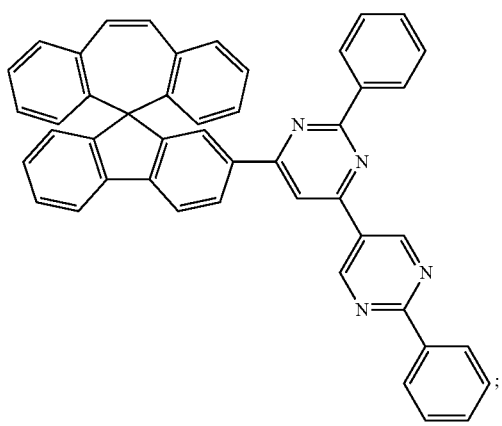
Compound 50
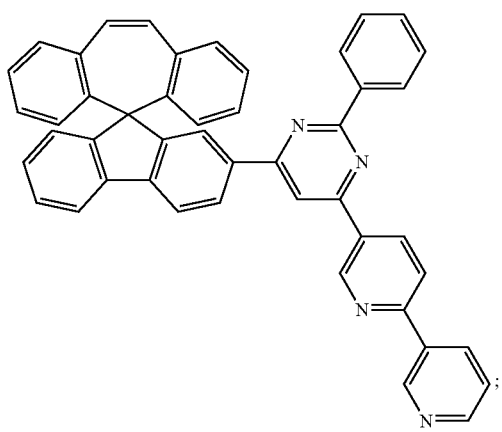
Compound 51
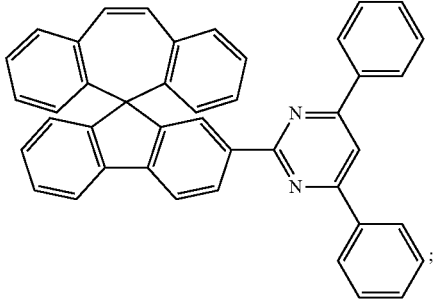
Compound 52
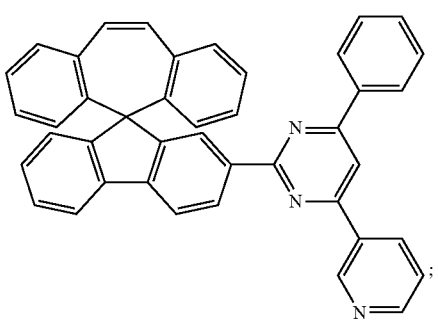
Compound 53
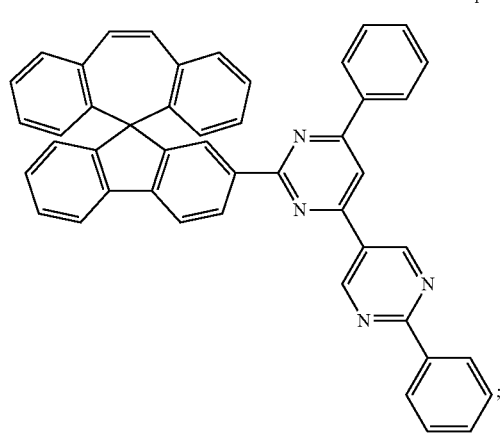
Compound 54
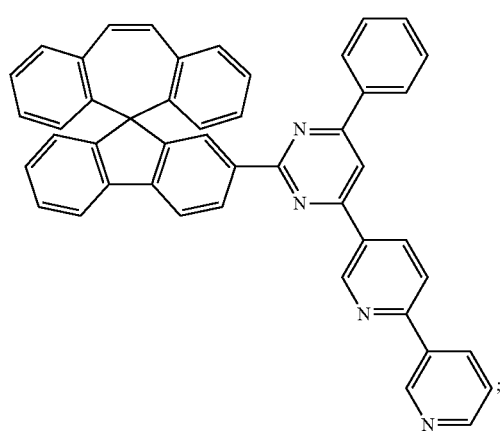
Compound 55
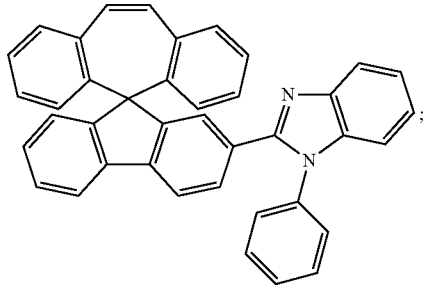
Compound 56
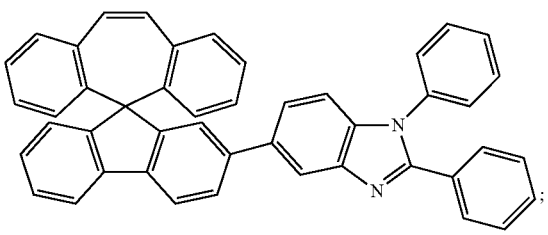

Compound 57
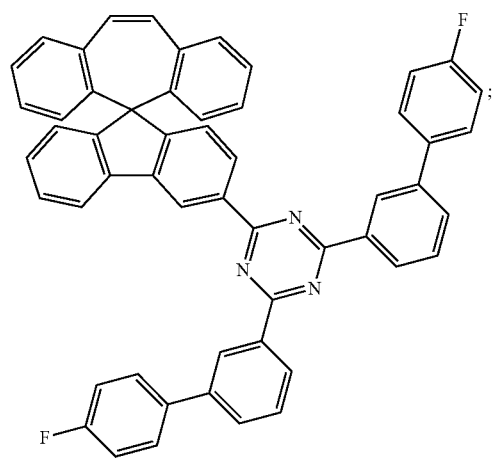
Compound 58
Compound 59
Compound 60
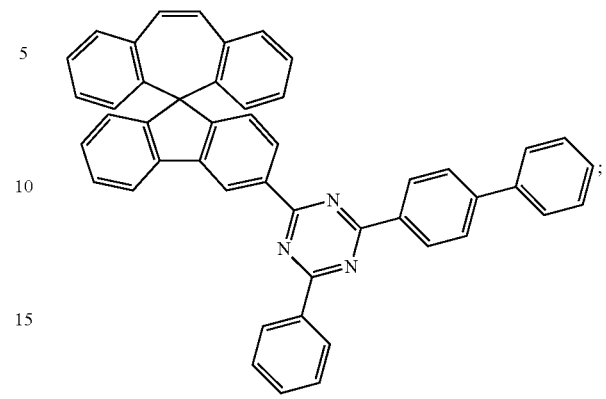
Compound 61
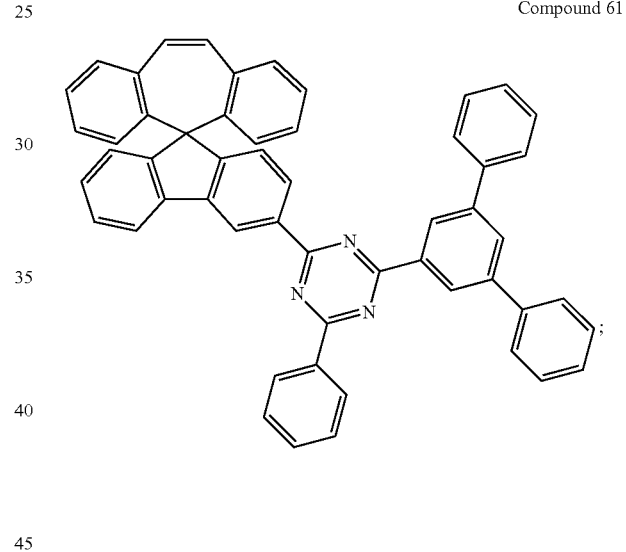
Compound 62
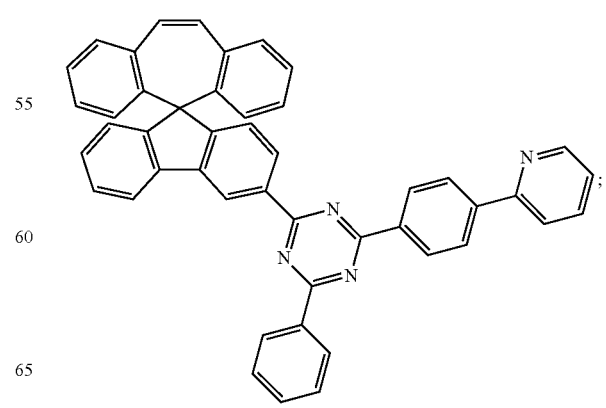
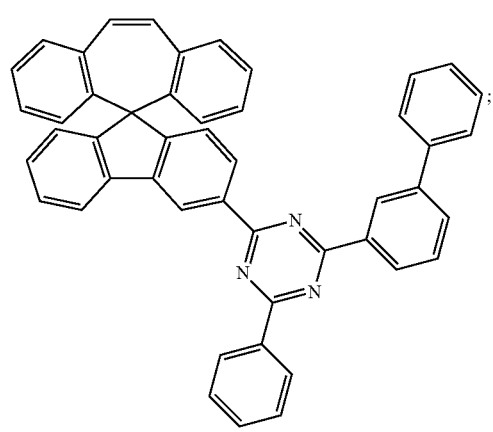

Compound 63
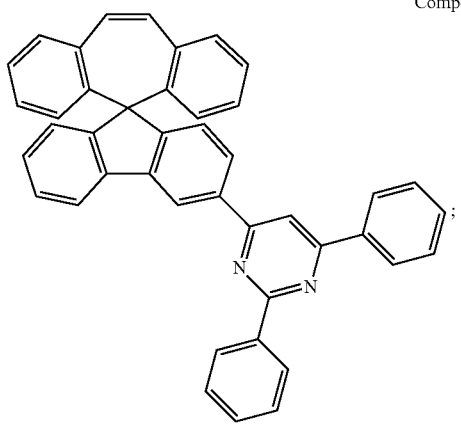
Compound 66
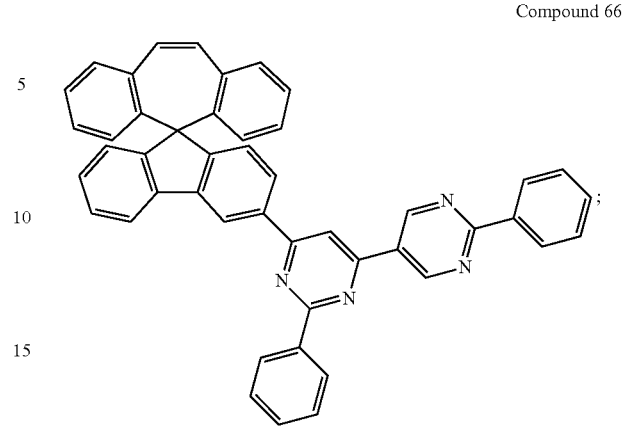
Compound 64
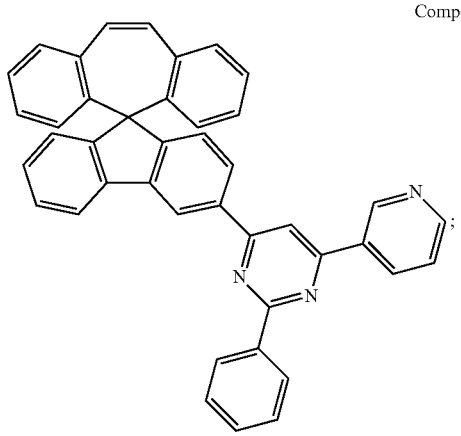
Compound 67
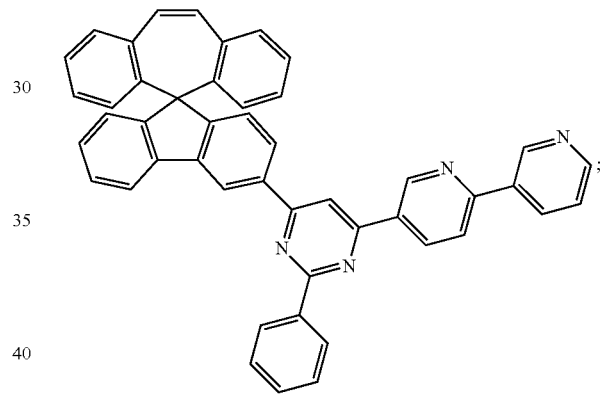
Compound 65
Compound 68
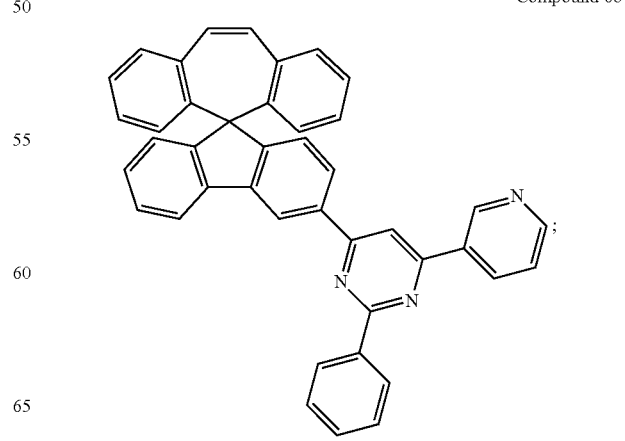

Compound 69
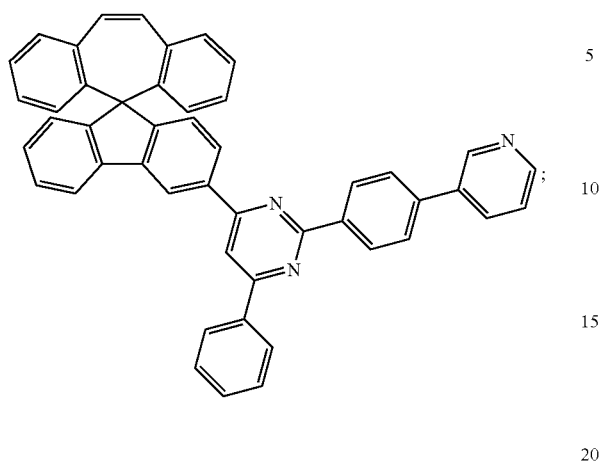
Compound 70
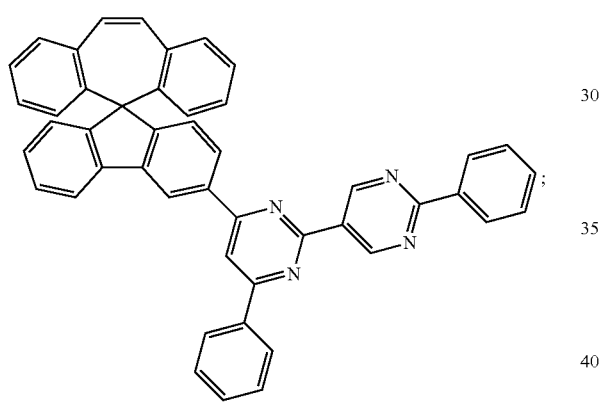
Compound 71
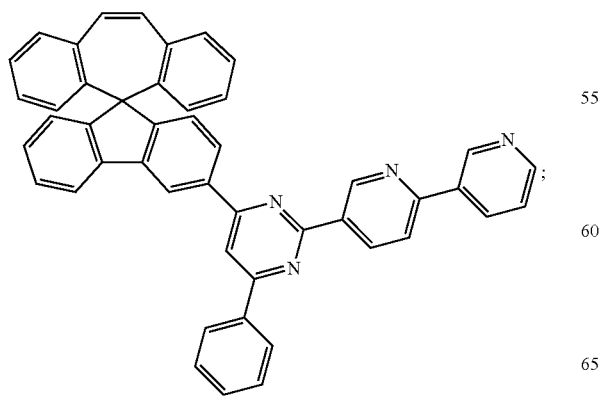
Compound 72
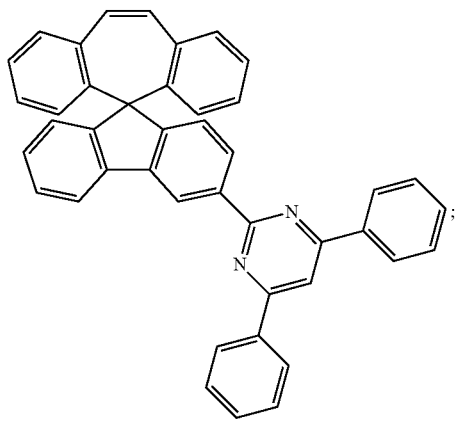
Compound 73
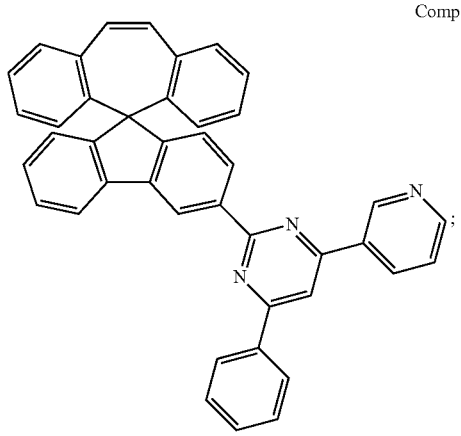
Compound 74
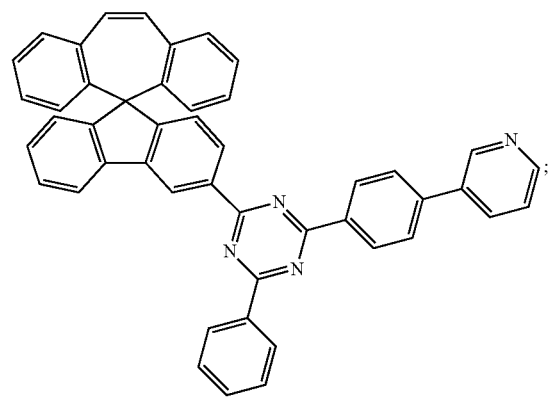

Compound 75
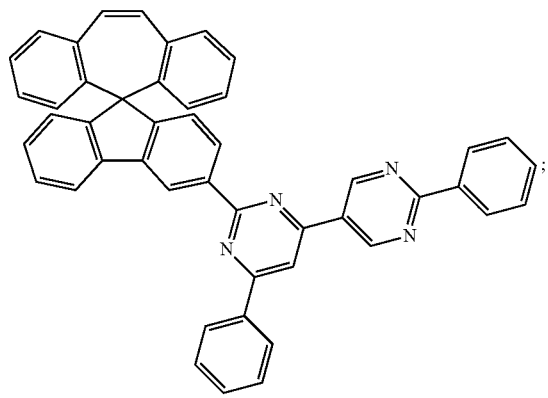
Compound 76
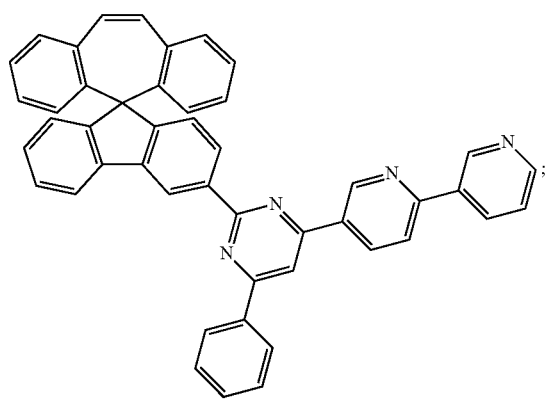
Compound 77
Compound 78
Compound 109
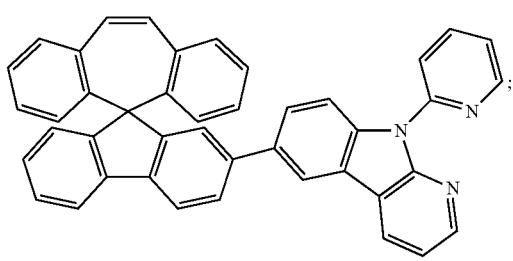
Compound 110
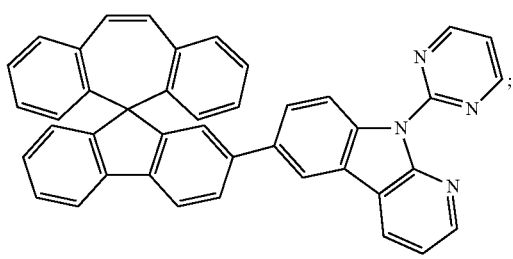
Compound 111
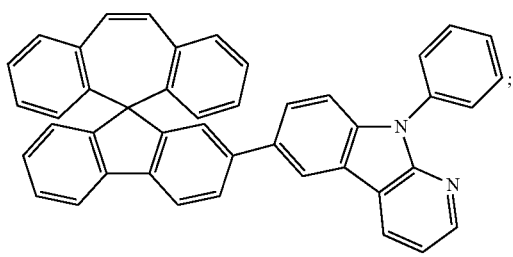
Compound 112
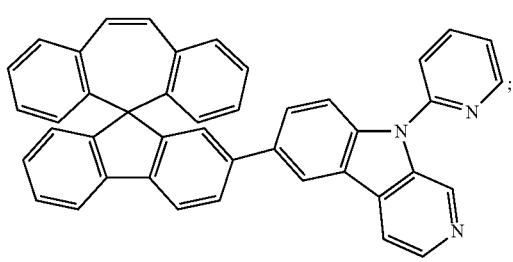
Compound 113
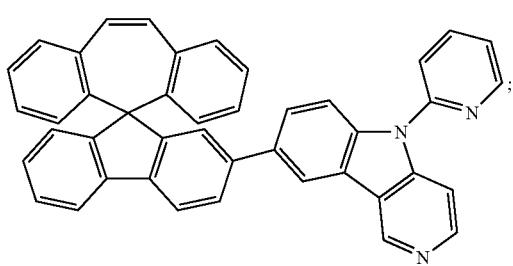

Compound 114
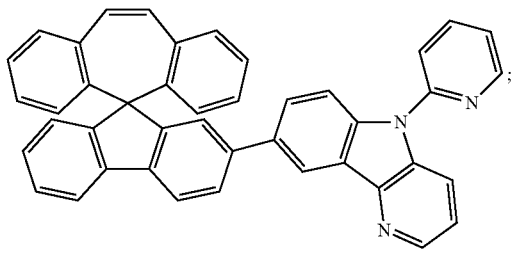
Compound 115
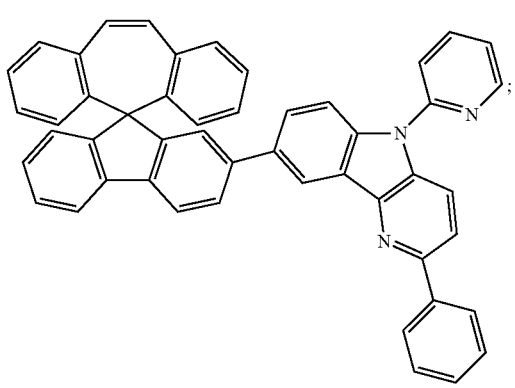
Compound 116
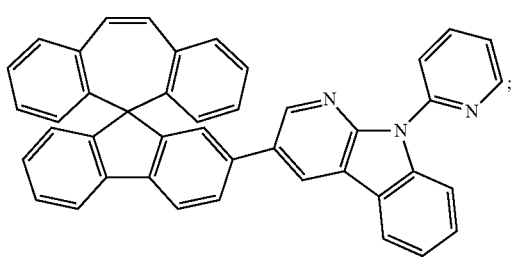
Compound 117
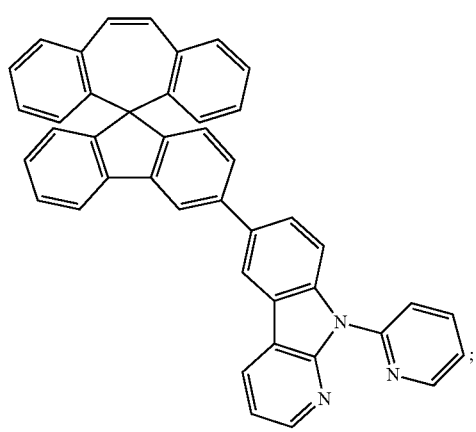
Compound 118
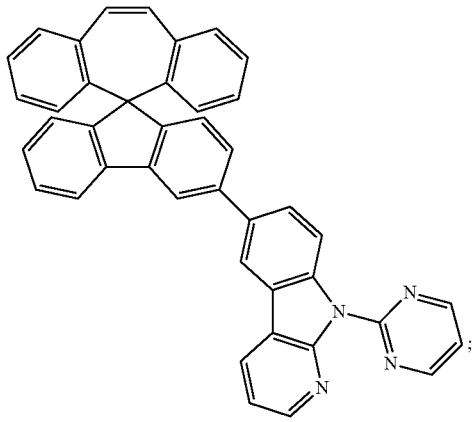
Compound 119
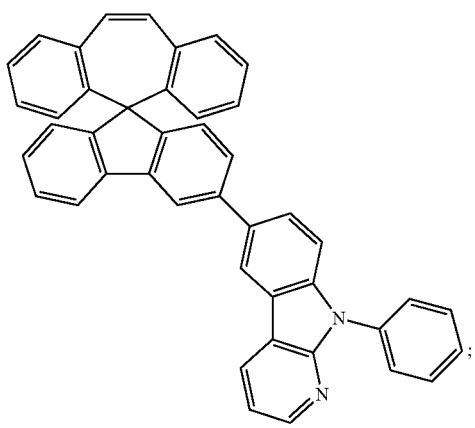
Compound 120
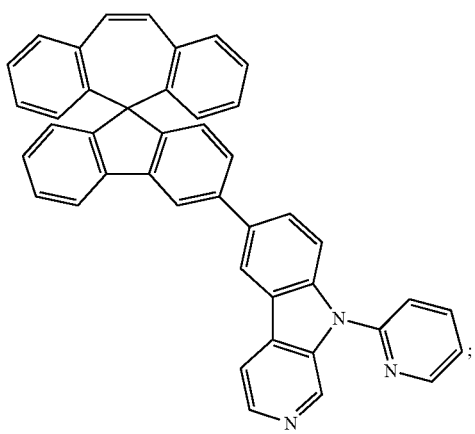

Compound 121
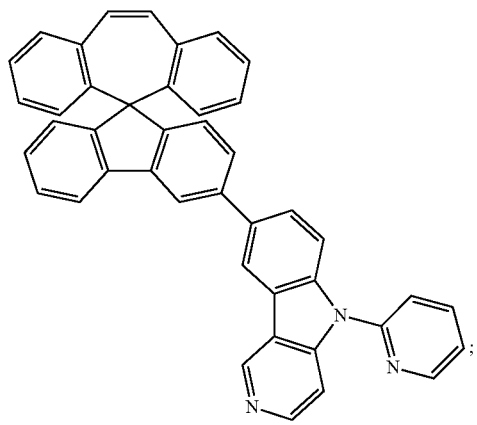
Compound 122
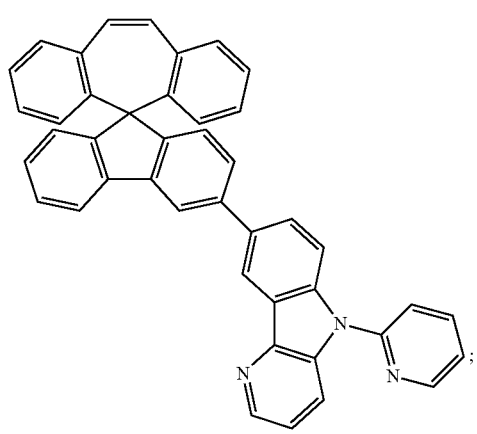
Compound 123
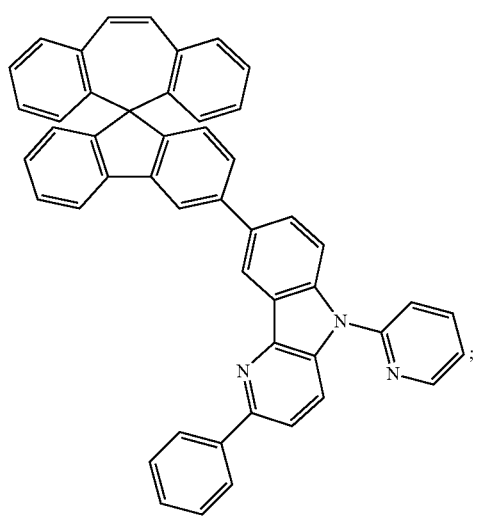
Compound 124
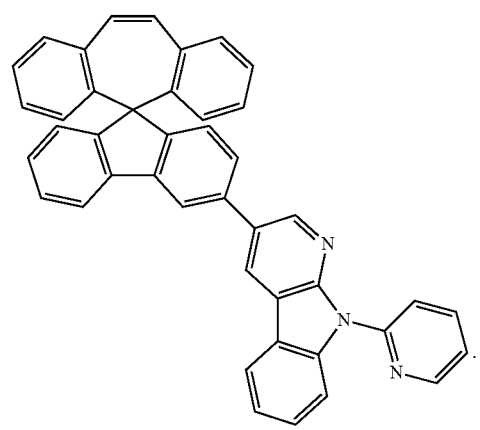
Or, the compound may contain a specific group ($L^2$-$G^2$) attached on the upper part of the main skeletal structures, such as:
Compound 13
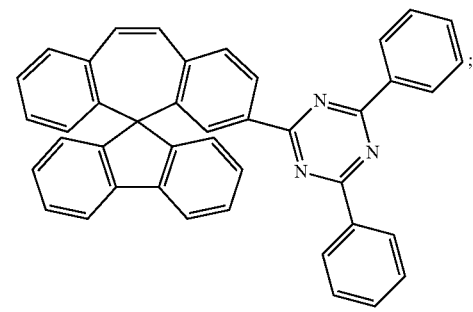
Compound 14
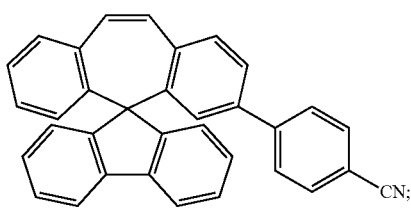
Compound 16
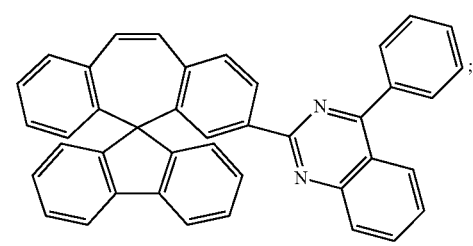

Compound 17
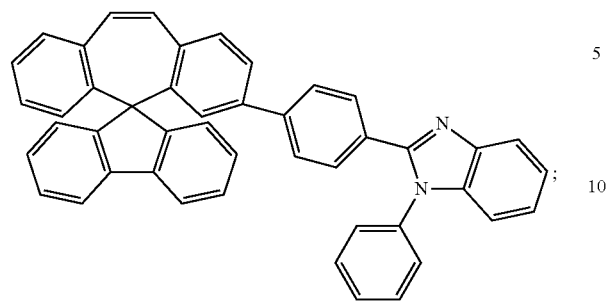
Compound 18
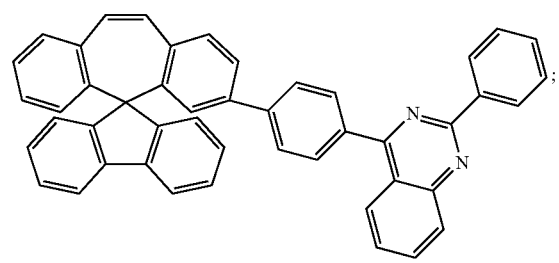
Compound 19
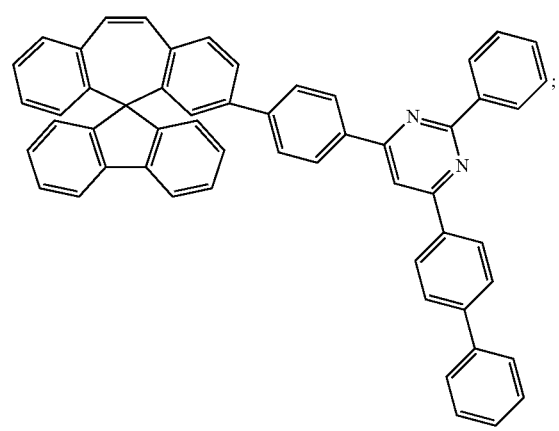
Compound 20
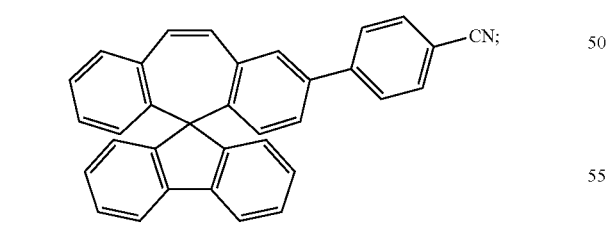
Compound 21
Compound 22
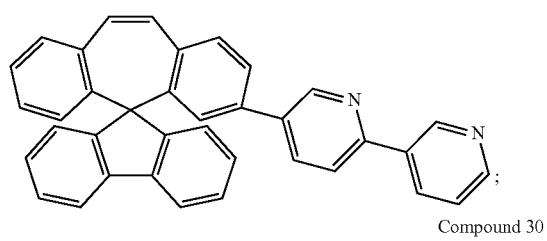
Compound 30
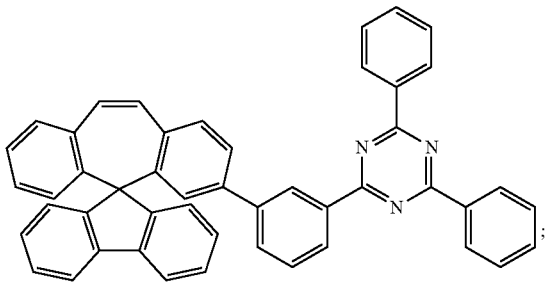
Compound 31
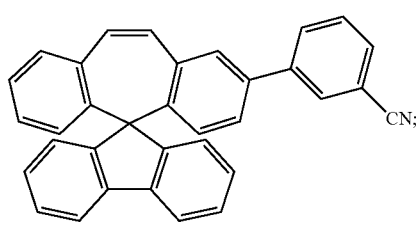
Compound 35
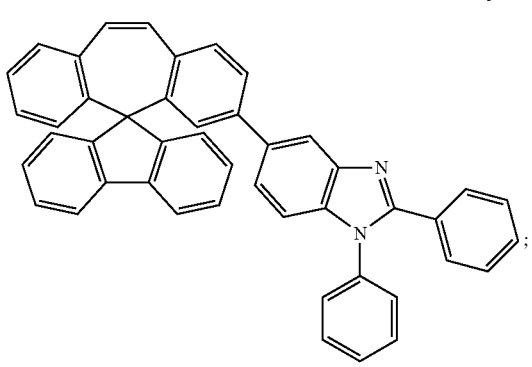
Compound 79
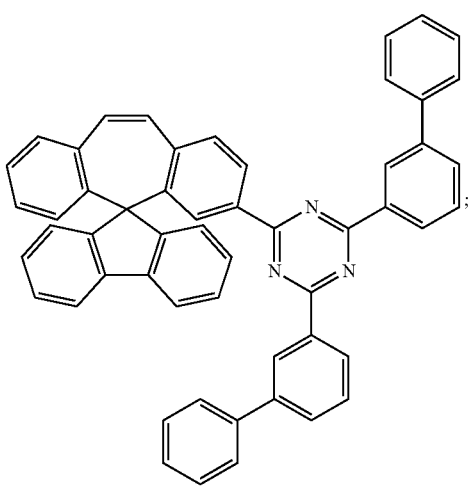

-continued
Compound 80
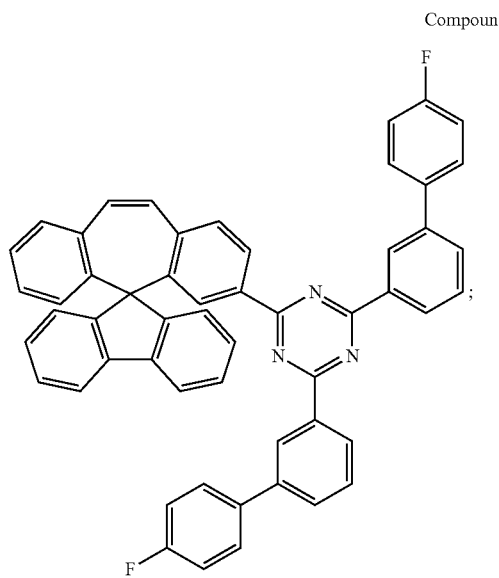
Compound 81
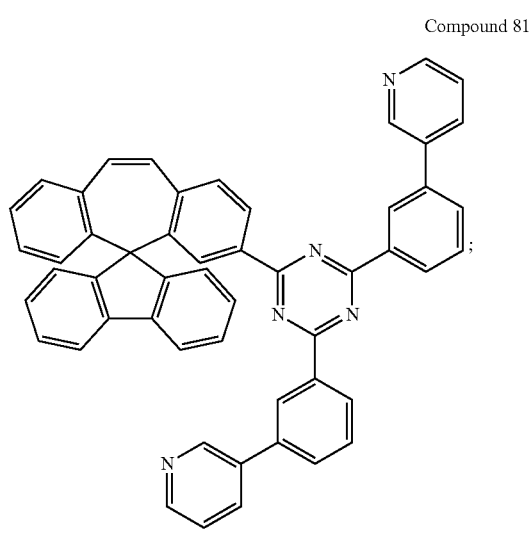
Compound 82
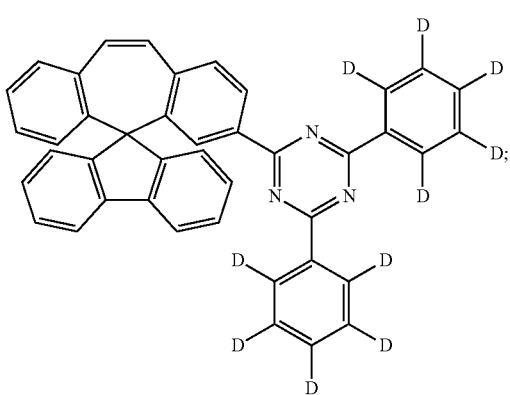
-continued
Compound 83
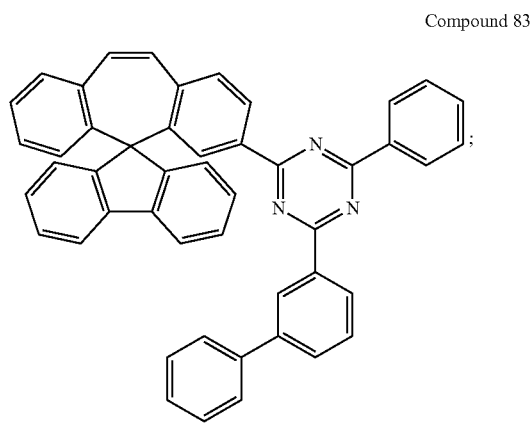
Compound 84
Compound 85
Compound 86
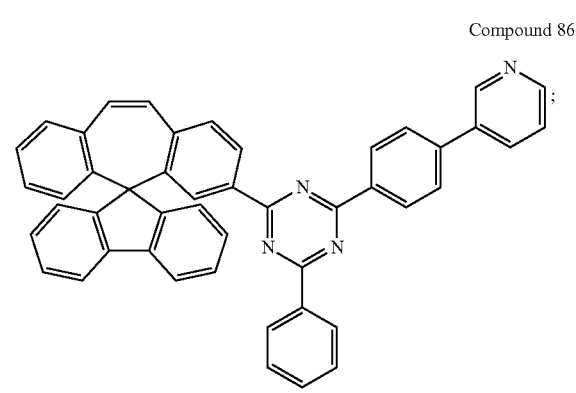

Compound 87
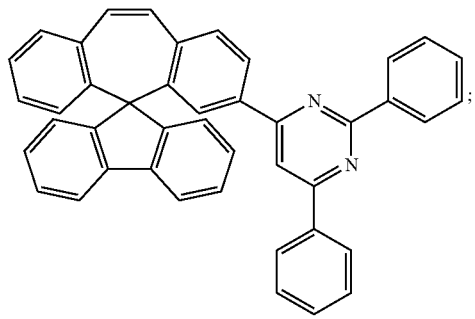
Compound 88
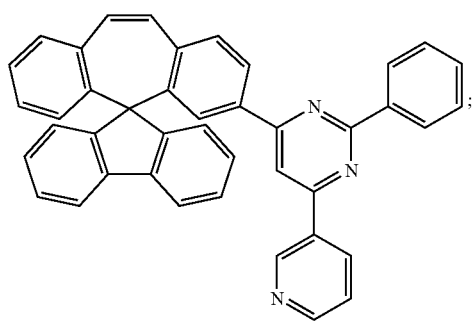
Compound 89
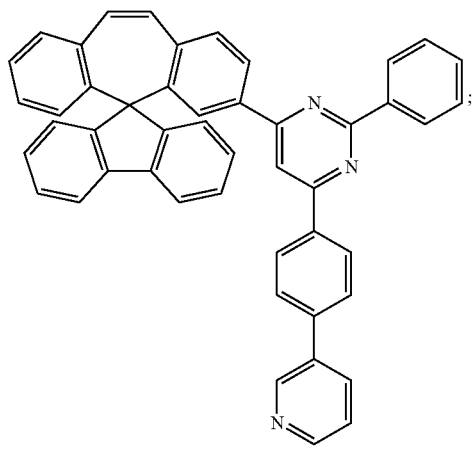
Compound 90
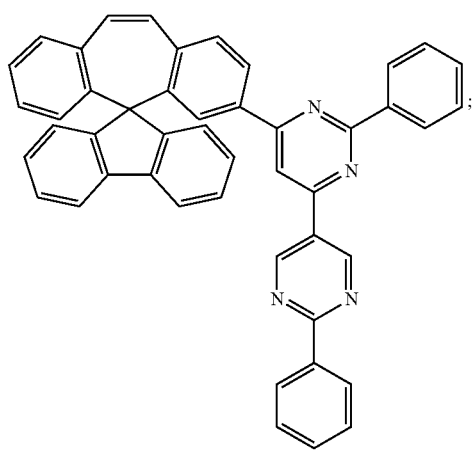
Compound 91
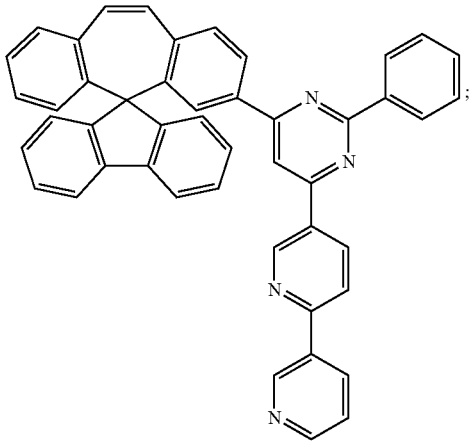
Compound 92
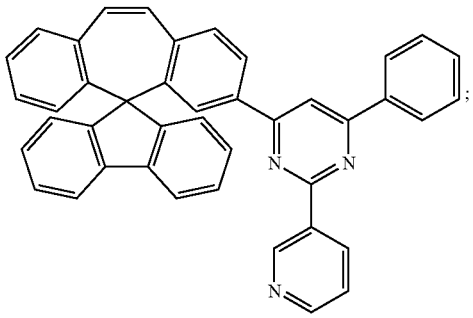
Compound 93
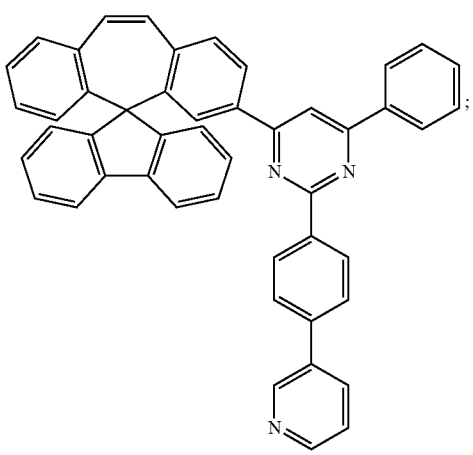

Compound 94
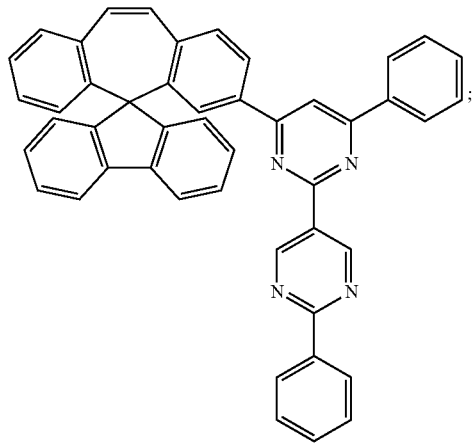
Compound 95
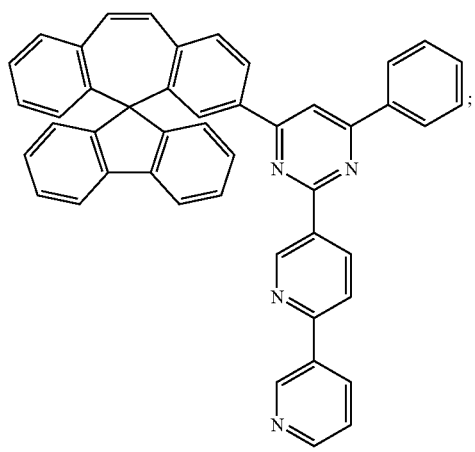
Compound 96
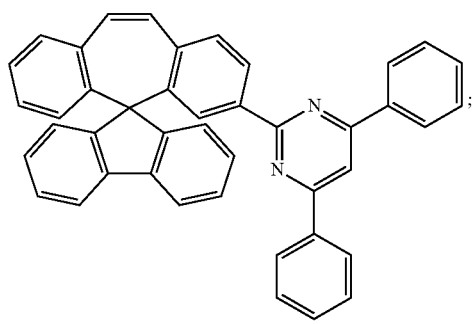
Compound 97
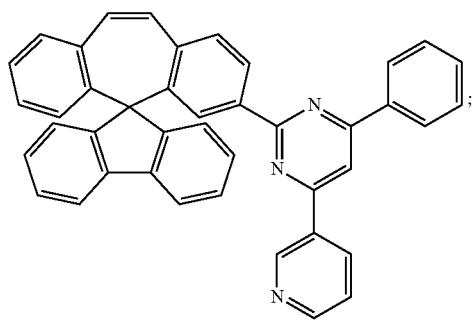
Compound 98
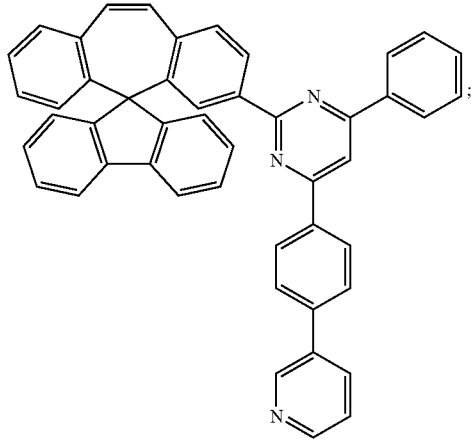
Compound 99
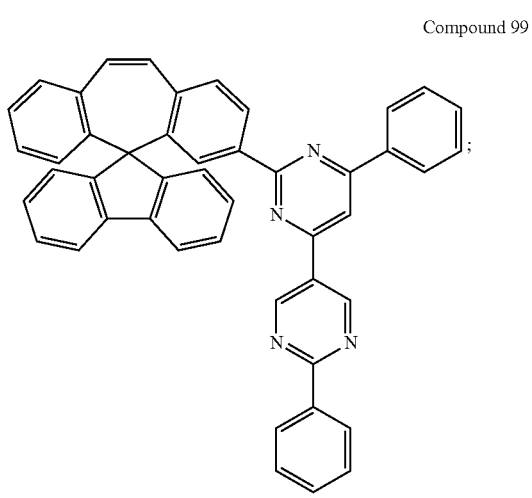
Compound 100
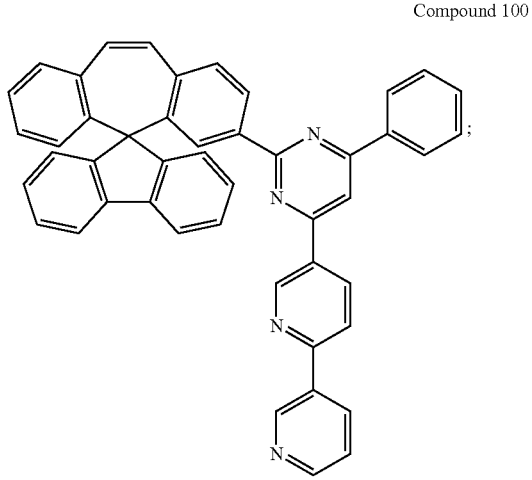

Compound 101
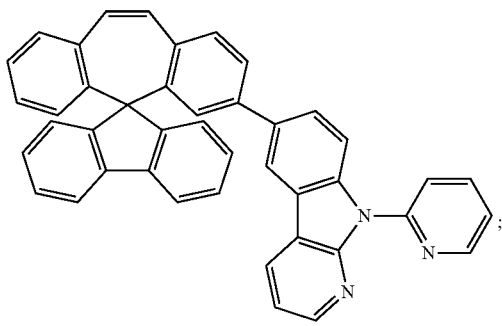
Compound 102
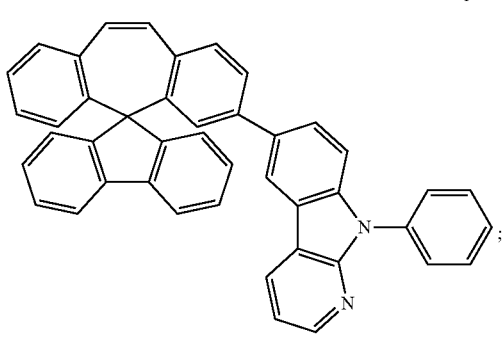
Compound 103
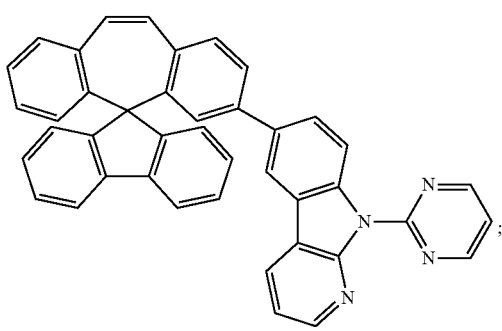
Compound 104
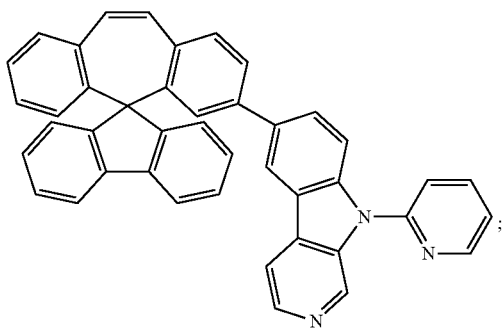
Compound 105
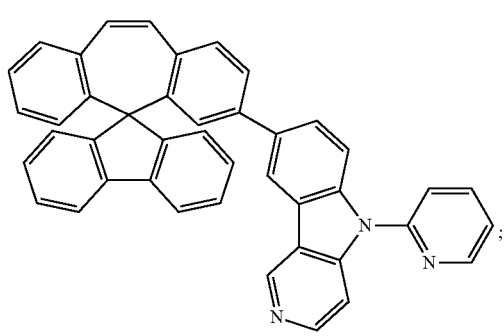
Compound 106
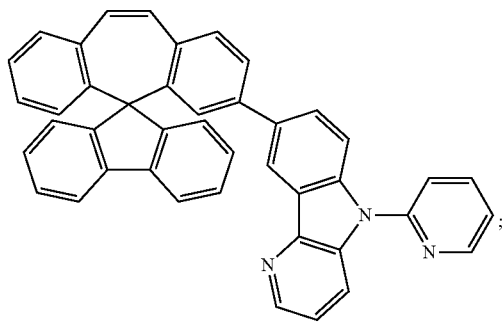
Compound 107
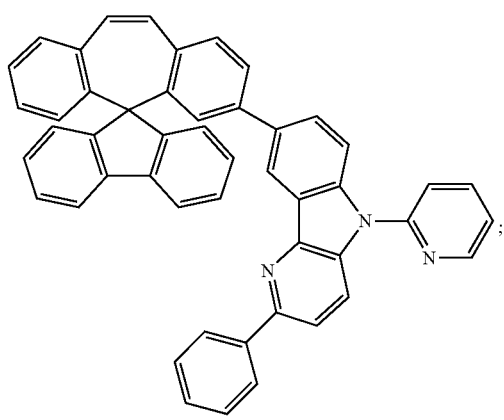
Compound 108
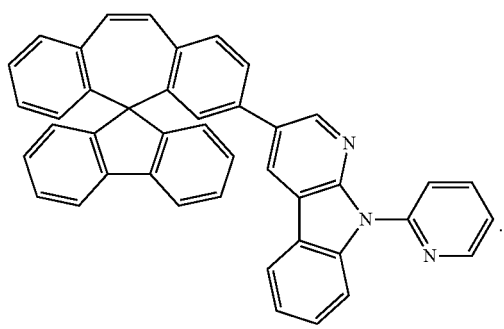
Or, the compound may contain a specific group ($L^2$-$G^2$) attached on the upper part of the main skeletal structure and another specific group ($L^1$-$G^1$), attached on the lower part of the main skeletal structure, such as:

Compound 23
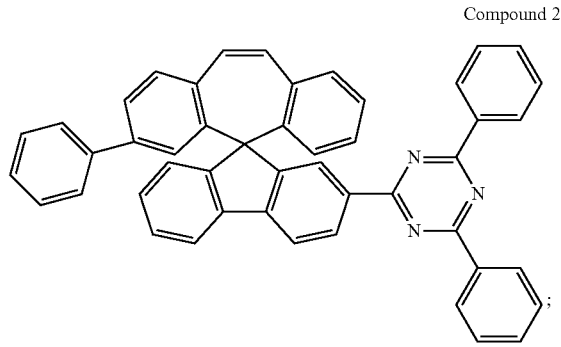
Compound 25
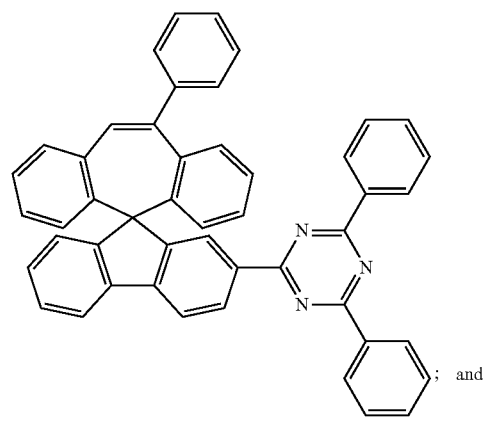
; and
Compound 24
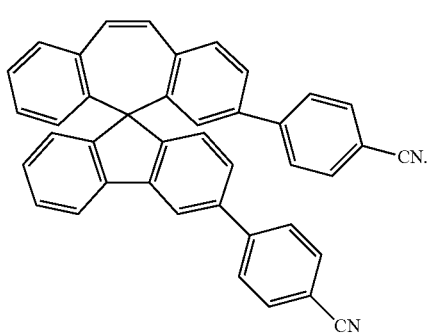
Compound 32
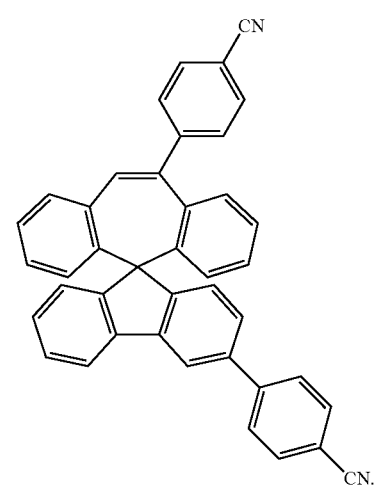
On the other hand, the compound may contain the specific group ($L^1$-$G^1$) attached on the lower part of the main skeletal structures and Y group, such as:
Compound 15
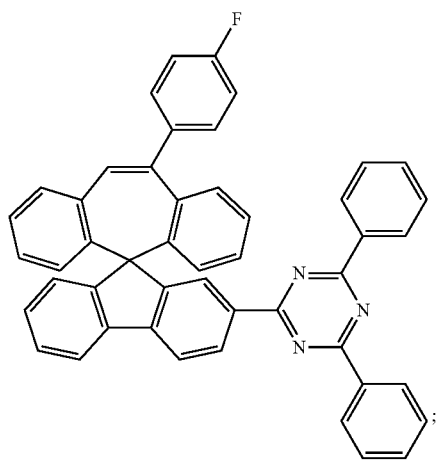
On the other hand, the compound may contain the specific group ($L^1$-$G^1$) attached on the lower part of the main skeletal structure and X group, such as:
Compound 27
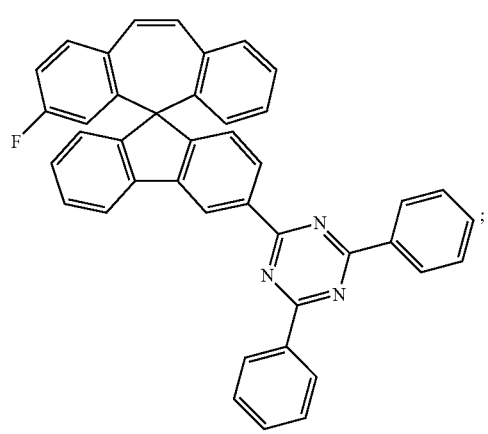
;

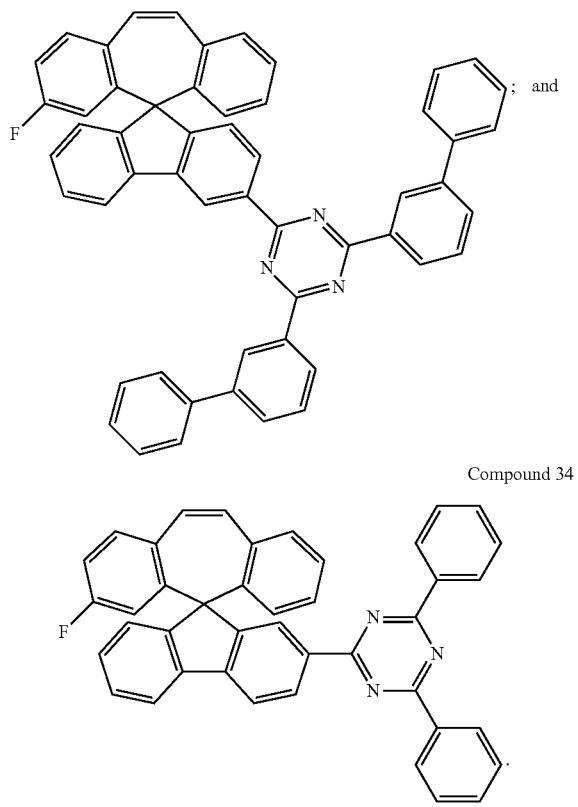

Compound 28

Compound 34

The present invention also provides an organic electronic device, comprising a first electrode, a second electrode, and an organic layer disposed between the first electrode and the second electrode. The organic layer comprises the novel compound as described above.

Preferably, the organic electronic device is an organic light emitting device (OLED). More preferably, the novel compound of the present invention may be used as an electron transport material or a hole blocking layer.

Specifically, the organic light emitting device may comprise:
a hole injection layer formed on the first electrode;
a hole transport layer formed on the hole injection layer;
an emission layer formed on the hole transport layer;
an electron transport layer formed on the emission layer;
an electron injection layer formed between the electron transport layer and the second electrode.

In one embodiment, the organic layer may be the electron transport layer, i.e., the electron transport layer comprises the novel compound as stated above.

Preferably, the hole injection layer may be a two-layered structure, i.e., the OLED comprises a first hole injection layer and a second hole injection layer disposed between the first electrode and the hole transport layer.

Preferably, the hole transport layer may be a two-layered structure, i.e., the OLED comprises a first hole transport layer and a second hole transport layer disposed between the two-layered hole injection layer and the emission layer.

Preferably, the electron transport layer is made of the novel compound. The OLEDs using the novel compound as the electron transport material can have an improved efficiency compared to commercial OLEDs using known electron transport material, such as 2-(4-(9,10-di(naphthalen-2-yl)anthracen-2-yl)phenyl)-1-phenyl-1H-benzo[d]imidazole; bis(2-methyl-8quinolinolato)(p-phenylphenolato)aluminum; and 2-(4-biphenylyl)-5-(4-tert-butylphenyl)-1,3,4-oxadiazole (PBD), as the electron transport material.

Preferably, the OLED comprises a hole blocking layer formed between the electron transport layer and the emission layer, to block holes overflow from the emission layer to the electron transport layer. Said hole blocking layer may be made of 2,9-dimethyl-4,7-diphenyl-1,10-phenanthroline (BCP) or 2,3,5,6-tetramethyl-phenyl-1,4-(bis-phthalimide) (TMPP), but not limited thereto. In further another embodiment, the organic layer may be the hole blocking layer, i.e., the hole blocking layer comprises the novel compound as stated above.

Preferably, the OLED comprises an electron blocking layer formed between the hole transport layer and the emission layer, to block electrons overflow from the emission layer to the hole transport layer. Said electron blocking layer may be made of 9,9'-[1,1'-biphenyl]-4,4'-diylbis-9H-carbazole (CBP) or 4,4',4"-tri(N-carbazolyl)-triphenylamine (TCTA), but not limited thereto.

In the presence of such a hole blocking layer and/or an electron blocking layer in an OLED, the OLED has a higher luminous efficiency compared to a typical OLED.

Said first and second hole transport layers may be made of, for example, but not limited to: $N^1,N^{1'}$-(biphenyl-4,4'-diyl)bis($N^1$-(naphthalen-1-yl)-$N^4,N^{4'}$-diphenylbenzene-1,4-diamine); or $N^4,N^{4'}$-di(naphthalen-1-yl)-$N^4,N^{4'}$-diphenylbiphenyl-4,4'-diamine (NPB).

Said first and second hole injection layer may be made of, for example, but not limited to, polyaniline, or polyethylenedioxythiophene.

Said emission layer can be made of an emission material including a host and a dopant. The host of the emission material is, for example, but not limited to, 9-(4-(naphthalen-1-yl)phenyl)-10-(naphthalen-2-yl)anthracene.

For red OLEDs, the dopant of the emission material is, for example, but not limited to: an organometallic compound of iridium (II) having perylene ligands, fluoranthene ligands, or periflanthene ligands. For green OLEDs, the dopant of the emission material is, for example, but not limited to: diaminofluorenes, diaminoanthracenes, or organometallic compounds of iridium (II) having phenylpyridine ligands. For blue OLEDs, the dopant of the emission material is, for example, but not limited to: diaminofluorenes, diaminoanthracenes, diaminopyrenes, or organicmetallic compounds of iridium (II) having phenylpyridine ligands. With various host materials of the emission layer, the OLED can emit lights in red, green or blue.

Said electron injection layer may be made of an electron injection material, for example, but not limited to (8-oxidonaphthalen-1-yl)lithium(II).

Said first electrode is, for example, but not limited to, an indium-doped tin oxide electrode.

Said second electrode has a work function lower than that of the first electrode. The second electrode is, for example, but not limited to, an aluminum electrode, an indium electrode, or a magnesium electrode.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
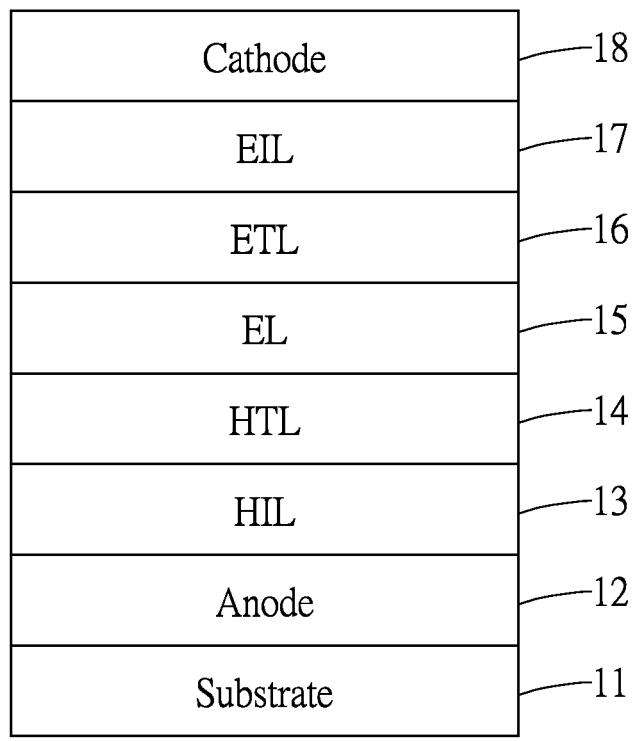
FIG. 1 illustrates a schematic cross-sectional view of an OLED.
Figure 2:
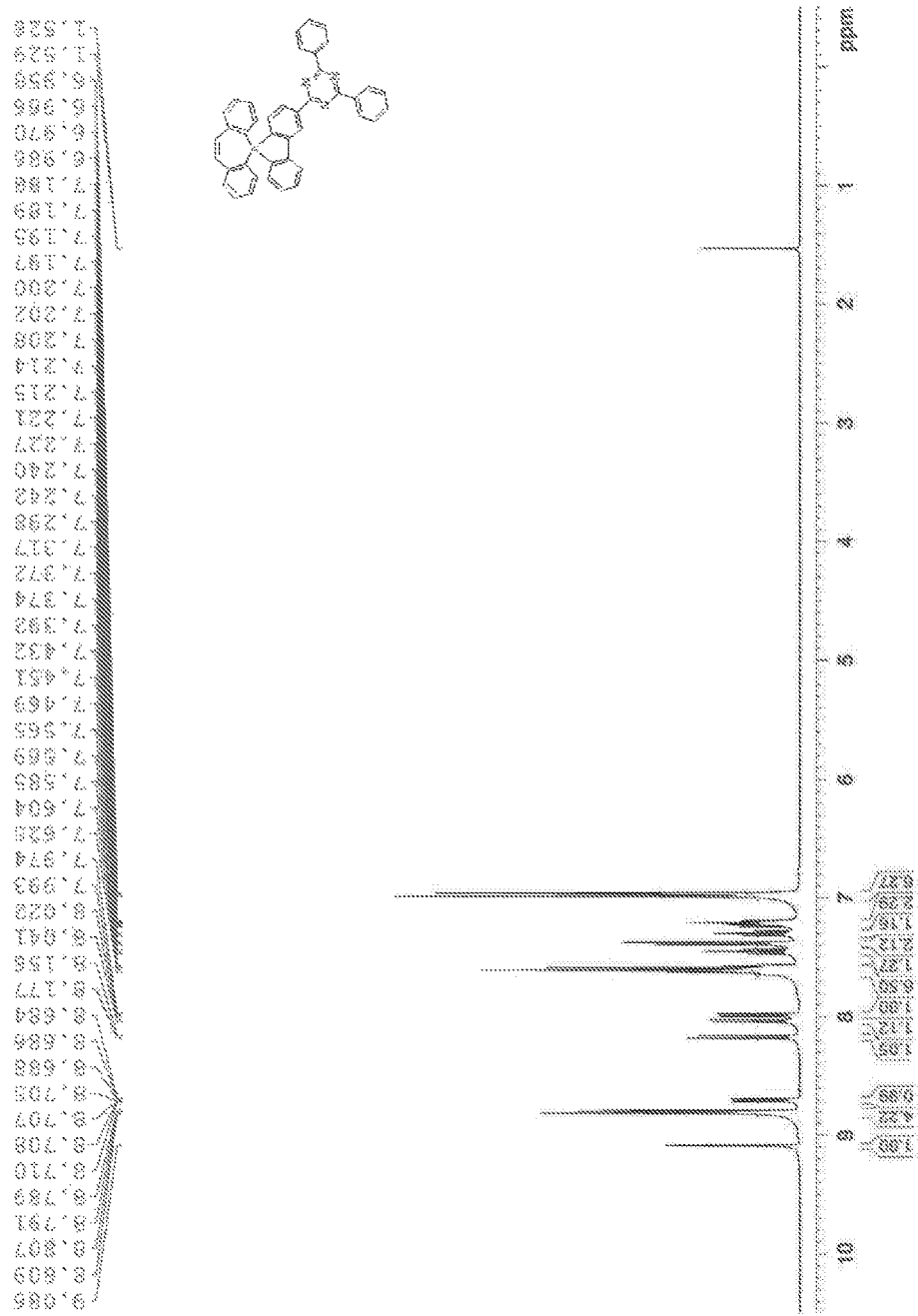
FIGS. 2 to 26 respectively are $^1$H nuclear magnetic resonance (NMR) spectrum of compounds 1 to 8, 13, 14, 17 to 20, 25 to 31 and the compounds used in Comparative Examples 1 to 4.
Figure 3:
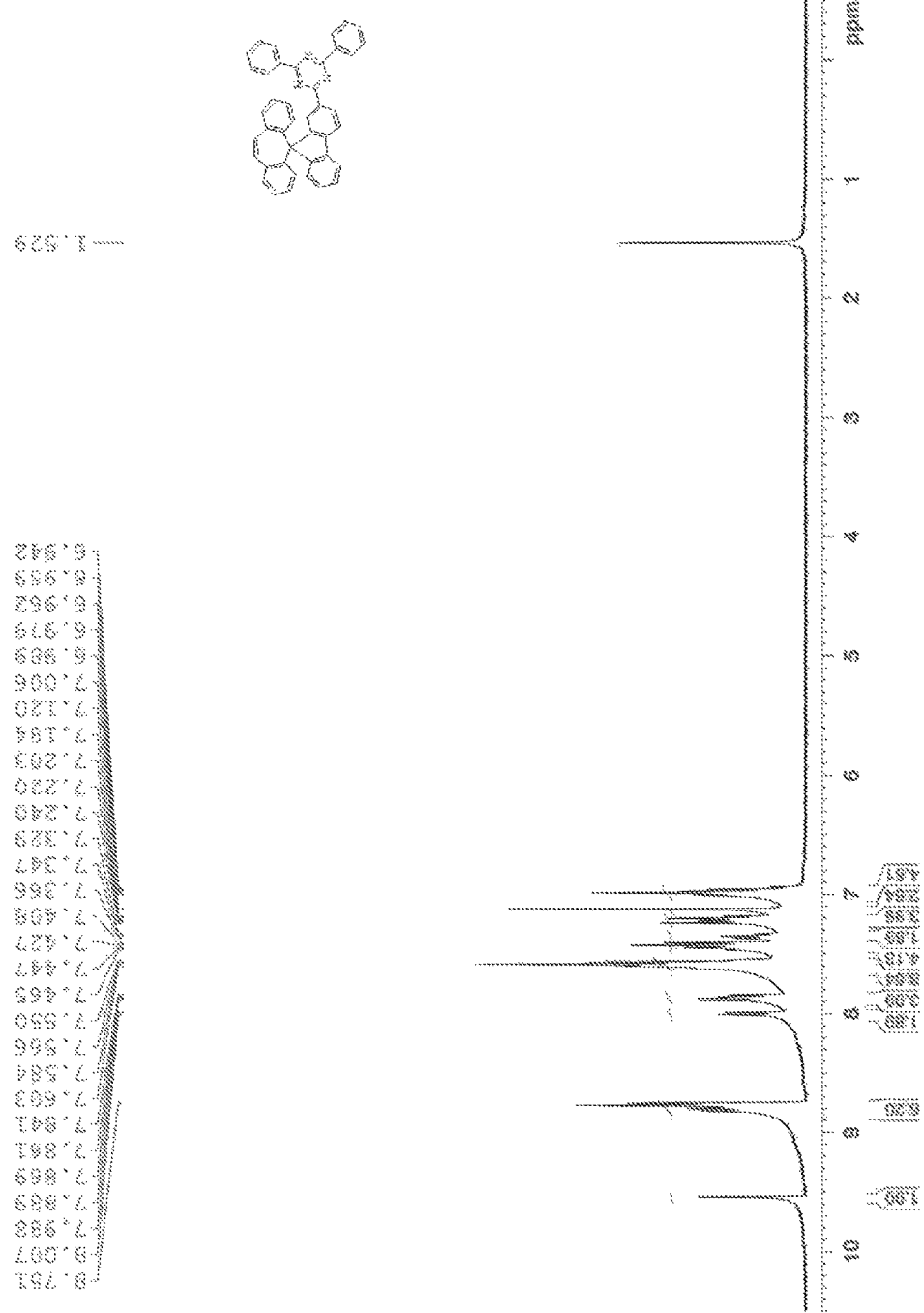
Figure 4:
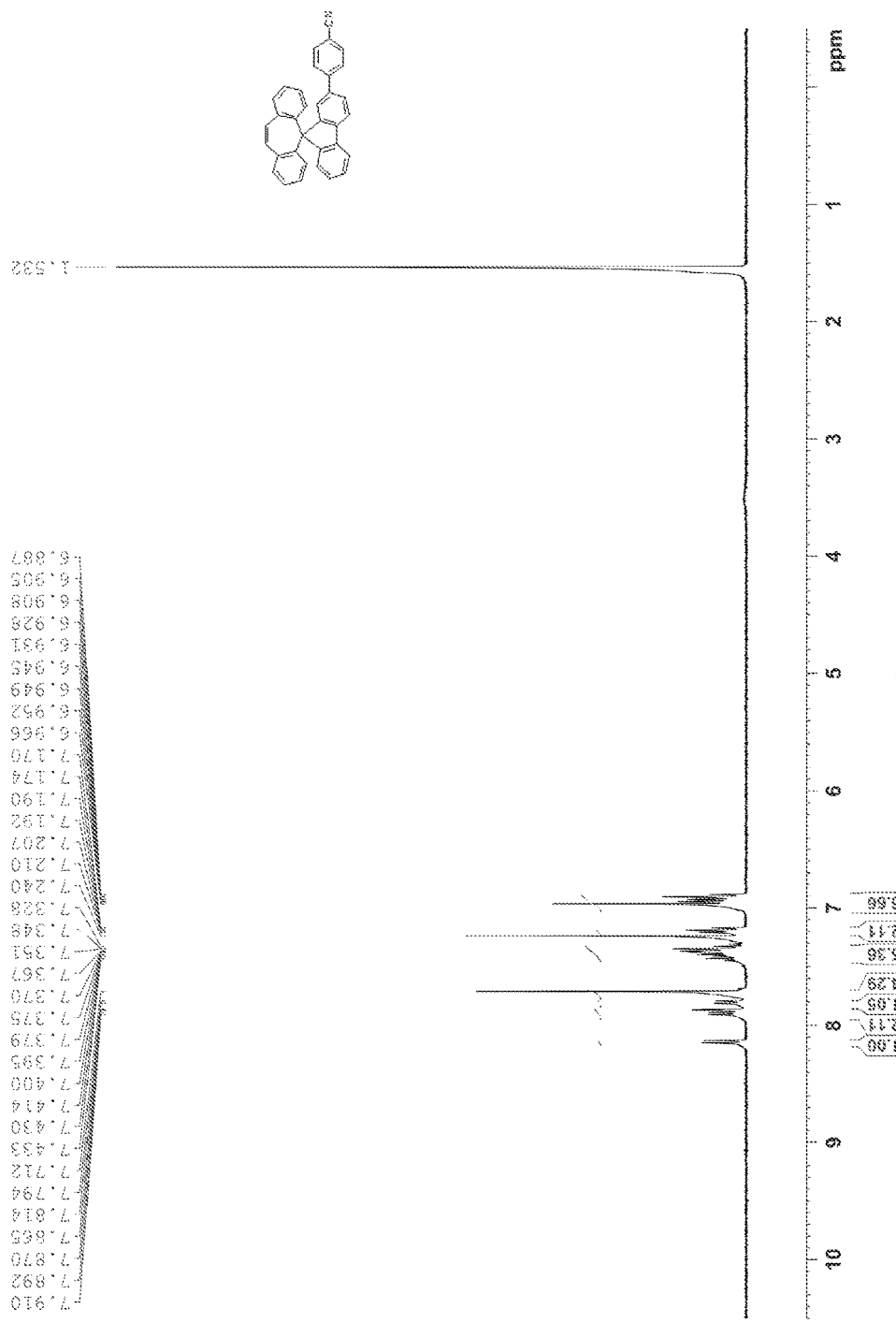
Figure 5:
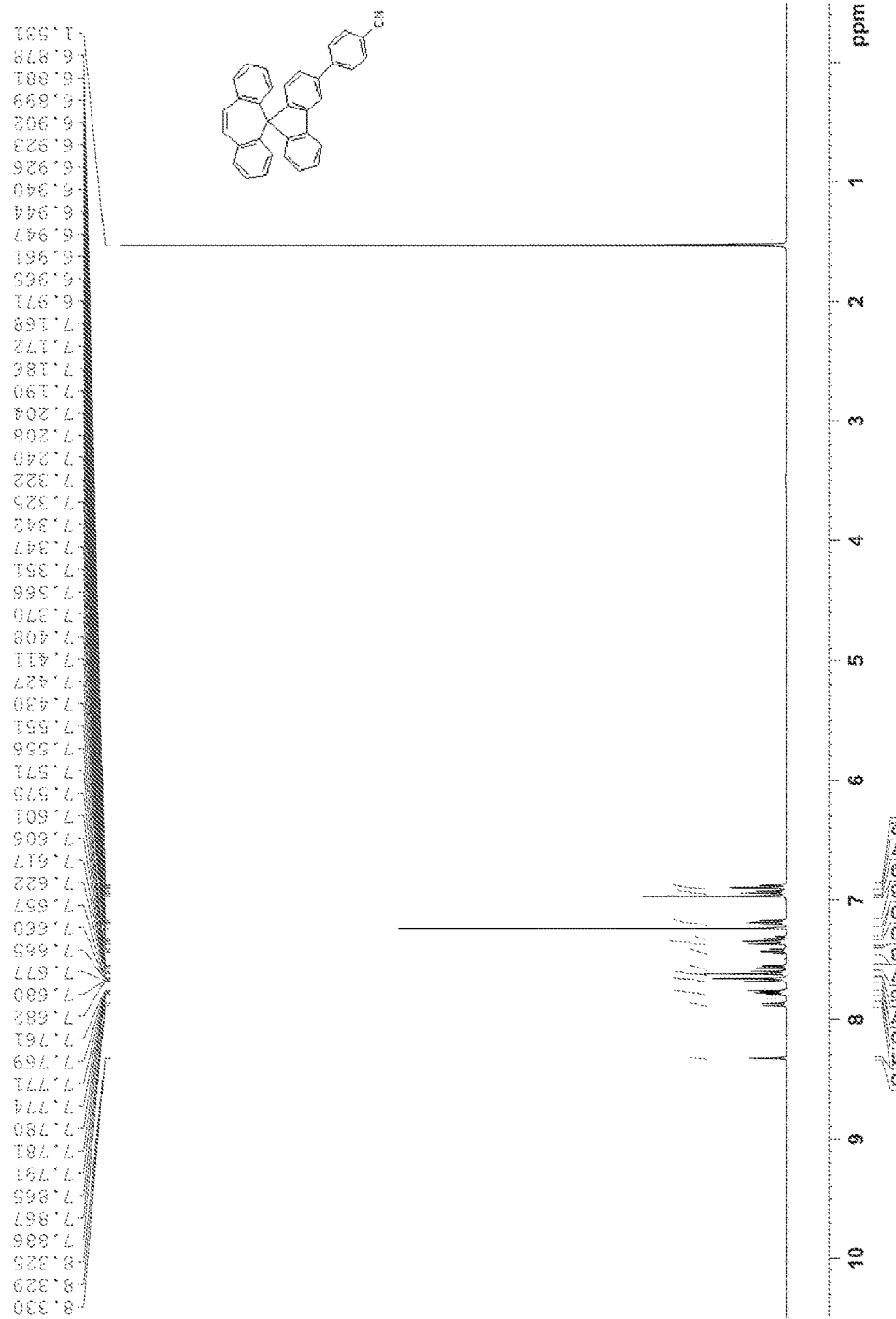
Figure 6:
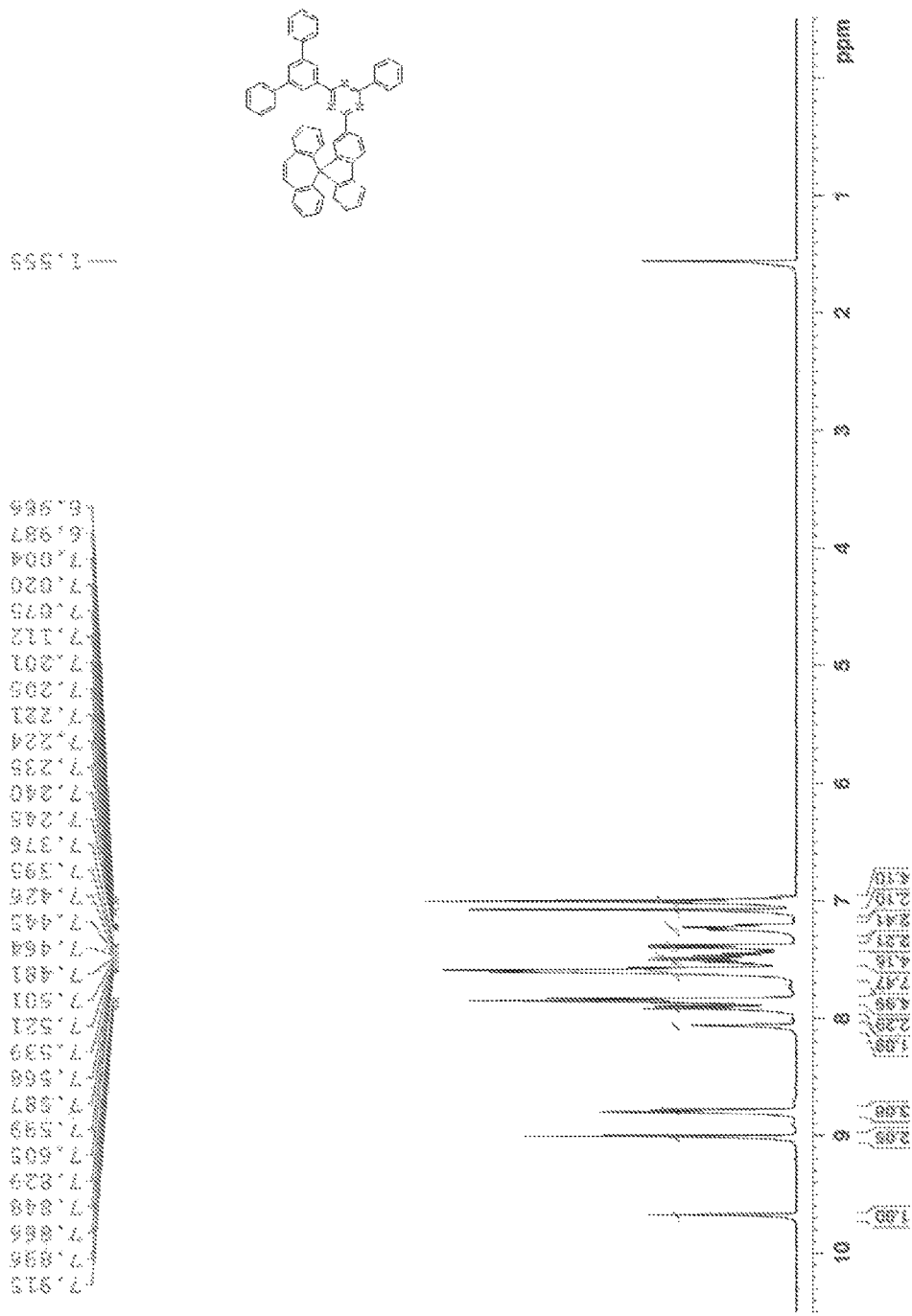
Figure 7:
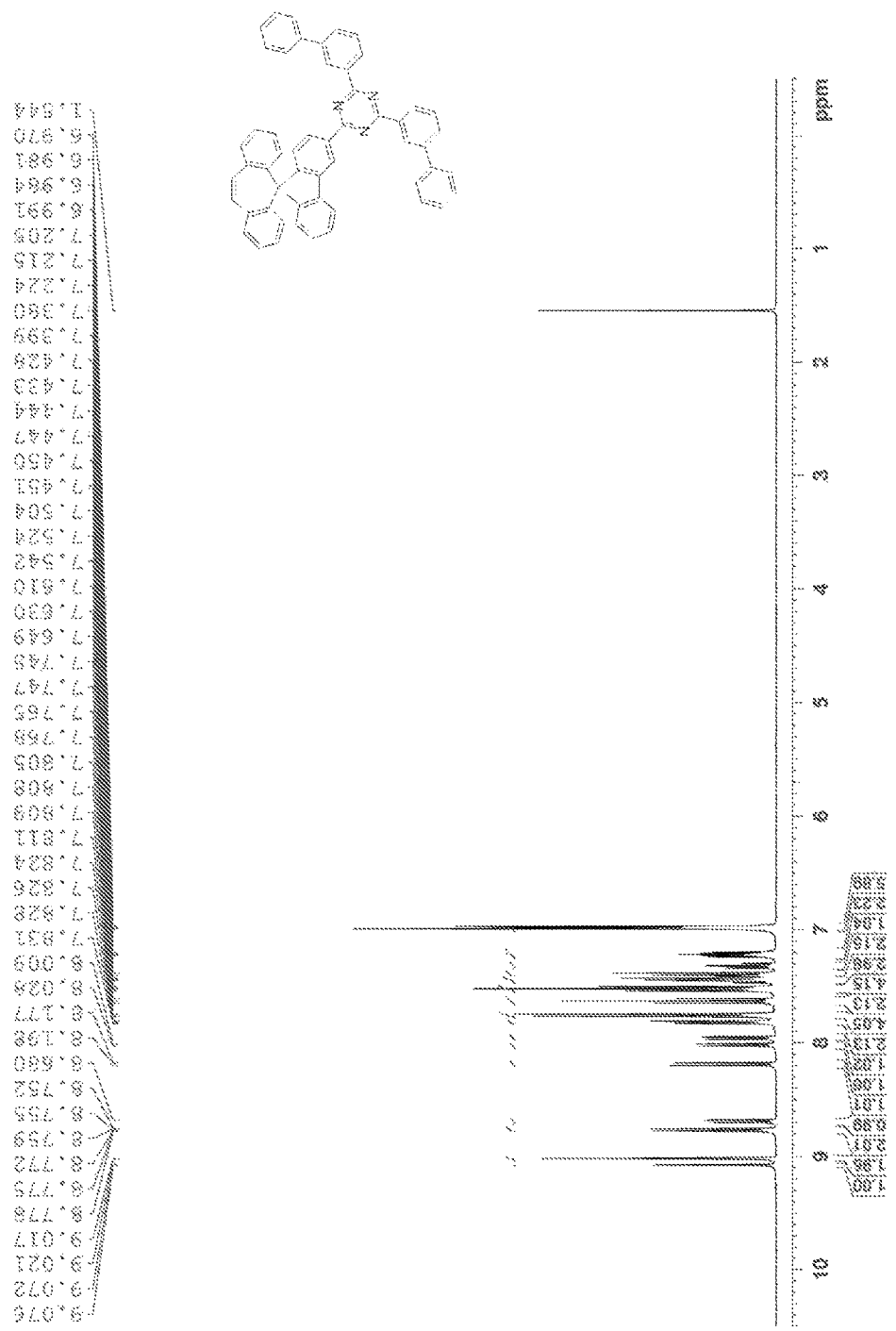
Figure 8:
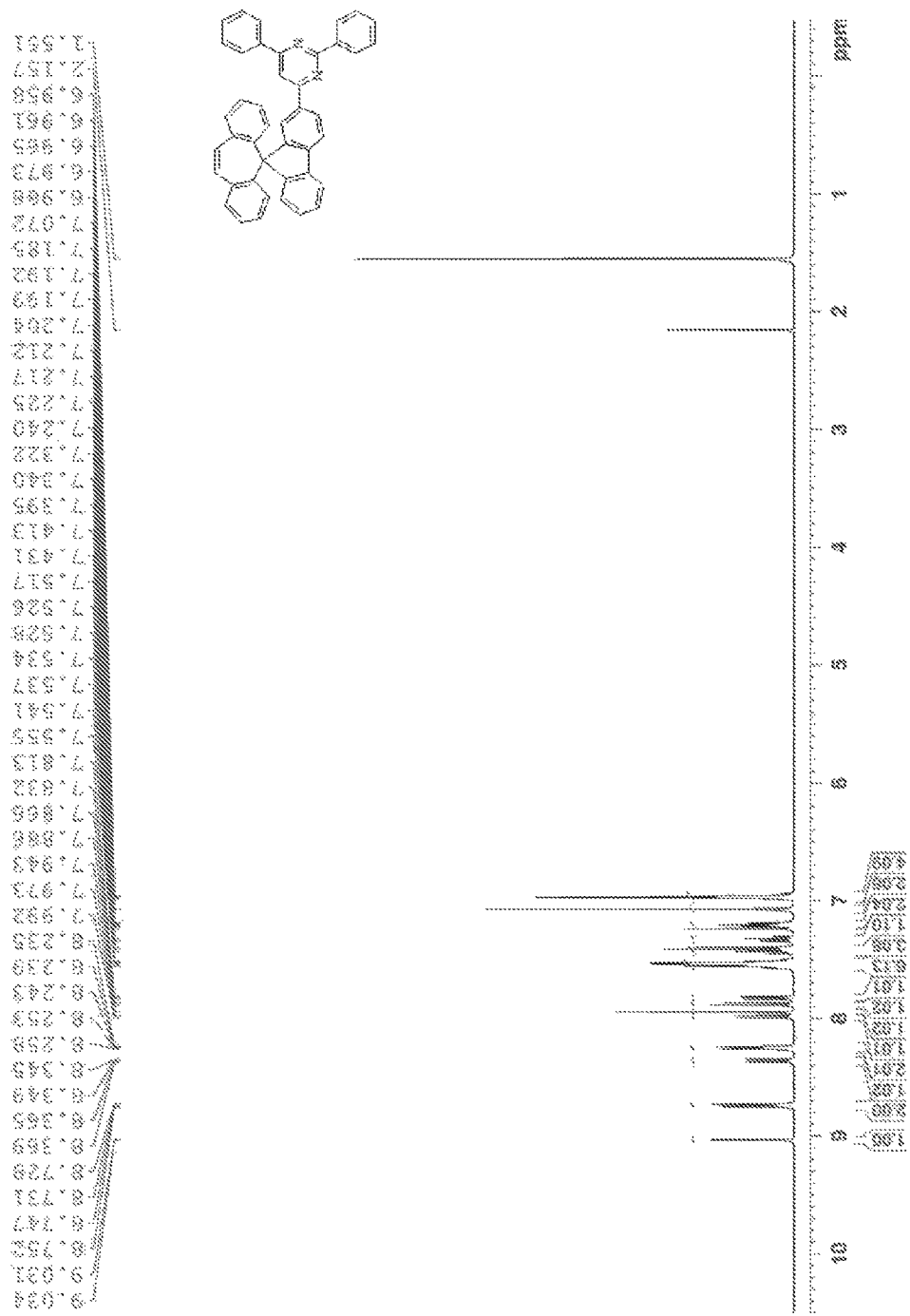
Figure 9:
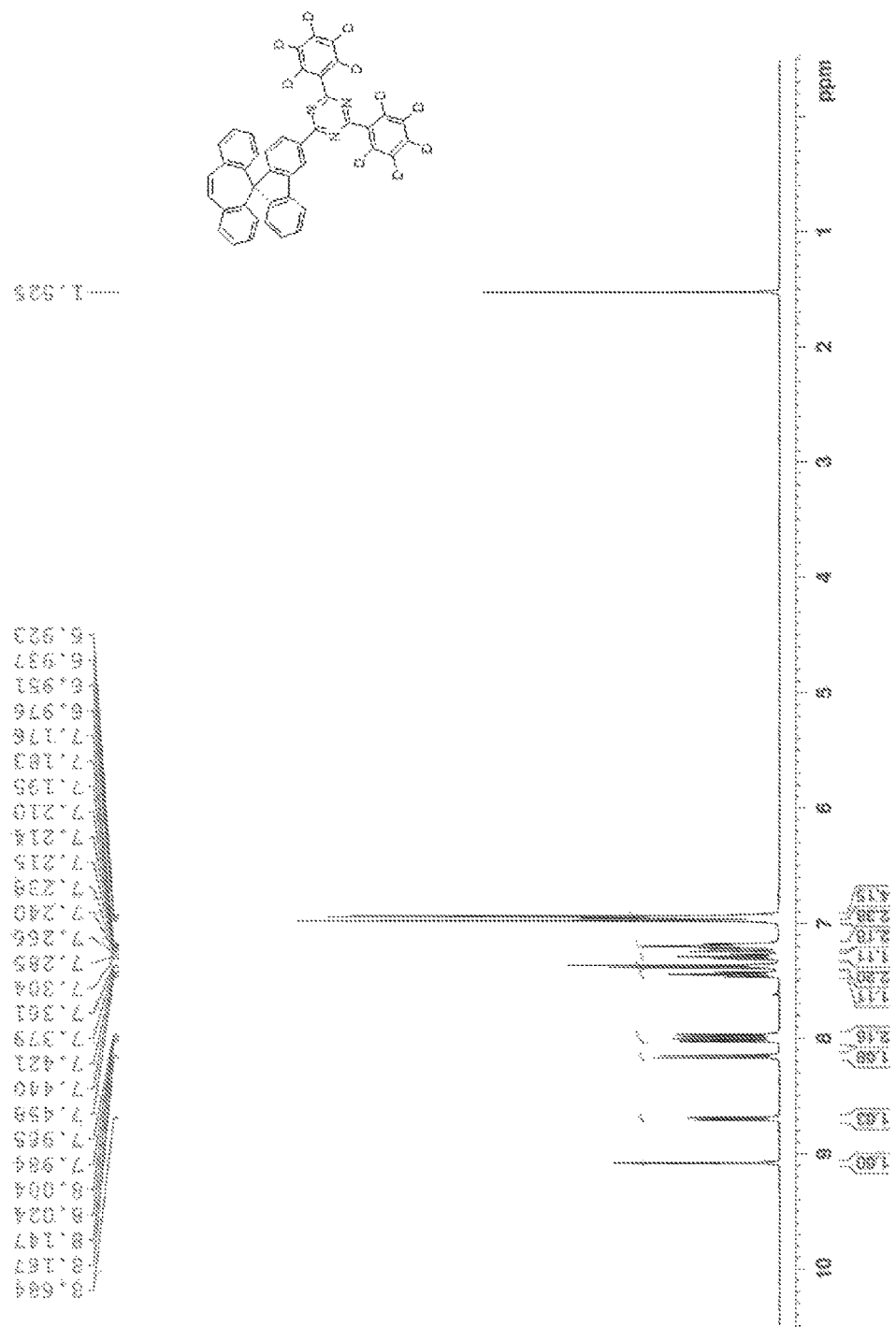
Figure 10:
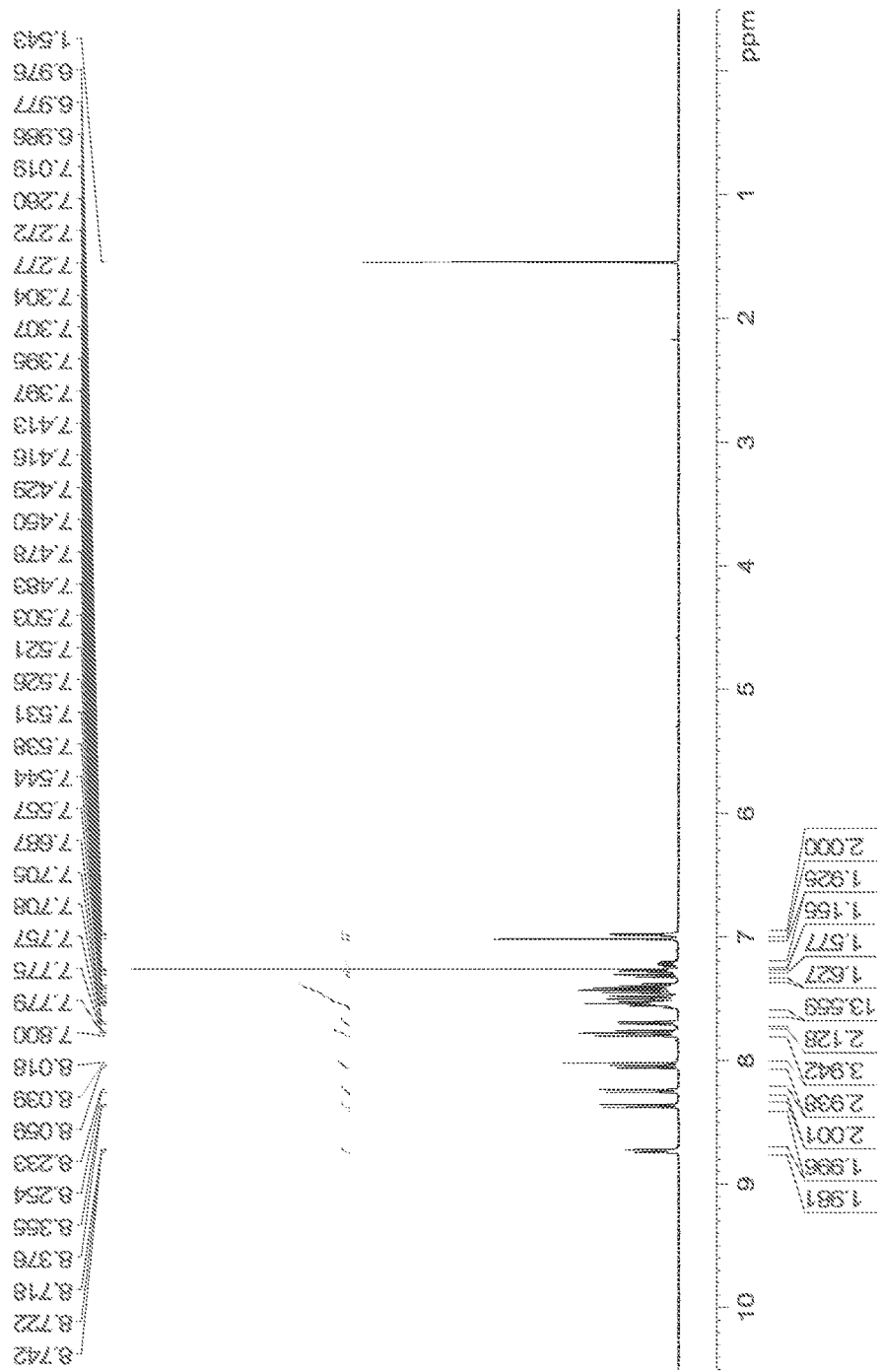
Figure 11:
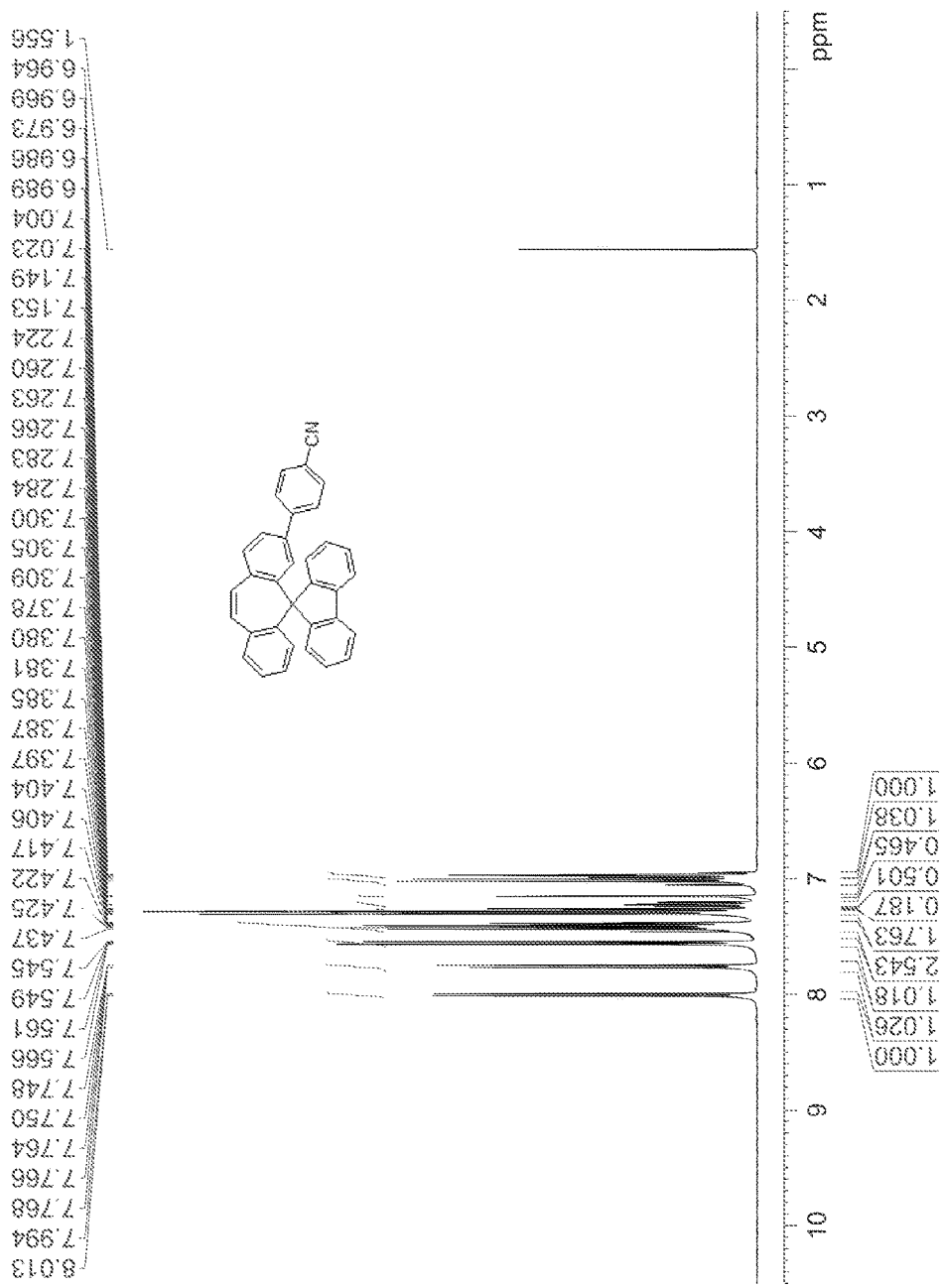
Figure 12:
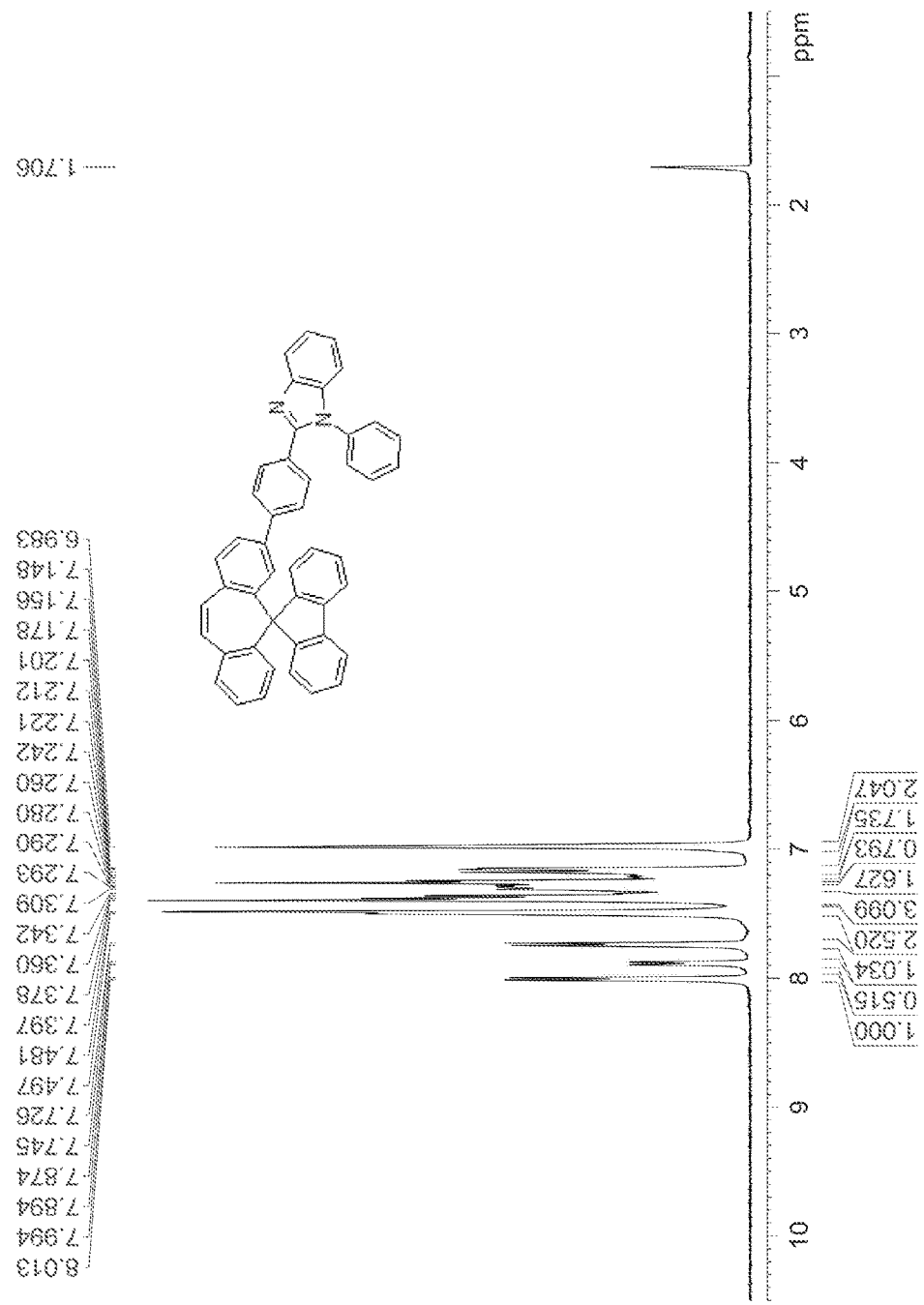
Figure 13:
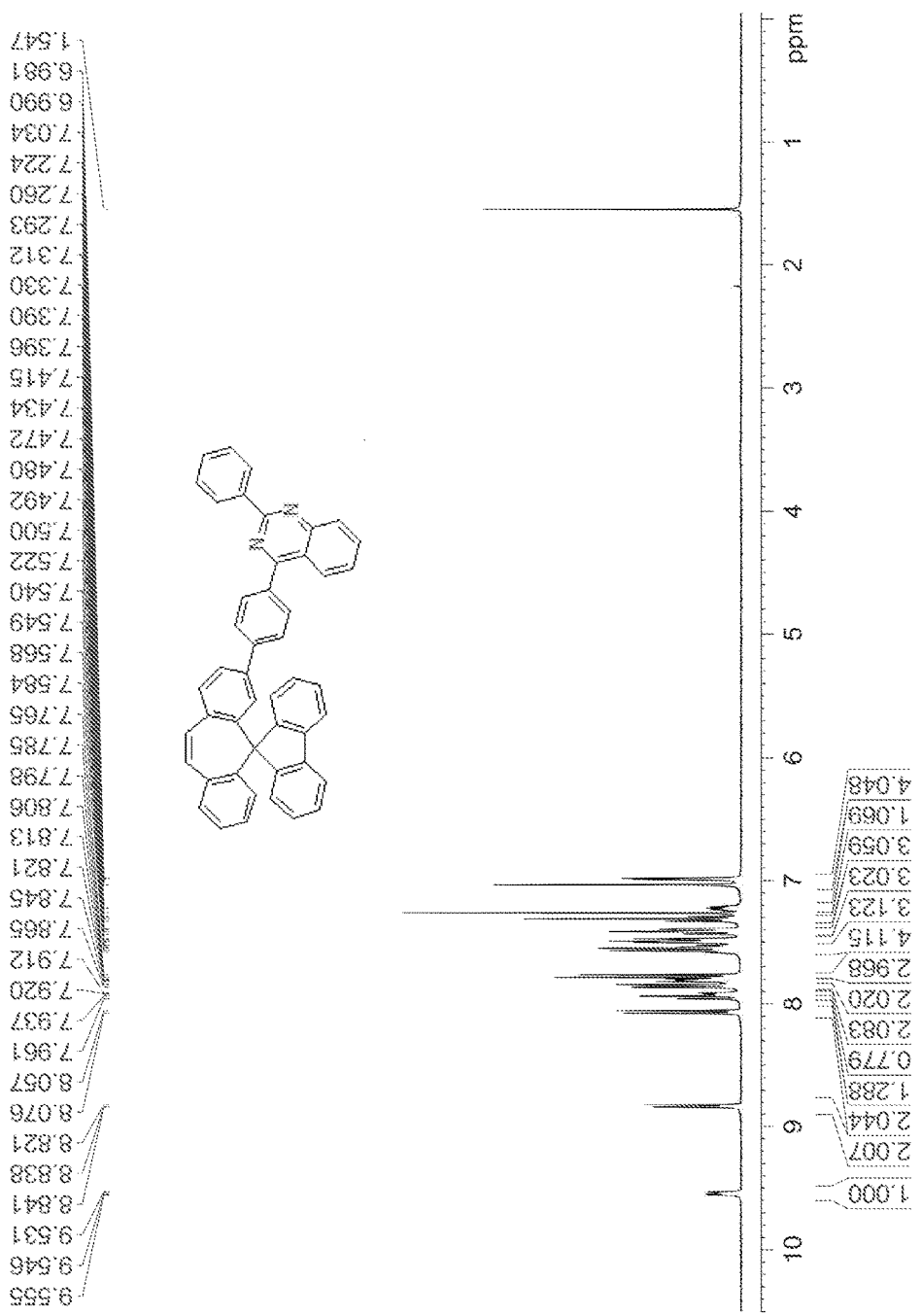
Figure 14:
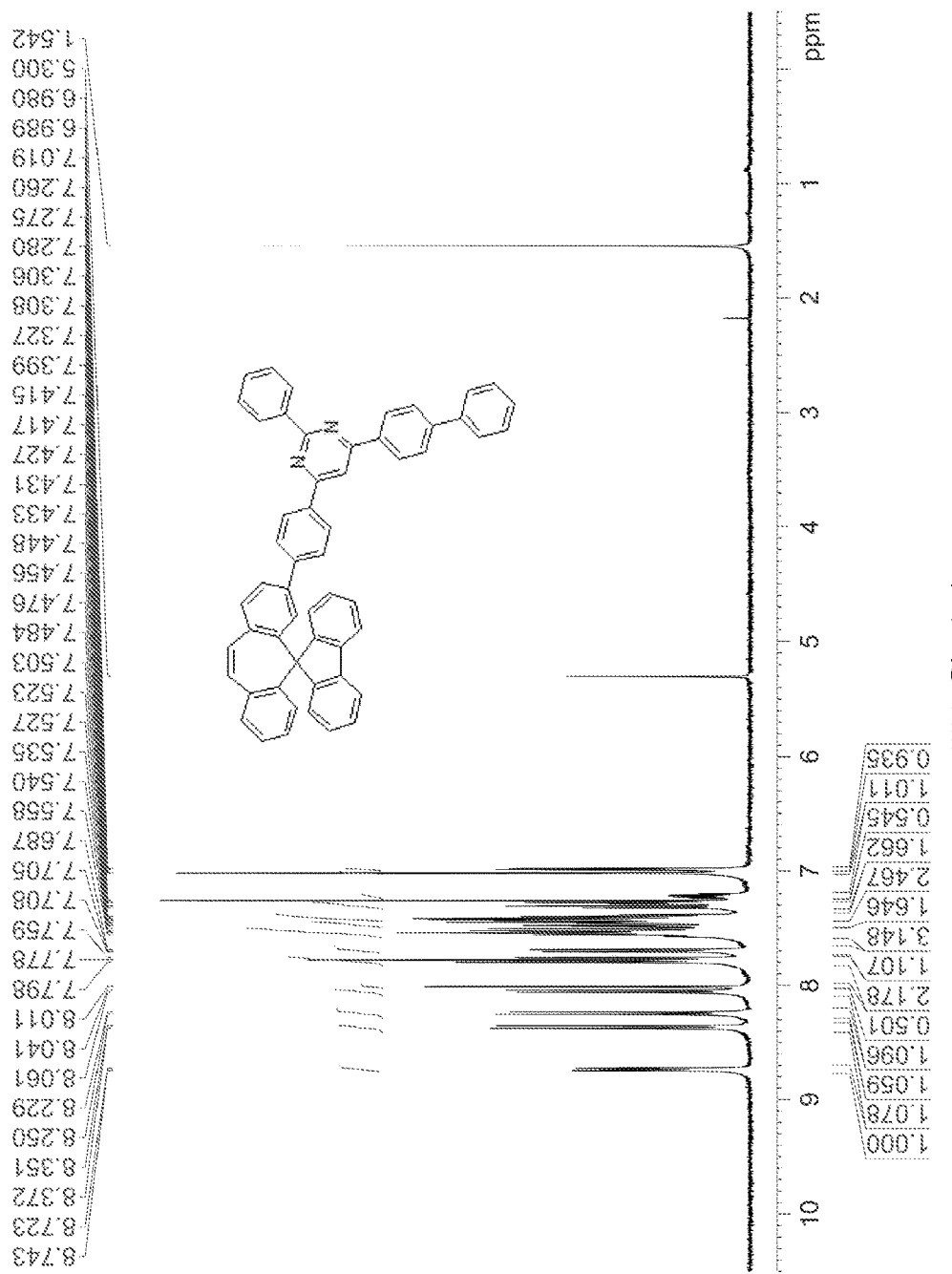
Figure 15:
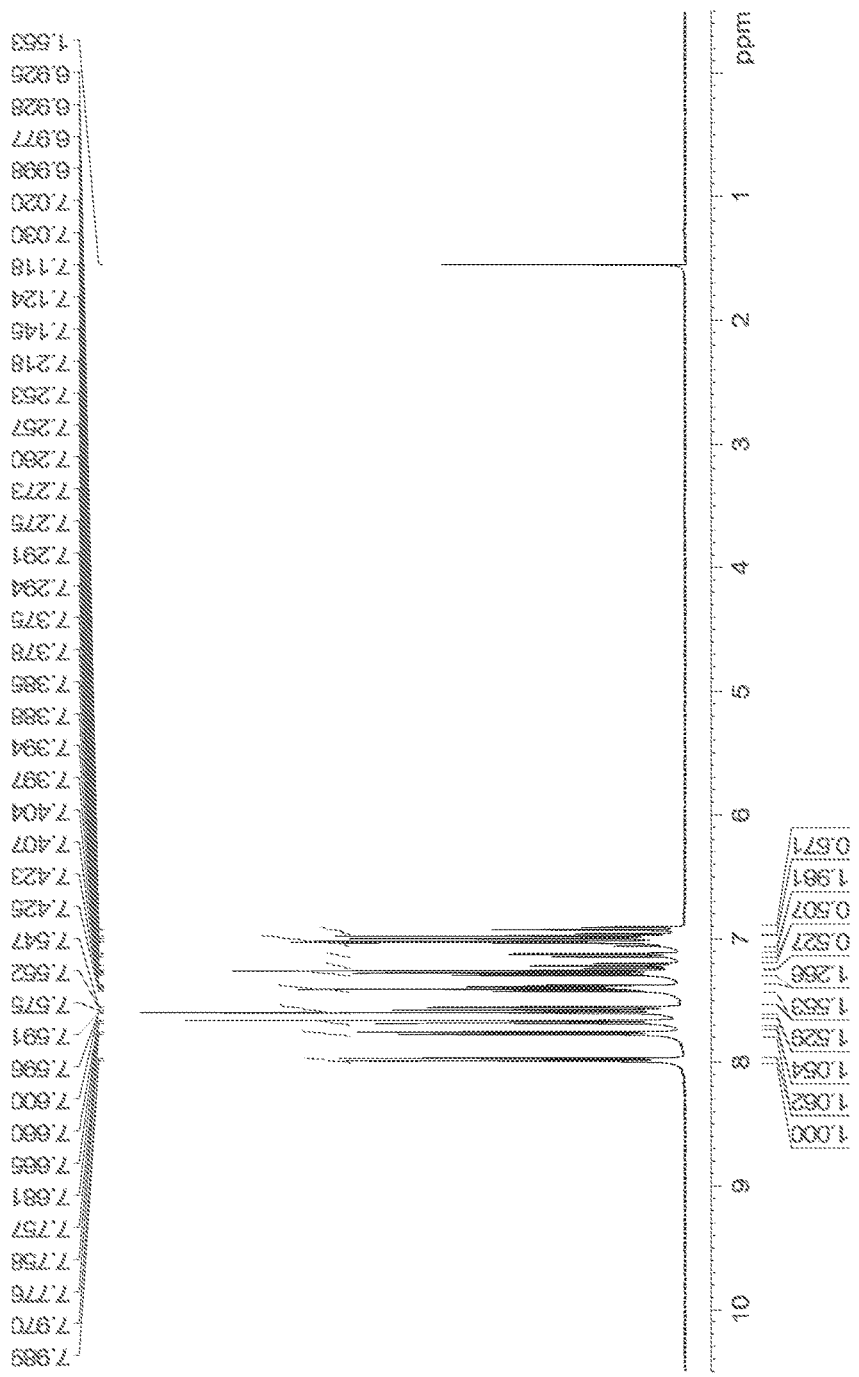
Figure 16:
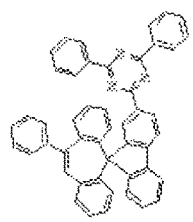
Figure 16:
Figure 16:
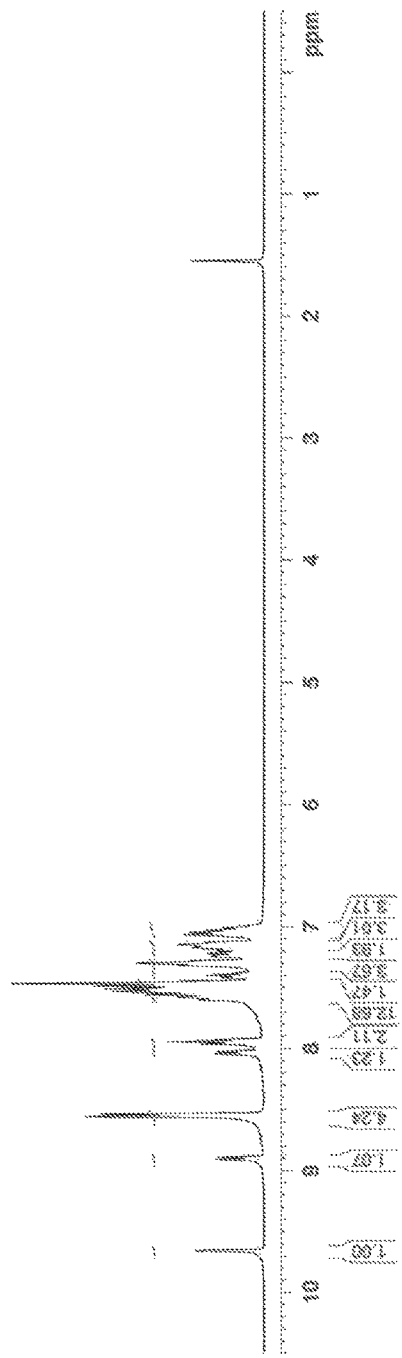
Figure 17:
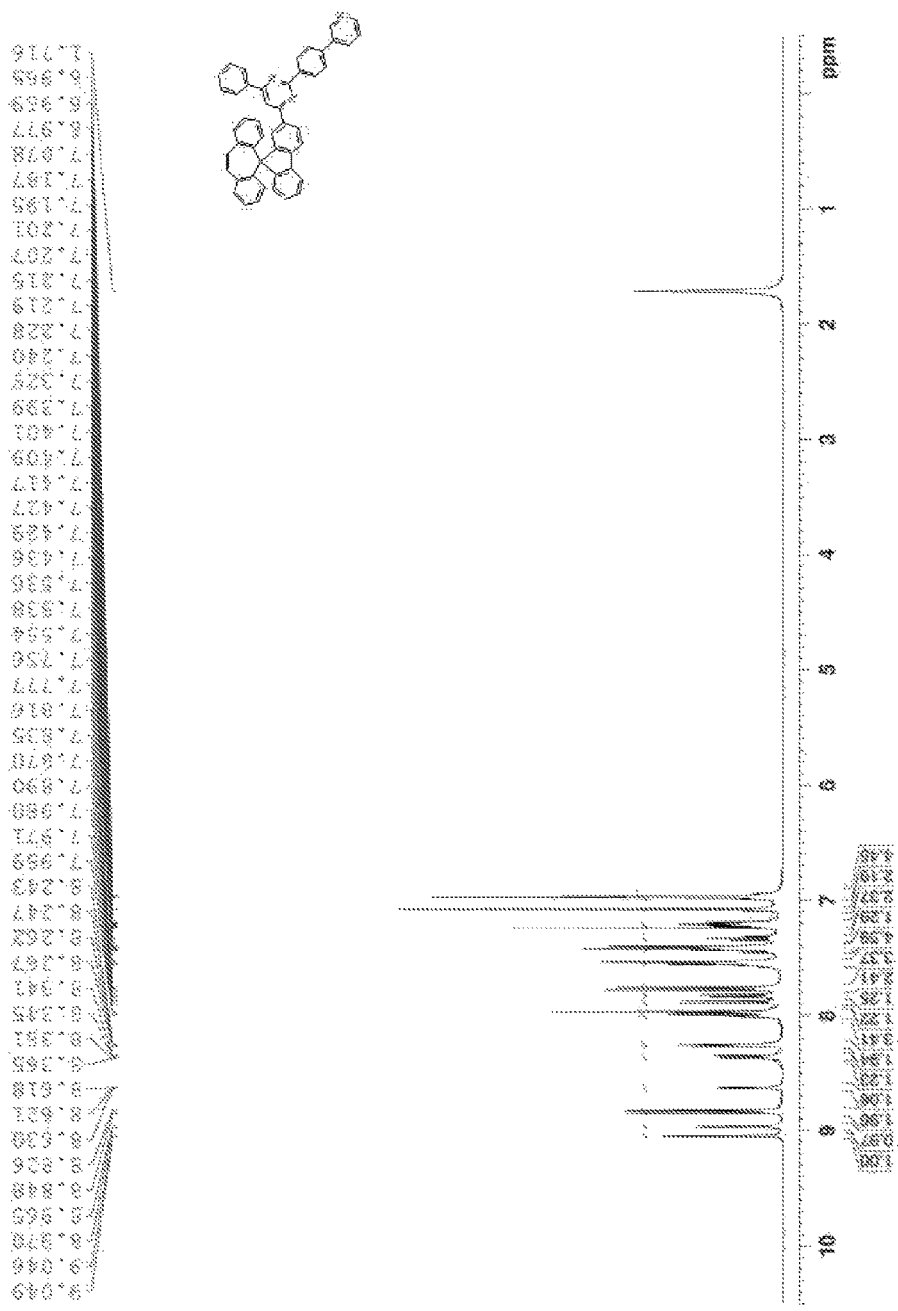
Figure 18:
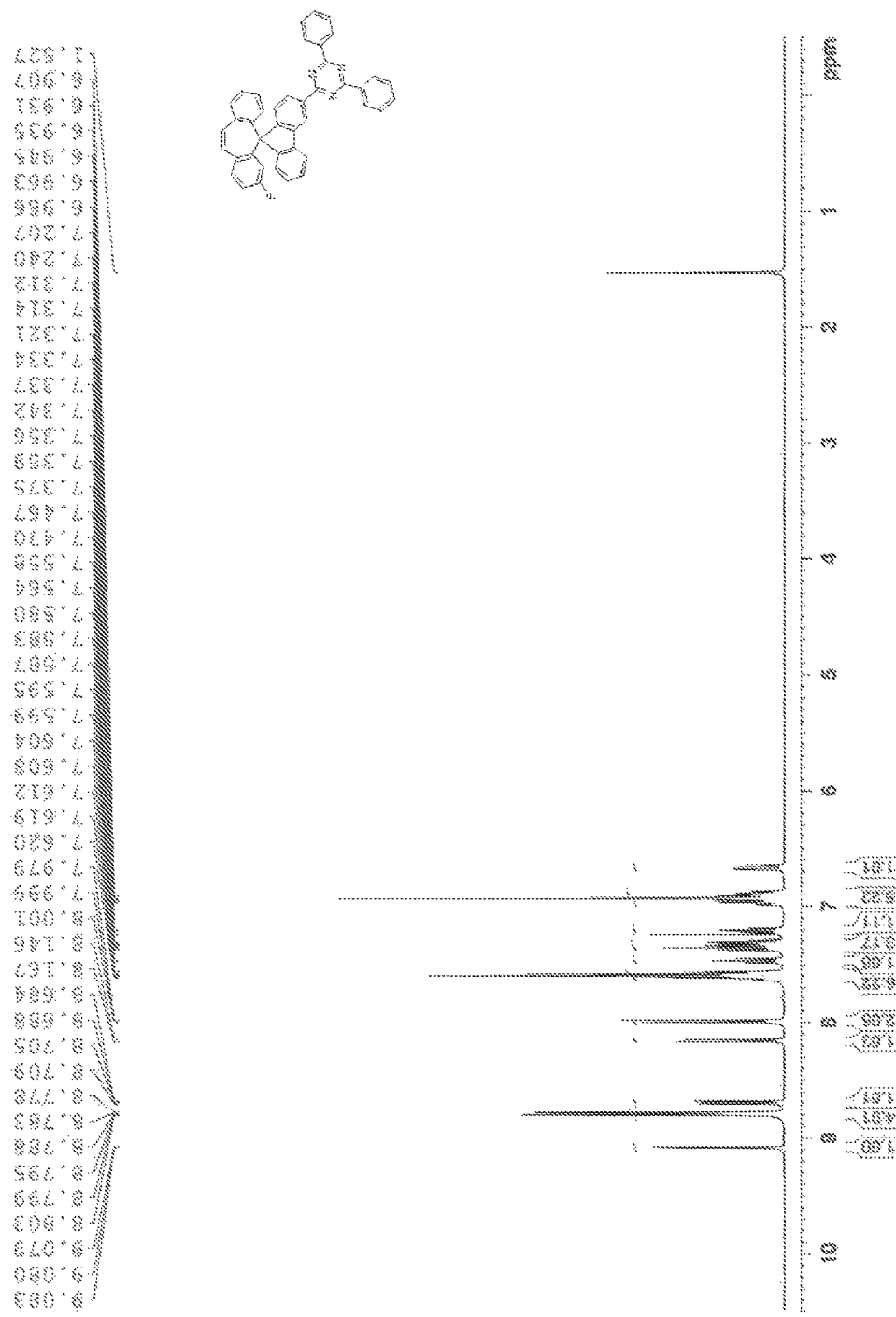
Figure 19:
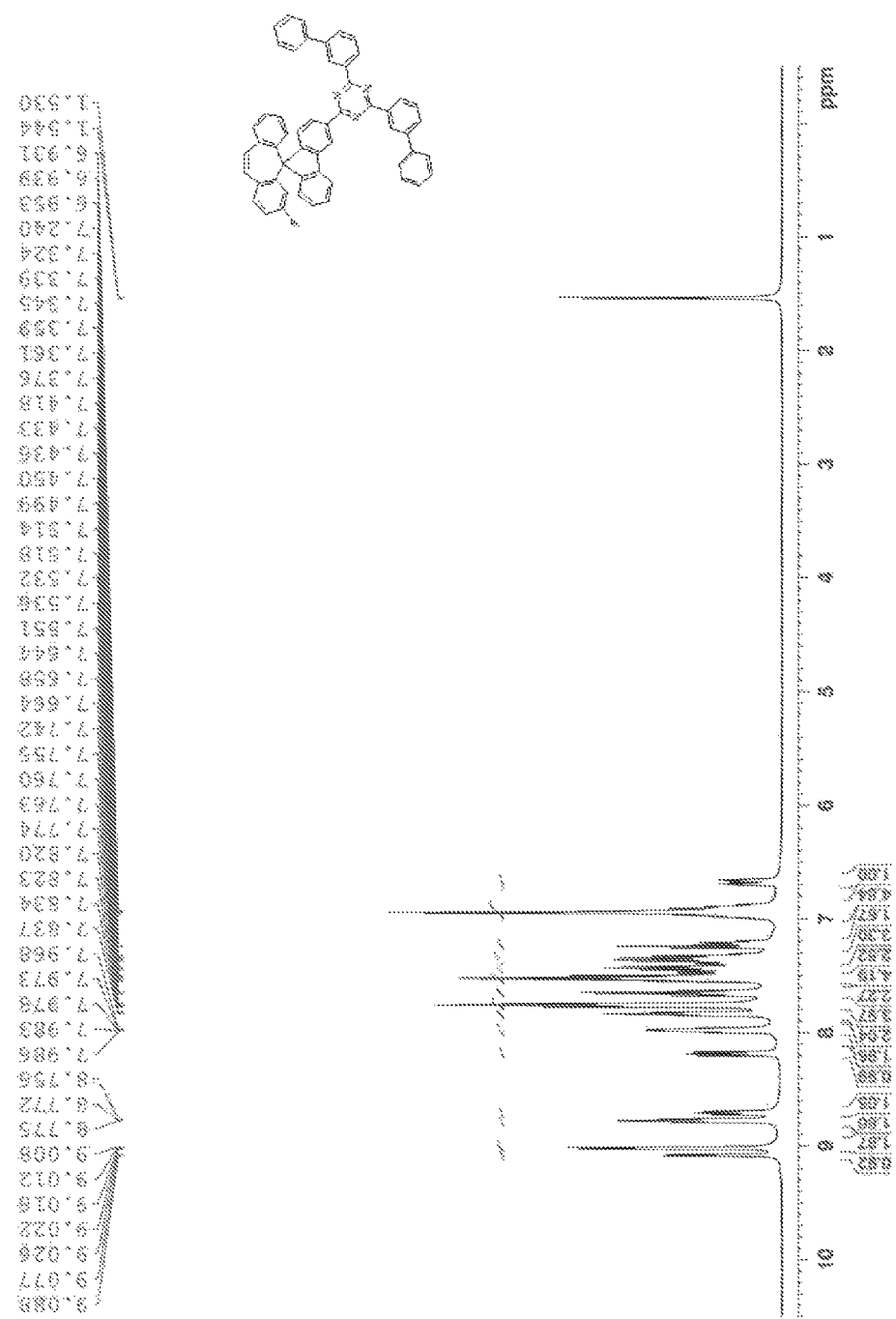
Figure 20:
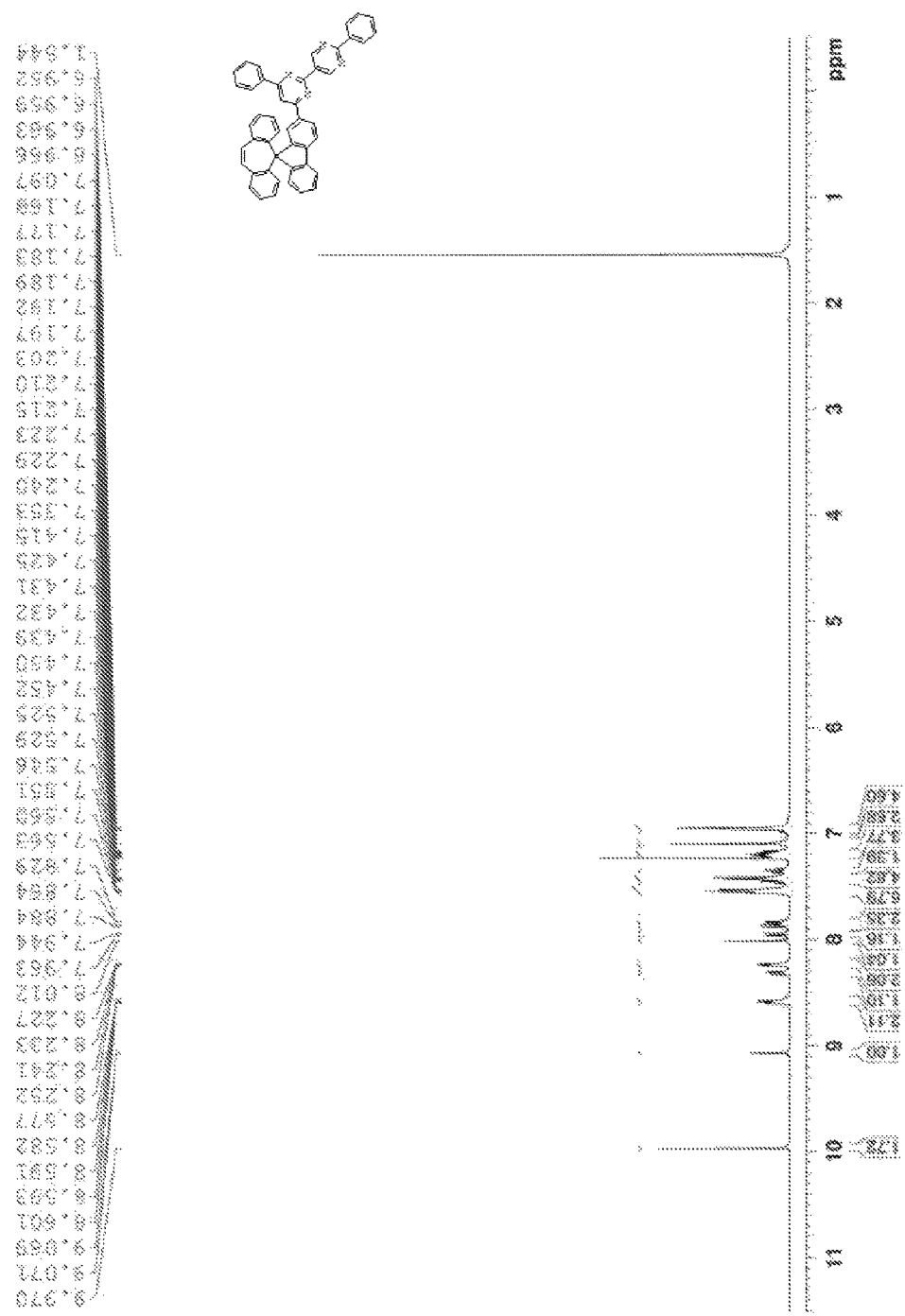
Figure 21:
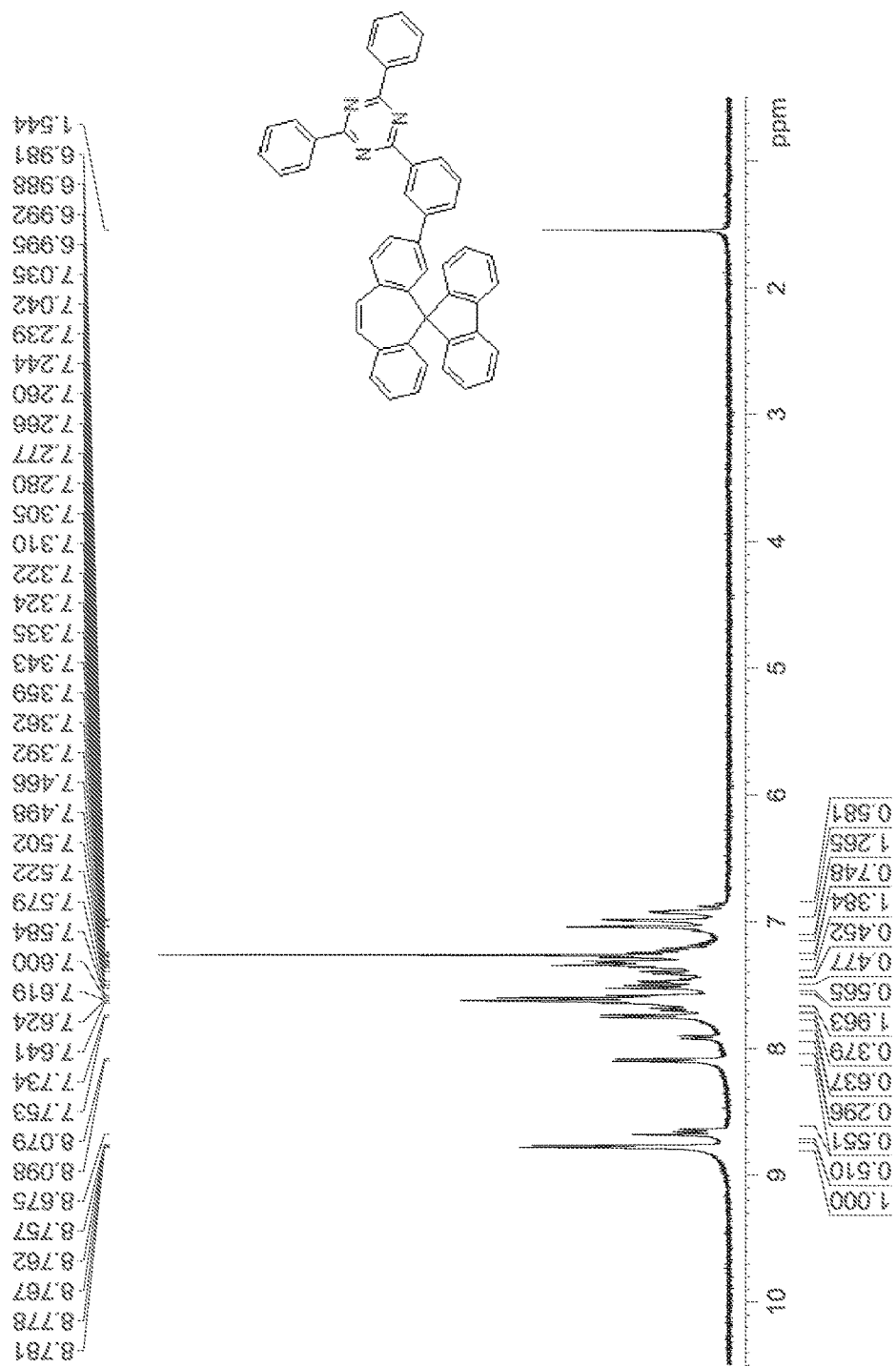
Figure 22:
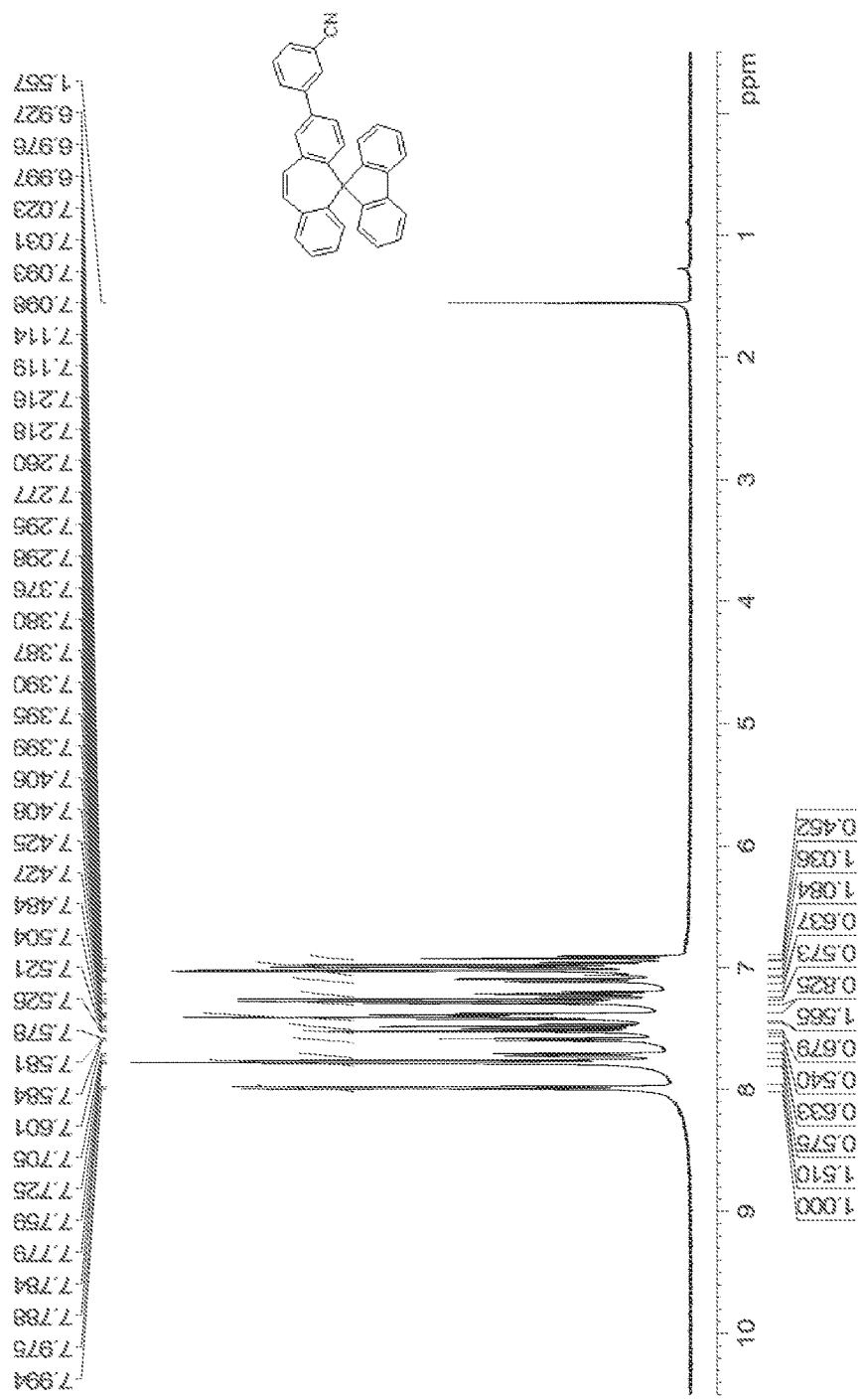
Figure 23:
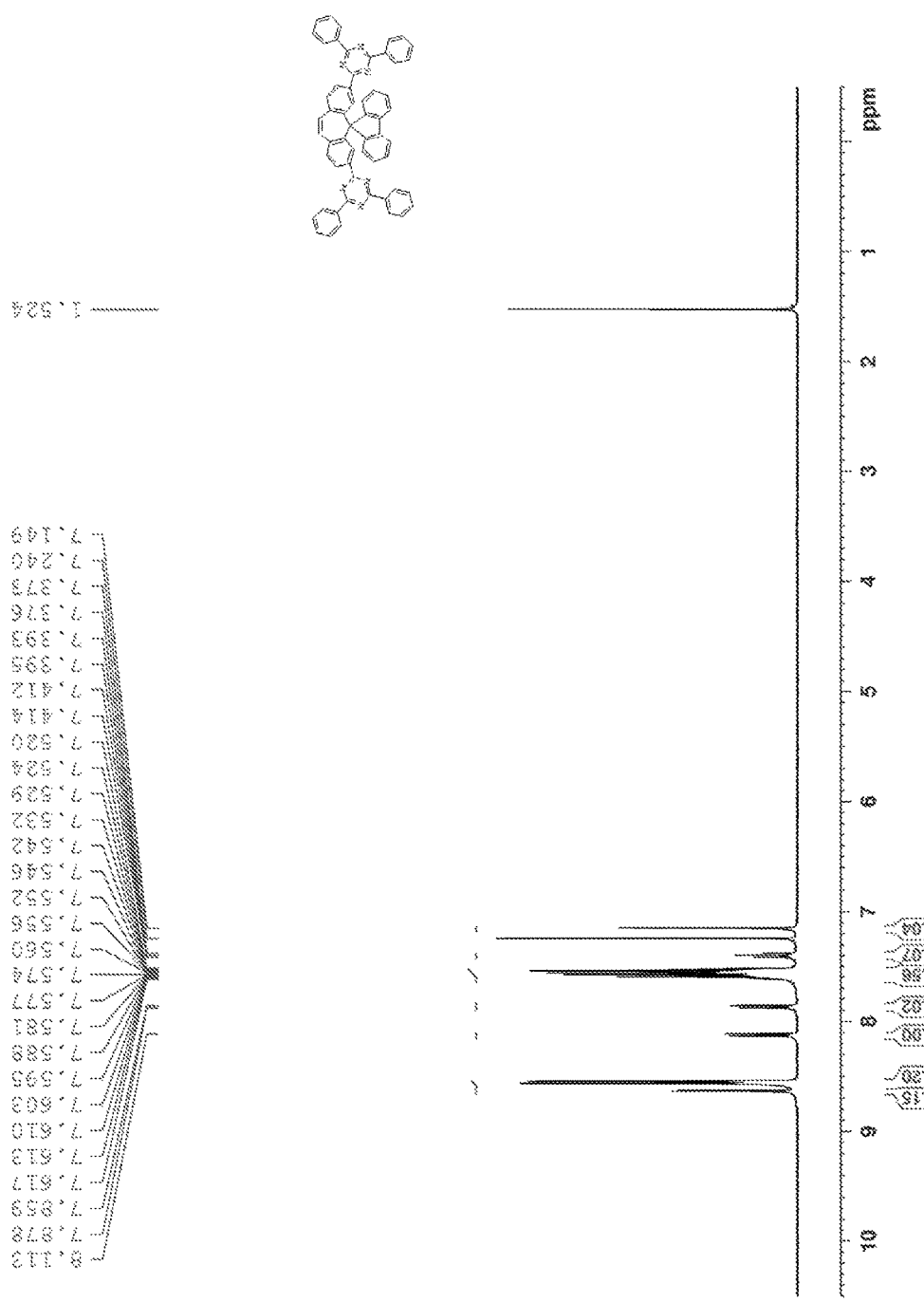
Figure 24:
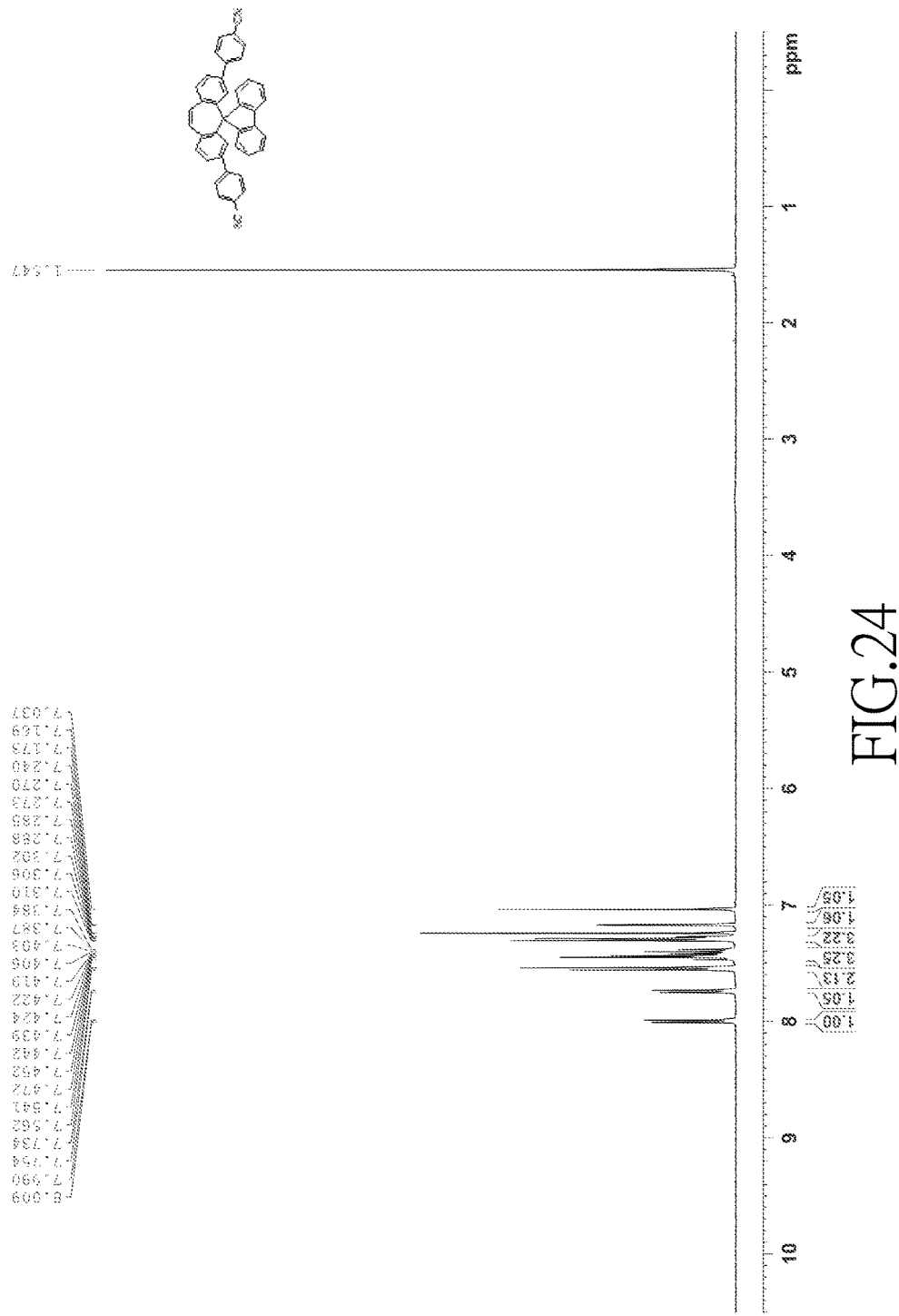
Figure 25:
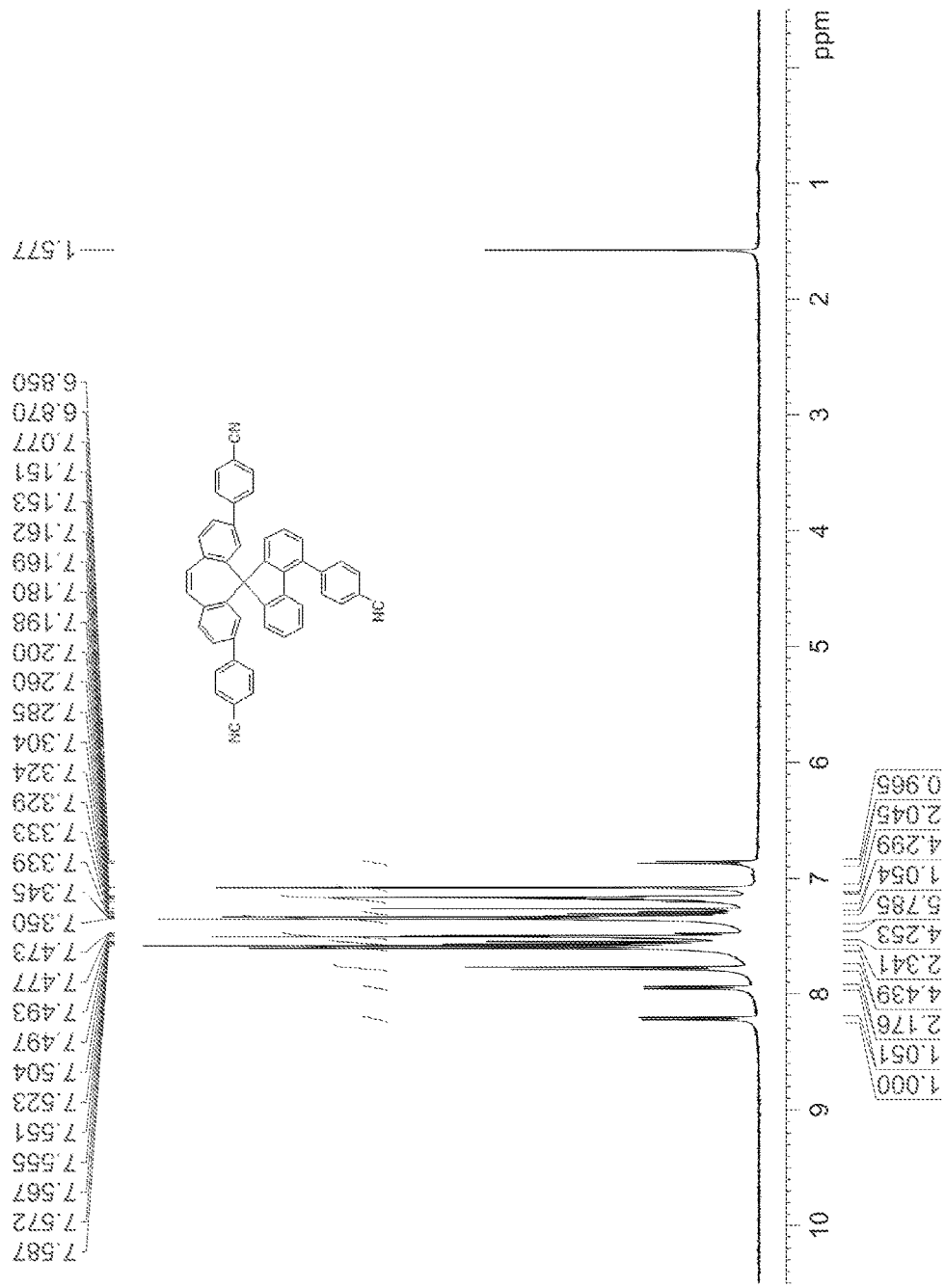
Figure 26:
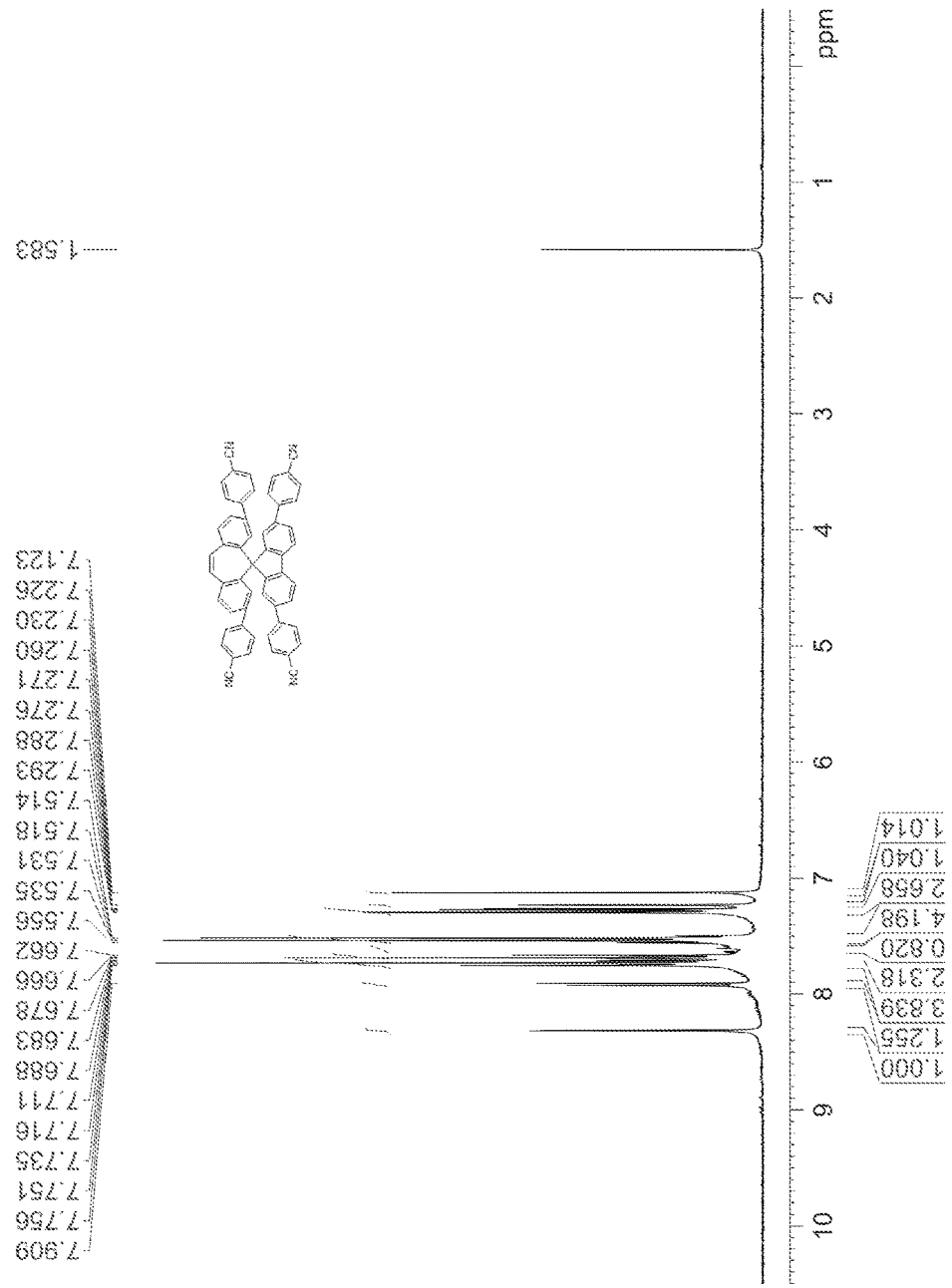

Hereinafter, one skilled in the arts can easily realize the advantages and effects of a novel compound and an organic light emitting device using the same in accordance with the present invention from the following examples. It should be understood that the descriptions proposed herein are just preferable examples only for the purpose of illustrations, not intended to limit the scope of the invention. Various modifications and variations could be made in order to practice or apply the present invention without departing from the spirit and scope of the invention.

Preparation of Intermediate A

Intermediates A1 to A7 were prepared to synthesize the novel compound. Intermediates A1 to A7 could be purchased or synthesized by the following steps. The specific chemical structures of the Intermediates A1 to A7 were listed in Table 1.

TABLE 1 chemical structures of intermediates A1 to A7.

Intermediate A1

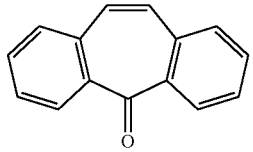 [SMILES: O=c1c2ccccc2ccc2ccccc12]

Intermediate A2

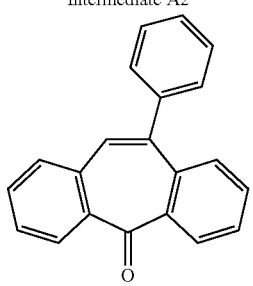

Intermediate A3

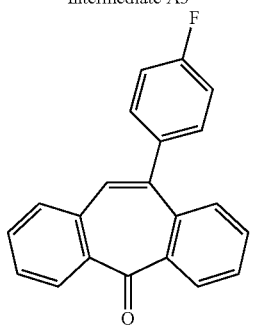

TABLE 1-continued chemical structures of intermediates A1 to A7.

Intermediate A4

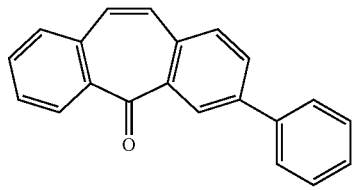 [SMILES: O=c1c2ccccc2ccc2ccc(-c3ccccc3)cc12]

Intermediate A5

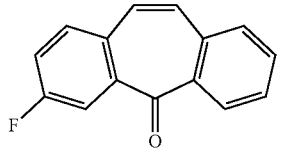 [SMILES: O=c1c2ccccc2ccc2ccc(F)cc12]

Intermediate A6

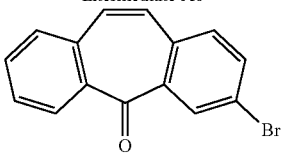

Intermediate A7

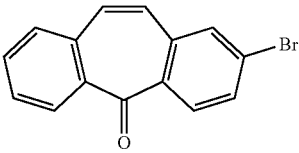 [SMILES: O=c1c2ccccc2ccc2cc(Br)ccc12]

Intermediate A1

Intermediate A1 was purchased from Sigma-Aldrich, CAS No. 2222-33-5.

Synthesis of Intermediate A2

The synthesis pathway of the Intermediate A2 was summarized in Scheme A1.

Scheme A1

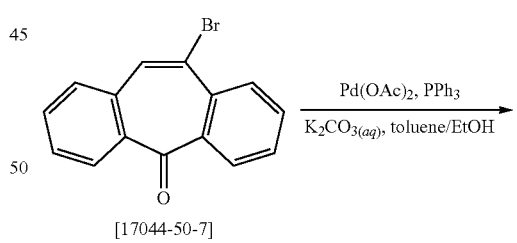

[17044-50-7]

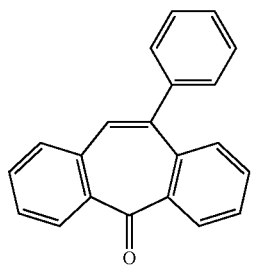

Intermediate A2

10-bromo-5H-dibenzo[a,d]cyclohepten-5-one (CAS No. 17044-50-7) (1.0 eq), phenylboronic acid (1.05 eq, CAS 98-80-6), Pd(OAc)$_2$ (0.012 eq), PPh$_3$ (0.048 eq), K$_2$CO$_3$ (2.0 eq, 3M) in toluene/EtOH (v=10:1) (0.3M) was heated at 90° C. for 16 hours. After completion of the reaction, the volatiles were removed under vacuum, and the resulting solution extracted with CH$_2$Cl$_2$. The combined organic extract was washed with brine solution, dried over Na$_2$SO$_4$. Then the resulting solution was concentrated under reduced pressure and purified by column chromatography to obtain orange oil in a yield of 97%.

The oil product was identified as Intermediate A2 by a field desorption mass spectroscopy (FD-MS) analysis. FD-MS analysis: C$_{21}$H$_{14}$O: theoretical value of 282.34 and observed value of 282.34.

Synthesis of Intermediate A3

Intermediate A3 was synthesized in a similar manner as intermediate A2, except that the phenylboronic acid was replaced by 4-fluorobenzeneboronic acid (CAS No. 1765-93-1). The yield of synthesize intermediate A3 is 96%. FD-MS analysis: C$_{21}$H$_{13}$FO: theoretical value of 300.33 and observed value of 300.33.

Synthesis of Intermediate A4

Intermediate A4 were synthesized in a similar manner as intermediate A2, except that the 10-bromo-5H-dibenzo[a,d]cyclohepten-5-one was replaced by 2-bromodibenzoheptenone (CAS No. 124853-22-1). The yield of synthesize intermediate A4 is 94%. FD-MS analysis: C$_{21}$H$_{14}$O: theoretical value of 282.34 and observed value of 282.34.

Synthesis of Intermediates A5

Intermediates A5 used for preparing a novel compound was synthesized by the following steps. The synthesis pathway of the Intermediate A5 was summarized in Scheme A2 and the results were listed in Table 2.

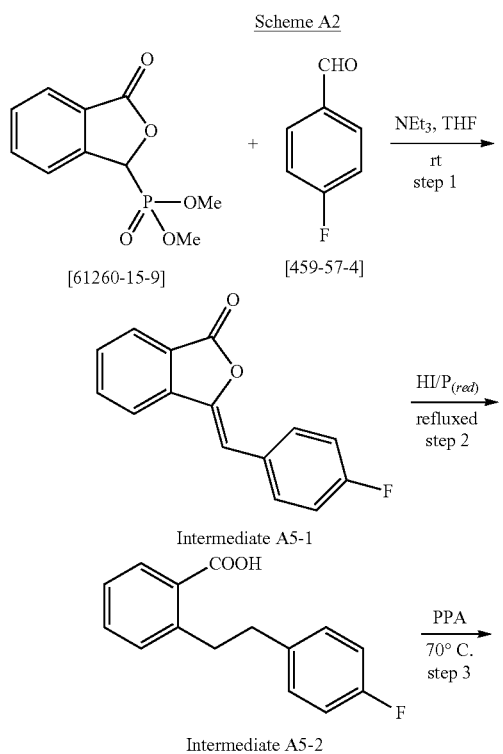

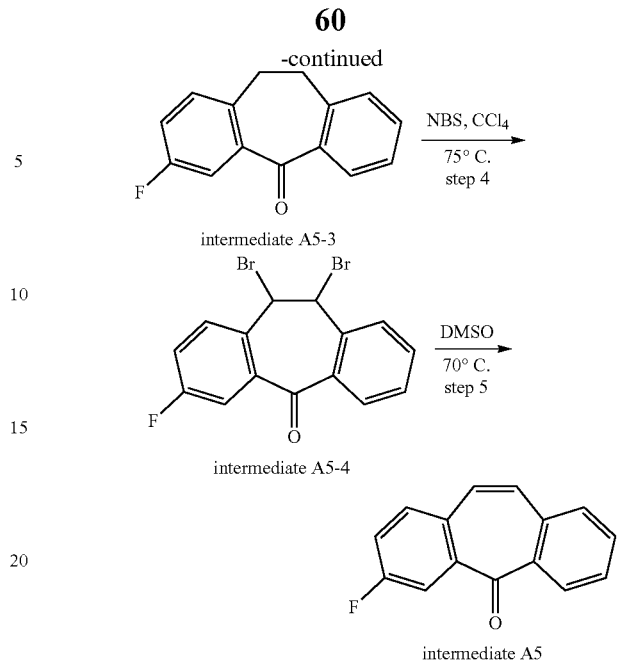

Step1: Synthesis of Intermediate A5-1

A solution of dimethyl(3-oxo-1,3-dihydroisobenzofuran-1-yl)phosphonate (1.0 eq) (CAS No. 61260-15-9), 4-fluorobenzaldehyde (0.7 eq) (CAS No. 459-57-4) in THF (2.5M) was slowly added NEt$_3$ (10 eq). The resulting mixture was stirring at room temperature for 24 hours. After the reaction was completed, the reaction mixture was concentrated under reduced pressure. The reaction mass was washed with water and MeOH then filtered to afford the intermediate A5-1 as a yellow solid.

Step2: Synthesis of Intermediate A5-2

Intermediate A5-1 (1.0 eq), red phosphorous (4.5 eq) in HI (8.5 eq) was heated to refluxed for 24 h. After the reaction was completed, the warm liquid was poured on ice and filtered. The precipitate was washed thoroughly with water and heated under reflux for 1 hr with ammonium hydroxide. The hot solution was filtered and acidified with hydrochloric acid to get intermediate A5-2 which was going to the next step without further purification.

Step3: Synthesis of Intermediate A5-3

Intermediate A5-2 (1.0 eq) in polyphosphoric acid (PPA) was stirred at 70° C. for 6 h. The resulting mixture was cooled to room temperature and poured into ice water followed by basification with sodium hydroxide solution and extracted with EtOAc. The residue was purified with column chromatography. The residual mass was recrystallized with toluene to obtain a white solid product.

Step4 Synthesis of Intermediate A5-4

Into a round-bottom flask, was placed a solution of Intermediate A5-3 (1.0 eq), N-bromosuccinimide (2.0 eq), and benzoyl peroxide (1.0% eq) in CCl$_4$ (5 times to Intermediate A5-3). The mixture turned bright red and was refluxed for 20 hours in the dark. The warm solution was washed with warm H$_2$O (2×1500 mL) and 3% NaHCO$_3$ (aq) (2×1500 mL). The organic layer was separated and evaporated under reduced pressure to yield 214.0 g (quant. recovery) of a highly insoluble off-white solid of intermediate A5-4, which was moved onto the next reaction without purification.

Step 5: Synthesis of Intermediate A5

Intermediate A5-4 (126.0 g) was dissolved in 378 ml of DMSO is stirred at 70° C. for 3 hours. After cooling to room temperature, the whole is poured into ice water with stirring and filtered. The white solid filtrate was washed with water and dried, whereby a light yellow solid product was obtained.

Synthesis of Intermediates A6 and A7

Intermediates A6 and A7 were synthesized in a similar manner as intermediate A5, except that the 4-fluorobenzaldehyde was respectively replaced by 4-bromobenzaldehyde and 3-bromobenzaldehyde. All intermediates were analyzed according to the methods as described above, and the results were listed in Table 2.

TABLE 2 the chemical structures, yields, formulae, and mass (M+) analyzed by FD-MS of Intermediates A5 to A7.

| Intermediate | A5-1 | A5-2 | A5-3 | A5-4 | A5 |
|---|---|---|---|---|---|
| Chemical Structure | (structure) | (structure) | (structure) | (structure) | (structure) |
| Yield | 92% | 65% | 96% | 80% | 93% |
| Formula | $C_{15}H_9FO_2$ | NA | $C_{15}H_{11}FO$ | NA | $C_{15}H_9FO$ |
| Mass (M+) | 240.23 | NA | 226.25 | NA | 224.23 |
| Intermediate | A6-1 | A6-2 | A6-3 | A6-4 | A6 |
| Chemical Structure | (structure) | (structure) | (structure) | (structure) | (structure) |
| Yield | 96% | 75% | 94% | 99% | 90% |
| Formula | $C_{15}H_9BrO_2$ | NA | $C_{15}H_{11}BrO$ | NA | $C_{15}H_9BrO$ |
| Mass (M+) | 301.13 | NA | 287.15 | NA | 285.14 |
| Intermediate | A7-1 | A7-2 | A7-3 | A7-4 | A7 |
| Chemical Structure | (structure) | (structure) | (structure) | (structure) | (structure) |
| Yield | 98% | 68% | 88% | 81% | 95% |
| Formula | $C_{15}H_9BrO_2$ | NA | $C_{15}H_{11}BrO$ | NA | $C_{15}H_9BrO$ |
| Mass (M+) | 301.13 | NA | 287.15 | NA | 285.14 |

Preparation of Intermediate B

Intermediates B1 to B3 used for preparing a novel compound were purchased from Sigma-Aldrich and were listed in Table 3.

TABLE 3 chemical structures and CAS No. of intermediates B1 to B3.

| Intermediate B1 | Intermediate B2 | Intermediate B3 |
|---|---|---|
| ![B1 structure] | ![B2 structure] | ![B3 structure] |
| [179526-95-5] | [154407-17-7] | [2052-07-5] |

Synthesis of Intermediate C

Intermediates C1 to C13 were synthesized by Scheme C1. Specifically, intermediates C1, C3, C9, C11, and C12 were synthesized through step 1 and step 2 in scheme C1. Intermediates C2, C4 to C8, and C10 were synthesized through step 1 and step 2 in and were further modified through step 3 in scheme C1. The yields and FD-MS analysis data of intermediates C1 to C13 are listed in the Table 4.

Scheme C1

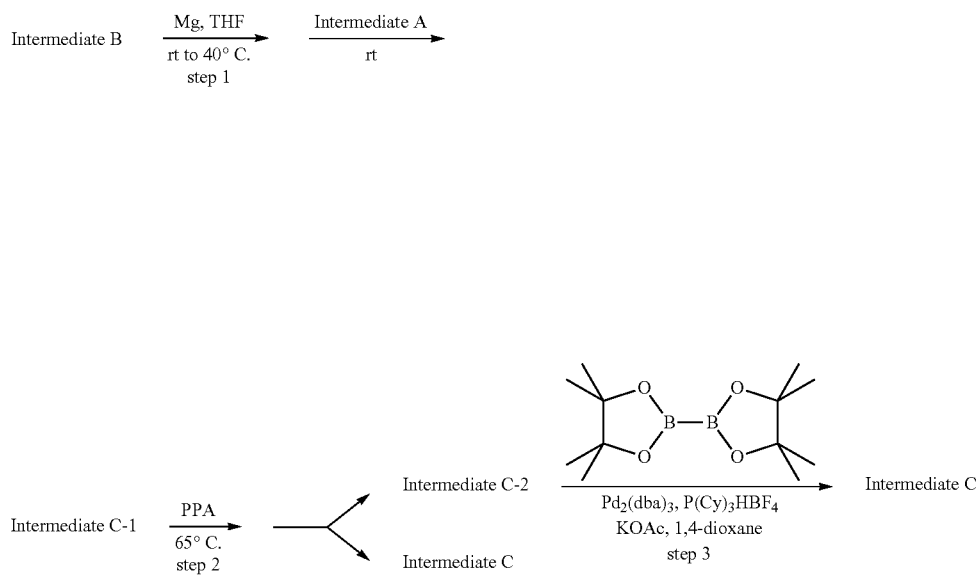

Step 1: Synthesis of Intermediate C-1

Magnesium (1.0 eq) was put into a 200 ml three-neck flask with 125 ml THF and stirred for 0.5 hour while reducing pressure with a rotary pump. Then 5.0 ml of diethyl ether and one drop of dibromoethane were added under a nitrogen gas stream. Then, Intermediate B (1.0 eq) was dropped into this solution at a pace that maintained reflux flow. After completion of dropping, the reaction mixture was heated at 40° C. for 3 hours so as to become a Grignard reagent. The Grignard reagent was cooled to room temperature and the foresaid Intermediate A (0.7 eq) was added into the flask by three portions at 0° C. and stirred at room temperature for 12 hours. When the reaction was completed, the reaction solution was washed with water, and a water layer was extracted with ethyl acetate. The extracted solution and an organic layer were combined and washed with saturated saline, and then dried with $MgSO_4$. After drying, this mixture was subjected to suction filtration, and a filtrate was concentrated to give a light yellow, powdery solid of "Intermediate C-1".

Step 2: Synthesis of Intermediate C-2

Intermediate C-1 (10 g) in 30 ml of PPA was stirred at 65° C. for 6 hours. After cooling, the reaction was poured into ice water basified with NaOH and extracted with ethylacetate. The organic layer is washed with brine, dried and concentrated. The solvent was then removed by a rotary evaporator, and the remaining substance was purified with column chromatography to obtain Intermediate C-2.

Step 3: Synthesis of Intermediate C

A mixture of Intermediate C-2 (1.0 eq), bis(pinacolato)diboron (1.2 eq), $Pd_2(dba)_3$ (0.015 eq), $P(Cy)_3HBF_4$ (0.06 eq), and KOAc (3.0 eq) in 1,4-dioxane (0.3M) was heated at 110° C. for 8 hours under nitrogen atmosphere. After cooling to room temperature, the solvent was then removed under reduced pressure, and the residue was purified via column chromatography to obtain pale yellow solids.

TABLE 4

Intermediates A and Intermediates B to synthesize the Intermediates C1 to C13, chemical structures, yields, formulae, and mass of Intermediates C1 to C13.

| | Intermediate C-1 | | Intermediate C-2 | | Intermediate C | | |
|---|---|---|---|---|---|---|---|
| | Chemical Structure | Yield (%) | Chemical Structure | Yield (%) | Chemical Structure | Yield (%) | Formula/Mass (M+) |
| A1  B1 | Intermediate C1-1 | 85 | — | — | Intermediate C1 | 96 | $C_{27}H_{17}Cl$ (376.88) |
| A1  B1 | Intermediate C1-1 | 85 | Intermediate C1 | 96 | Intermediate C2 | 97 | $C_{33}H_{29}BO_2$ (468.39) |
| A1  B2 | Intermediate C3-1 | 76 | — | — | Intermediate C3 | 87 | $C_{27}H_{17}Cl$ (376.88) |

TABLE 4-continued

Intermediates A and Intermediates B to synthesize the Intermediates C1 to C13, chemical structures, yields, formulae, and mass of Intermediates C1 to C13.

| | | Intermediate C-1 | | Intermediate C-2 | | Intermediate C | | |
|---|---|---|---|---|---|---|---|---|
| | | Chemical Structure | Yield (%) | Chemical Structure | Yield (%) | Chemical Structure | Yield (%) | Formula/Mass (M⁺) |
| A1 | B2 |  Intermediate C3-1 | 76 |  Intermediate C3 | — | 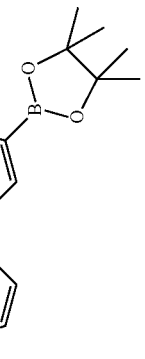 Intermediate C4 | 96 | $C_{33}H_{29}BO_2$ (468.39) |
| A2 | B1 | 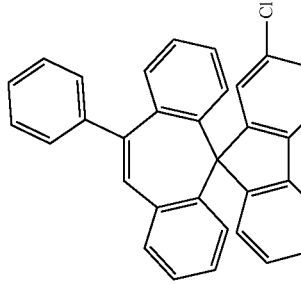 Intermediate C5-1 | 88 | 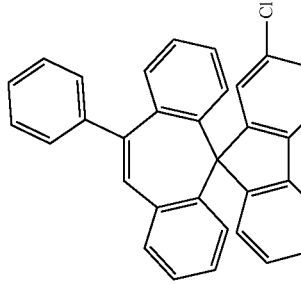 Intermediate C5-2 | 88 | 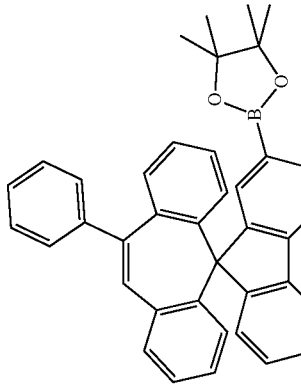 Intermediate C5 | 94 | $C_{39}H_{33}BO_2$ (544.49) |

TABLE 4-continued

Intermediates A and Intermediates B to synthesize the Intermediates C1 to C13, chemical structures, yields, formulae, and mass of Intermediates C1 to C13.

| | | Intermediate C-1 | | Intermediate C-2 | | Intermediate C | | |
|---|---|---|---|---|---|---|---|---|
| | | Chemical Structure | Yield (%) | Chemical Structure | Yield (%) | Chemical Structure | Yield (%) | Formula/ Mass (M+) |
| A3 | B1 | Intermediate C6-1 | 95 | Intermediate C6-2 | 90 | Intermediate C6 | 91 | $C_{39}H_{32}BFO_2$ (562.48) |
| A4 | B1 | Intermediate C7-1 | 78 | Intermediate C7-2 | 81 | Intermediate C7 | 91 | $C_{39}H_{33}BO_2$ (544.49) |

TABLE 4-continued

Intermediates A and Intermediates B to synthesize the Intermediates C1 to C13, chemical structures, yields, formulae, and mass of Intermediates C1 to C13.

| | | Intermediate C-1 | | Intermediate C-2 | | Intermediate C | |
|---|---|---|---|---|---|---|---|
| | | Chemical Structure | Yield (%) | Chemical Structure | Yield (%) | Chemical Structure | Yield (%) | Formula/ Mass (M+) |
| A5 | B2 | Intermediate C8-1 | 86 | Intermediate C8-2 | 86 | Intermediate C8 | 96 | $C_{33}H_{28}BFO_2$ (486.38) |
| A6 | B3 | Intermediate C9-1 | 92 | — | — | Intermediate C9 | 86 | $C_{27}H_{17}Br$ (421.33) |
| A6 | B3 | Intermediate C9-1 | 92 | Intermediate C9 | 86 | Intermediate C10 | 91 | $C_{33}H_9BO_2S$ (468.39) |

TABLE 4-continued

Intermediates A and Intermediates B to synthesize the Intermediates C1 to C13, chemical structures, yields, formulae, and mass of Intermediates C1 to C13.

| | | Intermediate C-1 | | Intermediate C-2 | | Intermediate C | | |
|---|---|---|---|---|---|---|---|---|
| | | Chemical Structure | Yield (%) | Chemical Structure | Yield (%) | Chemical Structure | Yield (%) | Formula/ Mass (M+) |
| A7 | B3 | 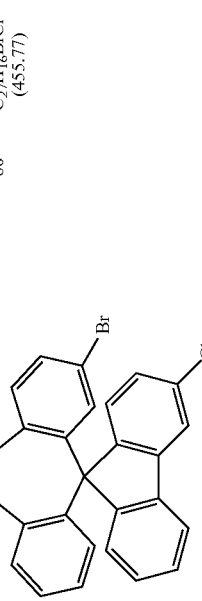 Intermediate C11-1 | 90 | — | — | 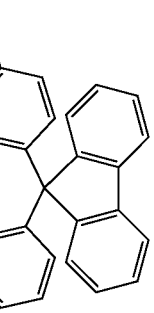 Intermediate C11 | 91 | $C_{33}H_{29}BO_2S$ (468.39) |
| A6 | B2 | 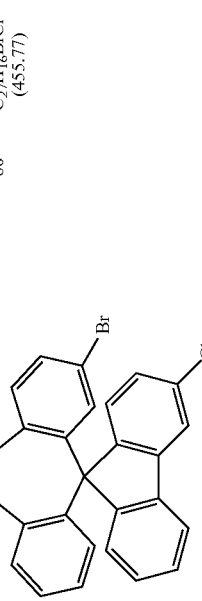 Intermediate C12-1 | 85 | — | — | 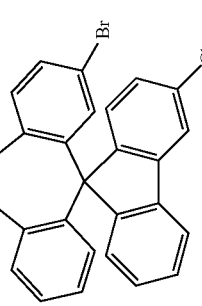 Intermediate C12 | 80 | $C_{27}H_{16}BrCl$ (455.77) |

Synthesis of Intermediate C13

Intermediates C13 used for preparing a novel compound were synthesized by following step in scheme C2.

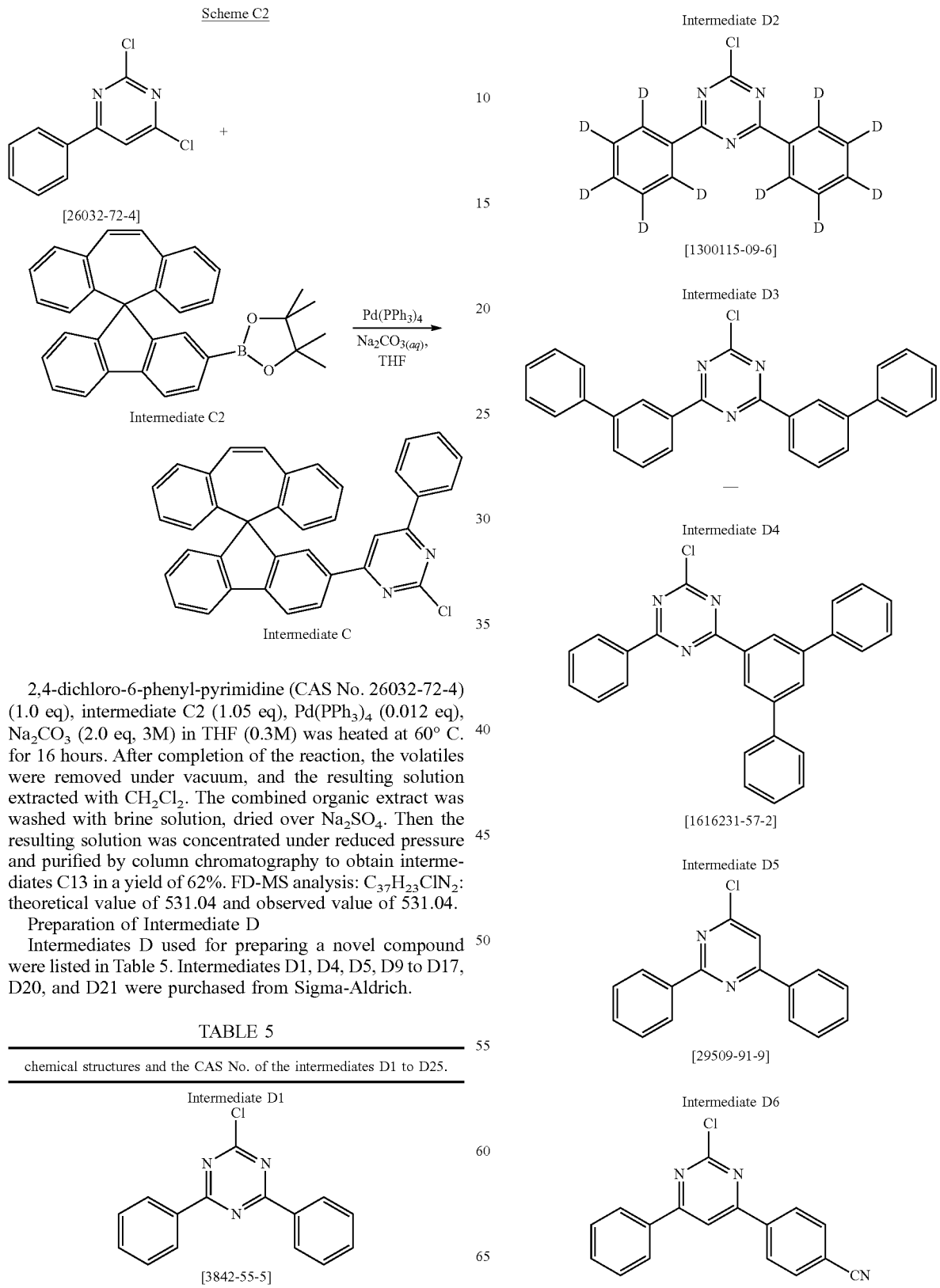

2,4-dichloro-6-phenyl-pyrimidine (CAS No. 26032-72-4) (1.0 eq), intermediate C2 (1.05 eq), Pd(PPh$_3$)$_4$ (0.012 eq), Na$_2$CO$_3$ (2.0 eq, 3M) in THF (0.3M) was heated at 60° C. for 16 hours. After completion of the reaction, the volatiles were removed under vacuum, and the resulting solution extracted with CH$_2$Cl$_2$. The combined organic extract was washed with brine solution, dried over Na$_2$SO$_4$. Then the resulting solution was concentrated under reduced pressure and purified by column chromatography to obtain intermediates C13 in a yield of 62%. FD-MS analysis: C$_{37}$H$_{23}$ClN$_2$: theoretical value of 531.04 and observed value of 531.04.

Preparation of Intermediate D

Intermediates D used for preparing a novel compound were listed in Table 5. Intermediates D1, D4, D5, D9 to D17, D20, and D21 were purchased from Sigma-Aldrich.

TABLE 5-continued
chemical structures and the CAS No. of the intermediates D1 to D25.
Intermediate D7
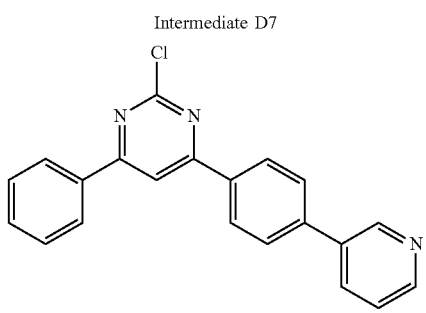
—
Intermediate D8
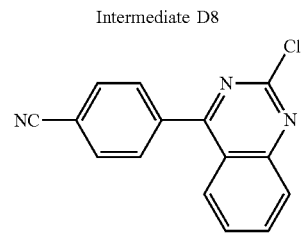
—
Intermediate D9
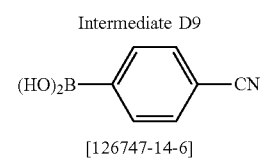
[126747-14-6]
Intermediate D10
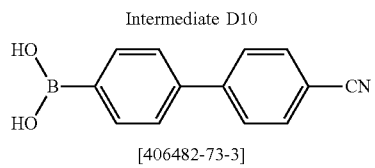
[406482-73-3]
Intermediate D11
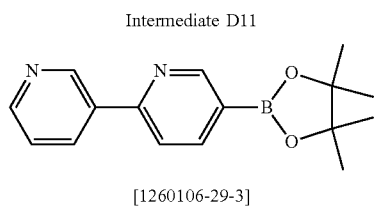
[1260106-29-3]
Intermediate D12
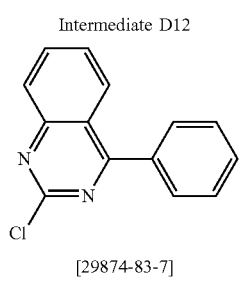
[29874-83-7]
TABLE 5-continued
chemical structures and the CAS No. of the intermediates D1 to D25.
Intermediate D13
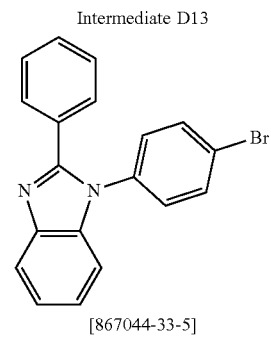
[867044-33-5]
Intermediate D14
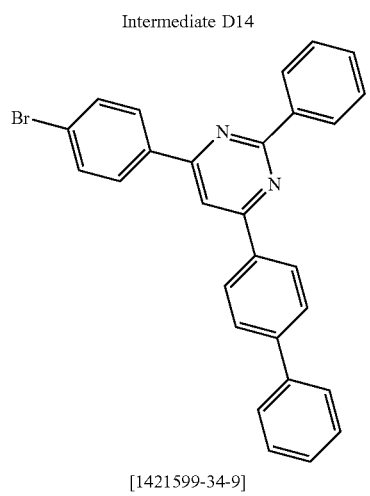
[1421599-34-9]
Intermediate D15
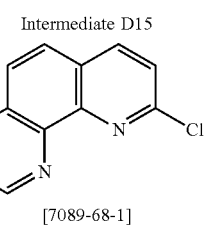
[7089-68-1]
Intermediate D16
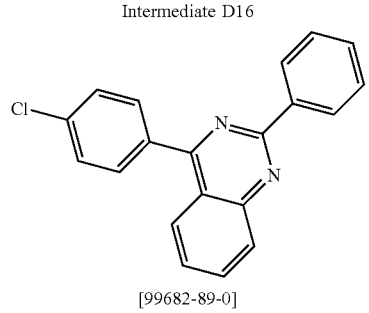
[99682-89-0]
Intermediate D17
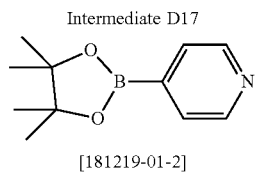
[181219-01-2]

TABLE 5-continued chemical structures and the CAS No. of the intermediates D1 to D25.

Intermediate D18

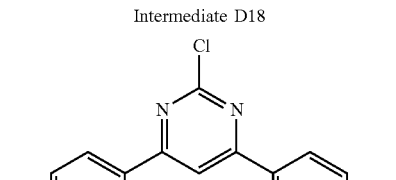

[1588407-97-9]

Intermediate D19

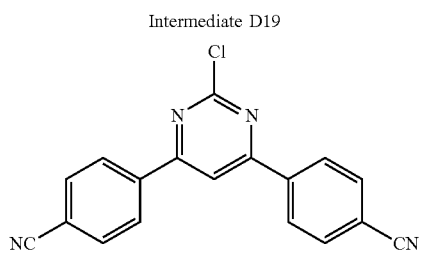

Intermediate D20

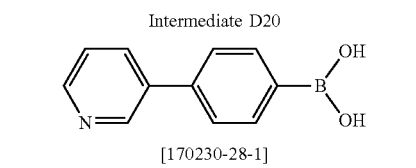

[170230-28-1]

Intermediate D21

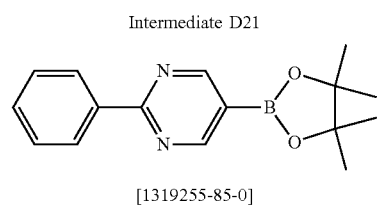

[1319255-85-0]

Intermediate D22

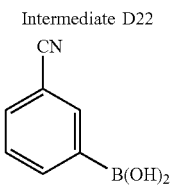

Intermediate D23

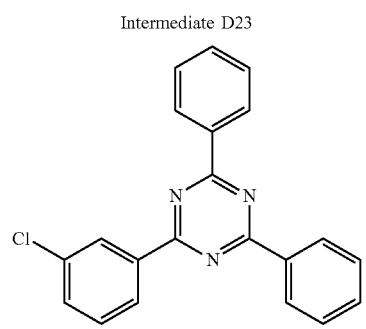

TABLE 5-continued chemical structures and the CAS No. of the intermediates D1 to D25.

Intermediate D24

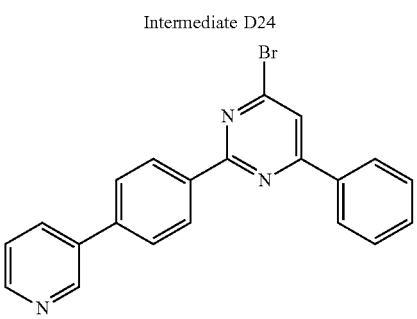

Intermediate D25

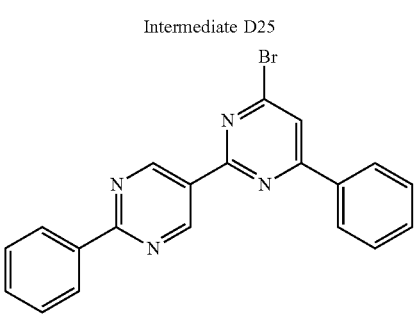

Synthesis of Intermediate D2

The synthesis pathway of the Intermediate D2 was summarized in Scheme D1.

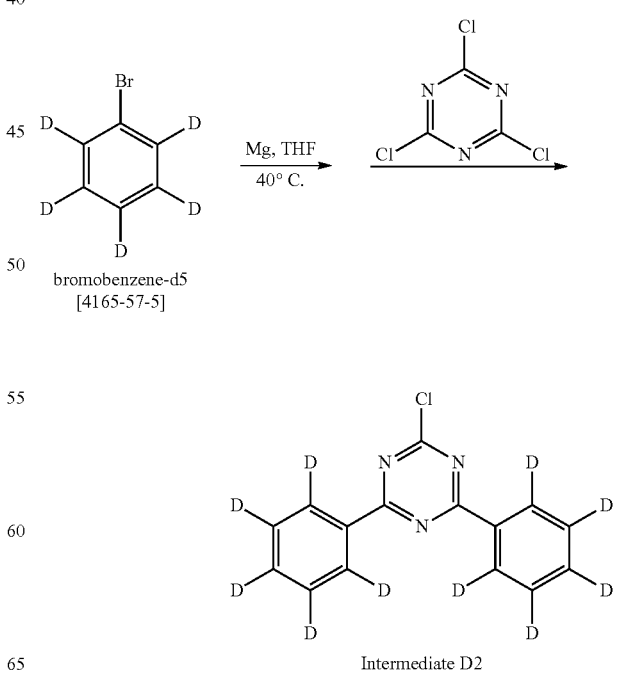

Scheme D1 bromobenzene-d5
[4165-57-5]

Intermediate D2

Magnesium (1.0 eq) was put into a 200 ml three-neck flask with 125 ml THF and stirred for 0.5 hour while reducing pressure with a rotary pump. Bromobenzene-d5 (3.0 eq) was dropped into this mixture at a pace that maintained reflux flow. After completion of dropping, the reaction mixture was heated at 40° C. for 3 hours so as to become a Grignard reagent. The reagent is then cooled to room temperature and the foresaid 1,3,5-trichloro-2,4,6-triazine (1.0 eq) was added into the flask by three portions at 0° C. and stirred at room temperature for 12 hours. When the reaction was completed, the reaction solution was washed with water, and a water layer was extracted with ethyl acetate. The extracted solution and an organic layer were combined and washed with saturated saline, and then dried with $MgSO_4$. After drying, this mixture was subjected to suction filtration, and a filtrate was concentrated to give a yellow, powdery solid of intermediate D2 in a yield of 66%. FD-MS analysis: $C_{15}H_{10}ClN_3$: theoretical value of 277.7 and observed value of 277.7.

Synthesis of Intermediate D3

Intermediate D3 were synthesized in a similar manner as intermediate D2, except that bromobenzene-d5 was replaced by 3-bromobiphenyl (CAS No. 2113-57-7). The yield of synthesize Intermediate D3 is 68%. FD-MS analysis: $C_{27}H_{18}ClN_3$: theoretical value of 419.90 and observed value of 419.90.

Synthesis of Intermediates D6 and D7

The synthesis pathway of Intermediates D6 and D7 was summarized in scheme D2.

Scheme D2

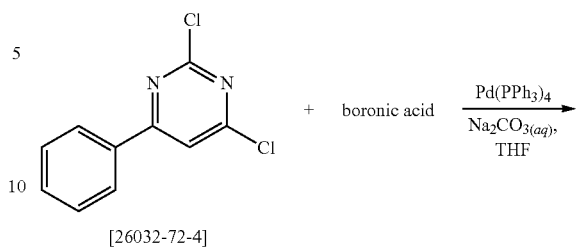

Intermediate D6 and D7

2,4-dichloro-6-phenyl-pyrimidine (CAS No. 26032-72-4) (1.0 eq), phenylboronic acid (1.05 eq, CAS 98-80-6), $Pd(PPh_3)_4$ (0.012 eq), $Na_2CO_3$ (2.0 eq, 3M) in THF (0.3M) was heated at 60° C. for 16 hours. After completion of the reaction, the volatiles were removed under vacuum, and the resulting solution extracted with $CH_2Cl_2$. The combined organic extract was washed with brine solution, dried over $Na_2SO_4$. Then the resulting solution was concentrated under reduced pressure and purified by column chromatography to obtain intermediates D6 and D7.

The yield and FD-MS analysis data of intermediate D6 to D7 are listed in the following Table 6.

TABLE 6 the chemical structures of the boronic acid and the chemical structures, yields, formulae, and mass (M+) analyzed by FD-MS of intermediates D6 and D7.

| Boronic acid | Intermediate D | | |
|---|---|---|---|
| Chemical Structure | Chemical Structure | Yield (%) | Formula/ Mass (M+) |
| 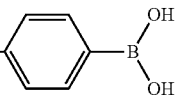  [126747-14-6] | 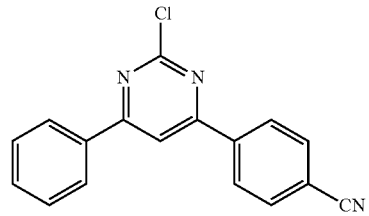 [SMILES: N#Cc1ccc(-c2cc(-c3ccccc3)nc(Cl)n2)cc1]  Intermediate D6 | 52 | $C_{17}H_{10}ClN_3$ (291.73) |
| 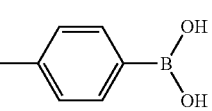  [170230-28-1] | 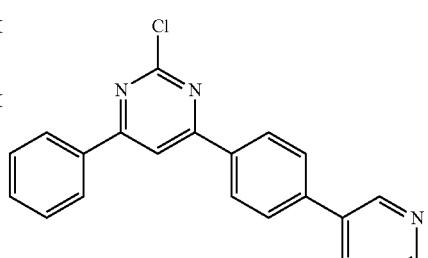  Intermediate D7 | 68 | $C_{21}H_{14}ClN_3$ (343.81) |

Synthesis of Intermediate D8

Intermediate D8 used for preparing a novel compound was synthesized by the following steps. The synthesis pathway of the Intermediate D8 was summarized in Scheme D3.

Scheme D3

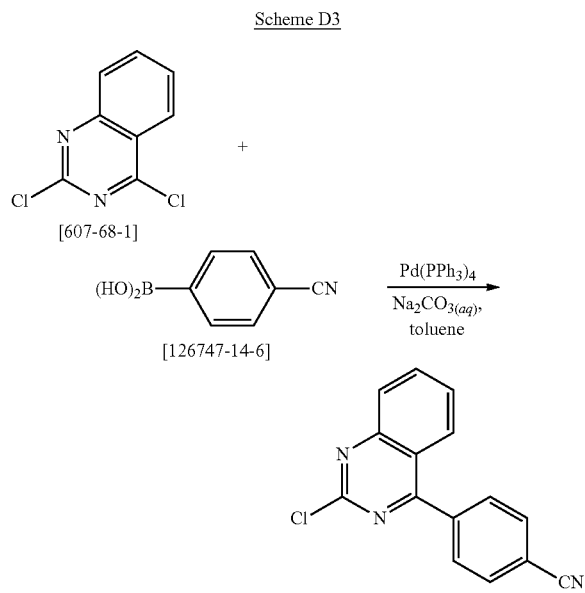

2,4-dichloroquinazoline (1.0 eq, CAS No. 607-68-1), 4-cyanophenylboronic acid (1.05 eq, CAS No. 126747-14-6), Pd(PPh$_3$)$_4$ (0.012 eq), and Na$_2$CO$_3$ (2.0 eq, 3M) in toluene (0.3M) was heated at 90° C. for 16 hours. After completion of the reaction, the volatiles were removed under vacuum, and the resulting solution extracted with CH$_2$Cl$_2$. The combined organic extract was washed with brine solution, dried over Na$_2$SO$_4$. Then the resulting solution was concentrated under reduced pressure and purified by column chromatography to obtain intermediate D8 in a yield of 83%. FD-MS analysis: C$_{15}$H$_8$ClN$_3$: theoretical value of 265.70 and observed value of 265.70.

Synthesis of Intermediates D18 and D19

Intermediates D18 and D19 used for preparing a novel compound were synthesized by following step in scheme D4.

Scheme D4

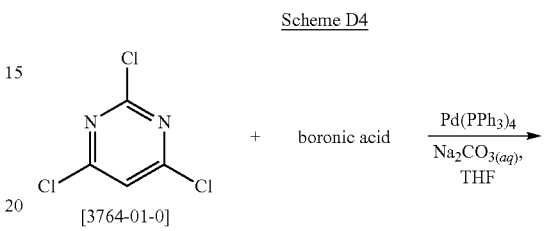

Intermediate D18 and D19

2,4,6-trichloropyrimidine (CAS No. 3764-01-0) (1.0 eq), boronic acid (1.05 eq), Pd(PPh$_3$)$_4$ (0.012 eq), Na$_2$CO$_3$ (2.0 eq, 3M) in THF (0.3M) was heated at 60° C. for 16 hours. After completion of the reaction, the volatiles were removed under vacuum, and the resulting solution extracted with CH$_2$Cl$_2$. The combined organic extract was washed with brine solution, dried over Na$_2$SO$_4$. Then the resulting solution was concentrated under reduced pressure and purified by column chromatography to obtain intermediates D18 and D19.

The yield and FD-MS analysis data of intermediate D18 to D19 are listed in the following Table 7.

TABLE 7 the chemical structures of the boronic acid and the chemical structures, yields, formulae, and mass (M$^+$) analyzed by FD-MS of intermediates D18 and D19.

| Boronic acid | Intermediate D | | |
|---|---|---|---|
| Chemical Structure | Chemical Structure | Yield (%) | Formula/ Mass (M$^+$) |
| [1765-93-1] (4-fluorophenylboronic acid) | Intermediate D18 | 90 | C$_{16}$H$_9$ClF$_2$N$_2$ (302.71) |
| [126747-14-6] (4-cyanophenylboronic acid) | Intermediate D19 | 68 | C$_{18}$H$_9$ClN$_4$ (316.74) |

Synthesis of Novel Compounds

Each of intermediates C1 to C13 could be reacted with any one of various intermediates D1 to D25 to synthesize various claimed novel compounds. The general synthesis pathway of the claimed novel compound was summarized in Scheme I-A or Scheme I-B. In the following Scheme I-A or Scheme I-B, "Intermediate C" may be any one of Intermediate s C1 to C13 as listed in Table 4, and "Intermediate D" may be any one of foresaid Intermediates D1 to D25 in Table 5. The compounds were each synthesized by the following method A or B and results were listed in Table 8.

Method A

Scheme I-A

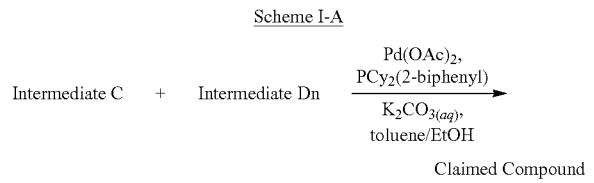

Claimed Compound

Intermediate C (1.0 eq), intermediate Dn (2.1 eq), Pd(OAc)$_2$ (0.01 eq), P(Cy)$_2$(2-biphenyl) 0.04 eq), toluene/ethanol (0.5M, v/v=10/1), and 3.0M of K$_2$CO$_3$ aqueous solution, followed by stirring at 100° C. for 12 h under nitrogen atmosphere. After completion of the reaction, water and toluene were added to the reaction mass. Subsequently, the organic layer was recovered by solvent extraction operation and dried over sodium sulfate. The solvent was then removed from the organic layer under reduced pressure, and the resulting residue was purified by silica gel column chromatography. The obtained residue was recrystallized with toluene to obtain white solid as claimed novel compound.

Method B

Scheme I-B

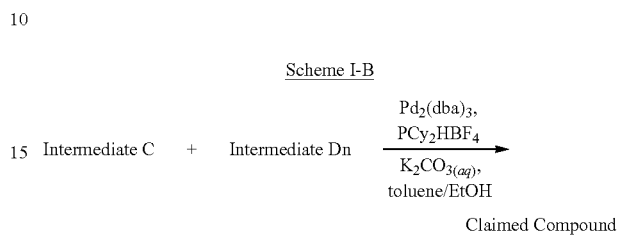

Claimed Compound

Intermediate C (1.0 eq), intermediate Dn (1.1 eq), Pd$_2$(dba)$_3$ (0.01 eq), P(Cy)$_3$HBF$_4$ (0.04 eq), toluene/ethanol (0.5M, v/v=10/1), and 3.0M of K$_2$CO$_3$ aqueous solution, followed by stirring at 100° C. for 12 h under nitrogen atmosphere. After completion of the reaction, water and toluene were added to the reaction mass. Subsequently, the organic layer was recovered by solvent extraction operation and dried over sodium sulfate. The solvent was then removed from the organic layer under reduced pressure, and the resulting residue was purified by silica gel column chromatography. The obtained residue was recrystallized with toluene to obtain white solid as claimed novel compound.

TABLE 8 intermediates adopted to prepare Compounds 1 to 31.

| No. | Method | Intermediate C | Intermediate D | Chemical Structure of Claimed Compound | Yield (%) | Formula/ Mass (M+) |
|---|---|---|---|---|---|---|
| SGM 616 | B | C4 | D1 | 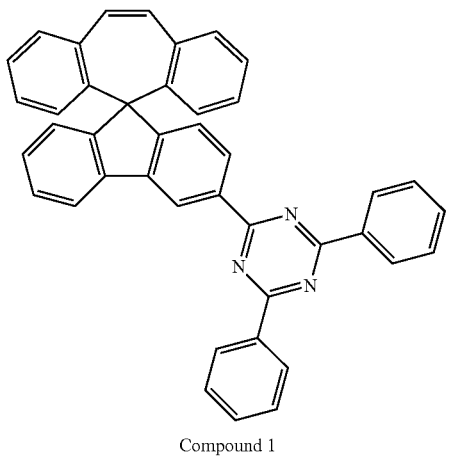 [SMILES: C1=Cc2ccccc2C2(c3ccccc31)c1ccccc1-c1cc(-c3nc(-c4ccccc4)nc(-c4ccccc4)n3)ccc12]<br>Compound 1 | 76 | C$_{42}$H$_{27}$N$_3$ (573.68) |

TABLE 8-continued
intermediates adopted to prepare Compounds 1 to 31.
| No. | Method | Intermediate C | Intermediate D | Chemical Structure of Claimed Compound | Yield (%) | Formula/ Mass (M+) |
|---|---|---|---|---|---|---|
| SGM 619 | B | C2 | D1 | 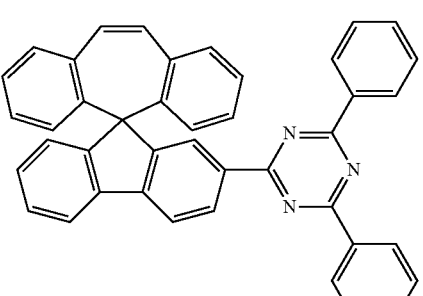Compound 2 | 97 | $C_{42}H_{27}N_3$ (573.68) |
| SGM 808 | A | C1 | D9 | 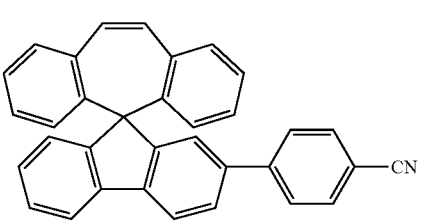Compound 3 | 74 | $C_{34}H_{21}N$ (443.54) |
| SGM 809 | A | C3 | D9 | 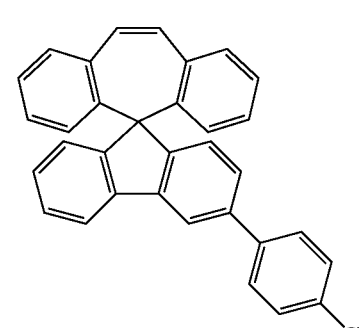Compound 4 | 74 | $C_{34}H_{21}N$ (443.54) |
| SGM 686 | B | C2 | D4 | 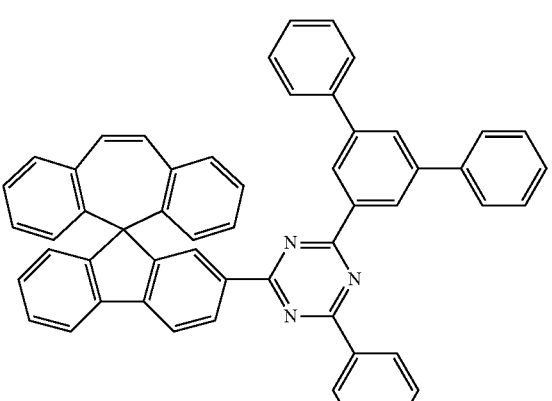Compound 5 | 85 | $C_{54}H_{35}N_3$ (725.88) |

TABLE 8-continued
intermediates adopted to prepare Compounds 1 to 31.
| No. | Method | Intermediate C | Intermediate D | Chemical Structure of Claimed Compound | Yield (%) | Formula/ Mass (M+) |
|---|---|---|---|---|---|---|
| SGM 729 | B | C4 | D3 | 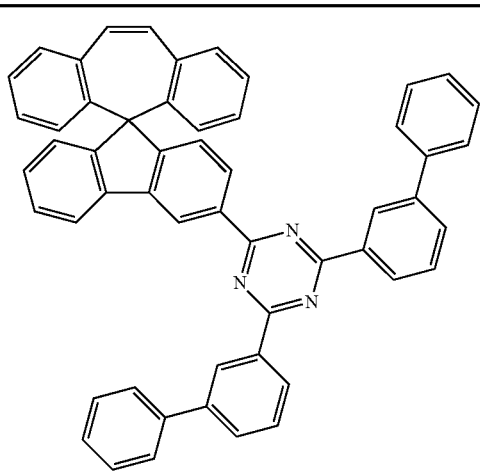<br>Compound 6 | 82 | $C_{54}H_{35}N_3$ (725.88) |
| SGM 701 | A | C2 | D5 | 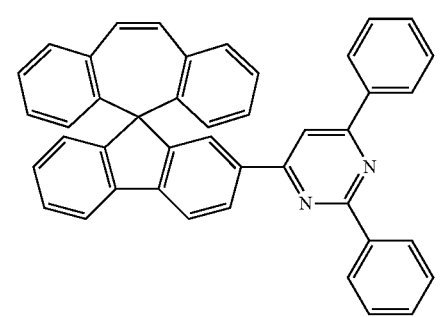<br>Compound 7 | 87 | $C_{43}H_{28}N_2$ (572.23) |
| SGM 719 | B | C4 | D2 | 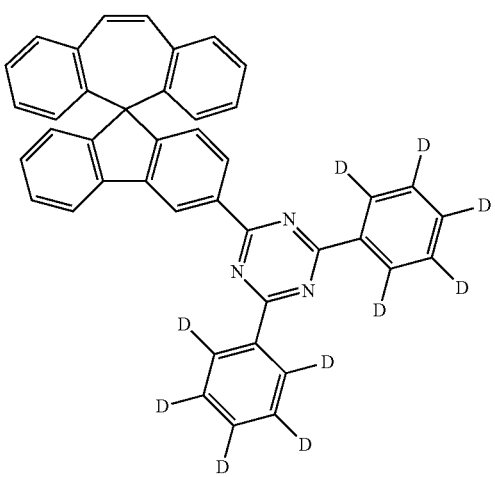<br>Compound 8 | 76 | $C_{42}H_{17}D_{10}N_3$ (583.75) | ature
TABLE 8-continued
intermediates adopted to prepare Compounds 1 to 31.
| No. | Method | Intermediate C | Intermediate D | Chemical Structure of Claimed Compound | Yield (%) | Formula/ Mass (M+) |
|---|---|---|---|---|---|---|
| SGM 807 | A | C2 | D8 | 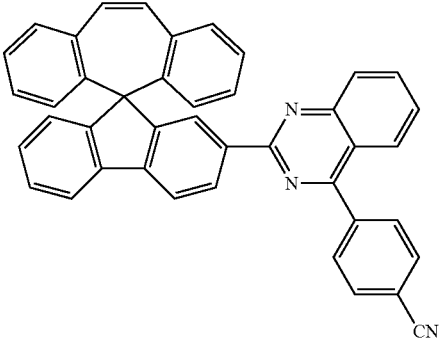<br>Compound 9 | 83 | $C_{42}H_{25}N_3$ (571.67) |
| SGM 818 | A | C2 | D7 | 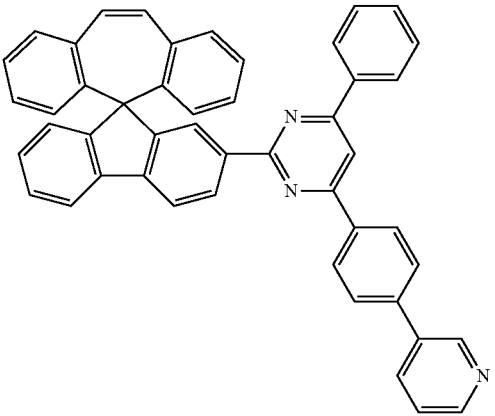<br>Compound 10 | 88 | $C_{48}H_{31}N_3$ (649.78) |
| SGM 824 | A | C2 | D19 | 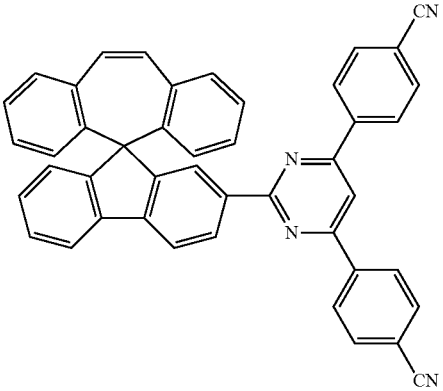<br>Compound 11 | 66 | $C_{45}H_{26}N_4$ (622.71) |

TABLE 8-continued
intermediates adopted to prepare Compounds 1 to 31.
| No. | Method | Intermediate C | Intermediate D | Chemical Structure of Claimed Compound | Yield (%) | Formula/ Mass (M+) |
|---|---|---|---|---|---|---|
| SGM 828 | A | C4 | D18 | 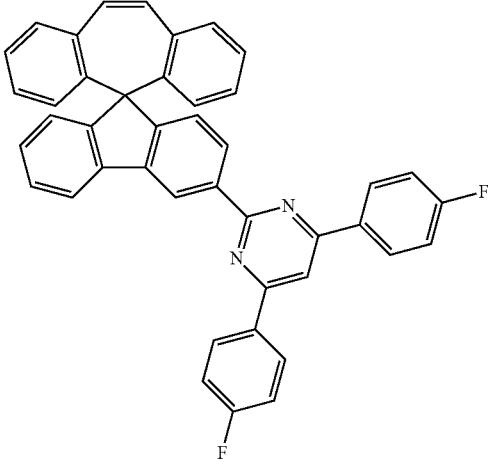  Compound 12 | 95 | $C_{43}H_{26}F_2N_2$ (608.68) |
| SGM 183 | B | C10 | D1 | 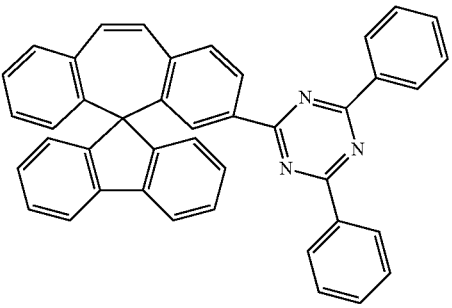  Compound 13 | 72 | $C_{42}H_{27}N_3$ (573.68) |
| SGM 309 | A | C9 | D9 | 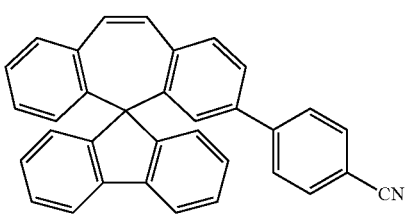  Compound 14 | 88 | $C_{34}H_{21}N$ (443.54) |

TABLE 8-continued intermediates adopted to prepare Compounds 1 to 31.

| No. | Method | Intermediate C | Intermediate D | Chemical Structure of Claimed Compound | Yield (%) | Formula/ Mass (M+) |
|---|---|---|---|---|---|---|
| SGM 832 | B | C6 | D1 | Compound 15 | 86 | $C_{48}H_{30}FN_3$ (667.77) |
| SGM 187 | A | C10 | D12 | Compound 16 | 75 | $C_{41}H_{26}N_2$ (546.66) |
| SGM 186 | A | C10 | D13 | Compound 17 | 95 | $C_{46}H_{30}N_2$ (610.74) |
| SGM 191 | A | C10 | D16 | Compound 18 | 92 | $C_{47}H_{30}N_2$ (622.75) |

TABLE 8-continued
intermediates adopted to prepare Compounds 1 to 31.
| No. | Method | Intermediate C | Intermediate D | Chemical Structure of Claimed Compound | Yield (%) | Formula/ Mass (M+) |
|---|---|---|---|---|---|---|
| SGM 202 | A | C10 | D14 | 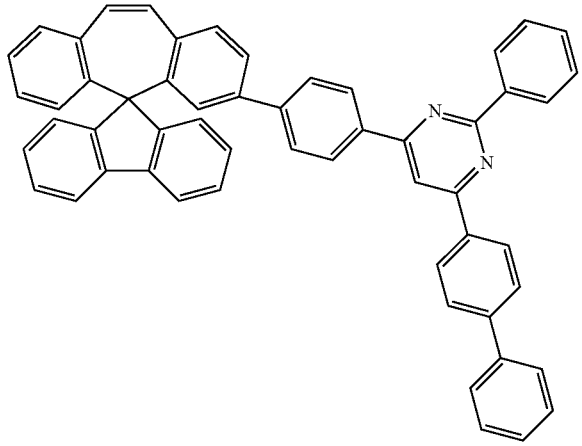<br>Compound 19 | 77 | $C_{55}H_{36}N_2$ (724.89) |
| SGM 219 | A | C11 | D9 | 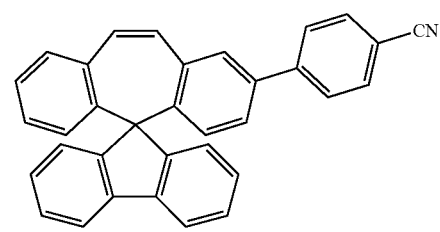<br>Compound 20 | 81 | $C_{34}H_{21}N$ (443.54) |
| SGM 810 | A | C9 | D10 | 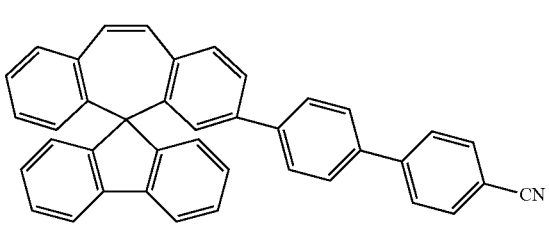<br>Compound 21 | 76 | $C_{40}H_{25}N$ (519.63) |
| SGM 811 | A | C9 | D11 | 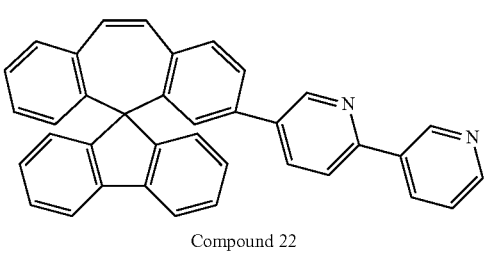 [SMILES: C1=Cc2ccc(-c3ccc(-c4cccnc4)nc3)cc2C2(c3ccccc31)c1ccccc1-c1ccccc12]<br>Compound 22 | 68 | $C_{37}H_{24}N_2$ (496.60) |

TABLE 8-continued
intermediates adopted to prepare Compounds 1 to 31.
| No. | Method | Intermediate C | Intermediate D | Chemical Structure of Claimed Compound | Yield (%) | Formula/ Mass (M+) |
|---|---|---|---|---|---|---|
| SGM 814 | B | C7 | D1 | 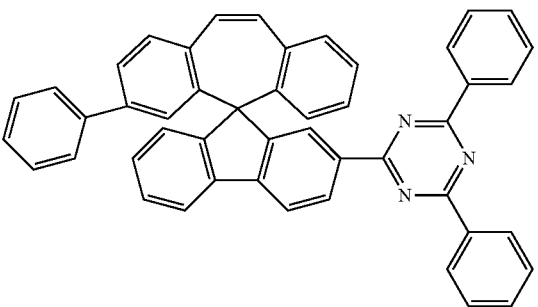<br>Compound 23 | 60 | $C_{48}H_{31}N_3$ (649.78) |
| SGM 389 | B | C12 | D9 | 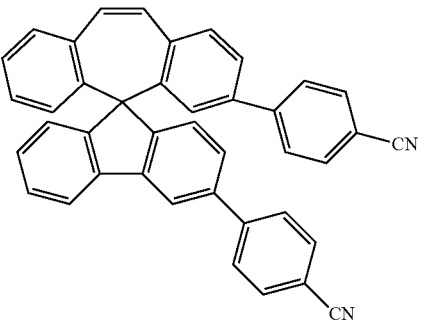<br>Compound 24 | 88 | $C_{41}H_{24}N_2$ (544.64) |
| SGM 629 | B | C5 | D1 | 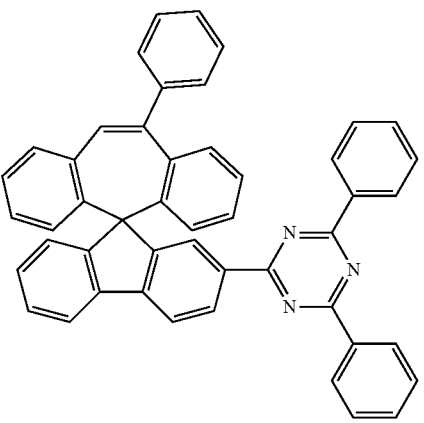<br>Compound 25 | 72 | $C_{48}H_{31}N_3$ (649.78) |

TABLE 8-continued
intermediates adopted to prepare Compounds 1 to 31.
| No. | Method | Intermediate C | Intermediate D | Chemical Structure of Claimed Compound | Yield (%) | Formula/ Mass (M+) |
|---|---|---|---|---|---|---|
| SGM 839 | A | C2 | D24 | 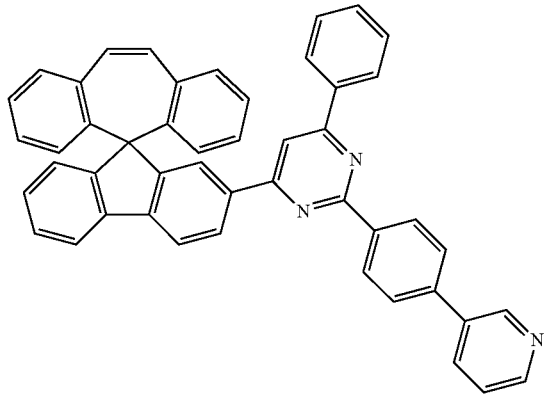  Compound 26 | 82 | $C_{48}H_{31}N_3$ (649.78) |
| SGM 840 | B | C8 | D1 | 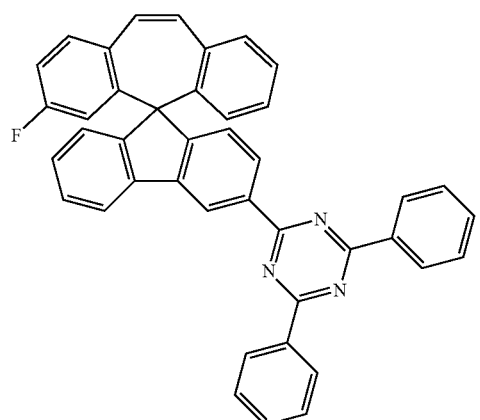  Compound 27 | 86 | $C_{42}H_{26}FN_3$ (591.67) |
| SGM 841 | B | C8 | D3 | 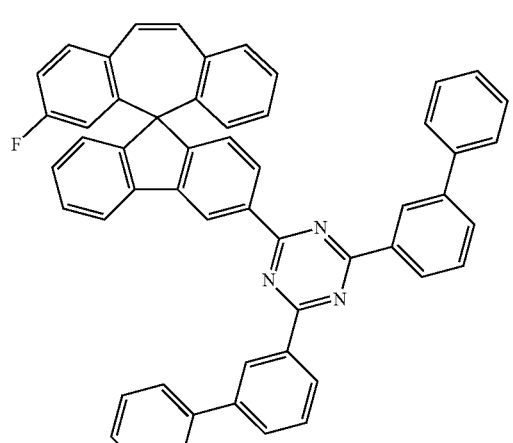  Compound 28 | 78 | $C_{54}H_{34}FN_3$ (743.87) |

TABLE 8-continued intermediates adopted to prepare Compounds 1 to 31.

| No. | Method | Intermediate C | Intermediate D | Chemical Structure of Claimed Compound | Yield (%) | Formula/ Mass (M+) |
|---|---|---|---|---|---|---|
| SGM 843 | A | C2 | D25 | 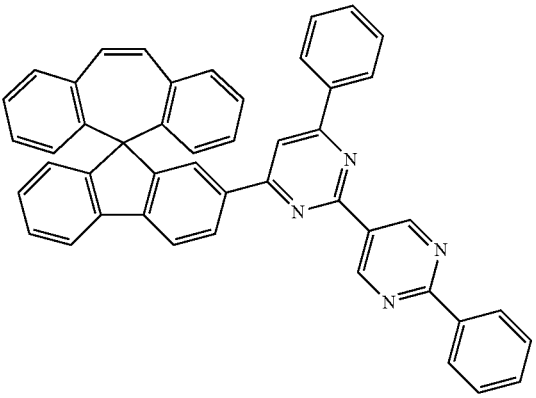<br>Compound 29 | 71 | $C_{47}H_{30}N_3$ (650.77) |
| SGM 195 | A | C10 | D23 | 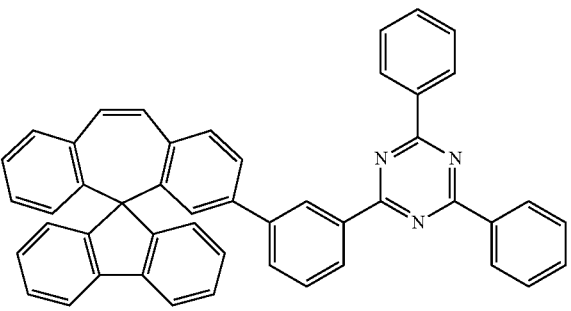<br>Compound 30 | 85 | $C_{48}H_{31}N_3$ (649.78) |
| SGM 218 | A | C11 | D22 | 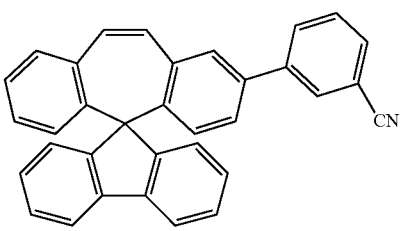<br>Compound 31 | 84 | $C_{34}H_{21}N$ (443.54) |

Modifications of Compounds 1 to 31

In addition to the Compounds 1 to 31, one person skilled in the art can react any Intermediates C with any Intermediates D through a reaction mechanism similar to Scheme I-A or Scheme I-B to synthesize other desired claimed novel compounds.

Preparation of OLED Devices

A glass substrate coated with ITO layer (abbreviated in ITO substrate) in a thickness of 1500 Å was placed in distilled water containing a detergent dissolved therein, and was ultrasonically washed. The detergent was a product manufactured by Fischer Co., and the distilled water was distilled water filtered twice through a filter (Millipore Co.). After the ITO layer had been washed for 30 minutes, it was ultrasonically washed twice with distilled water for 10 minutes. After the completion of washing, the glass substrate was ultrasonically washed with isopropyl alcohol, acetone and methanol solvents and then dried, after which it was transported to a plasma cleaner. Then the substrate was cleaned with oxygen plasma for 5 minutes, and then transferred to a vacuum evaporator.

After that, various organic materials and metal materials were sequentially deposited on the ITO substrate to obtain the OLED device of Examples and Comparative Examples as stated above. The vacuum degree during the deposition was maintained at $1\times10^{-6}$ to $3\times10^{-7}$ torr. Herein, the ITO substrate was deposited with a first hole injection layer (HIL-1), a second hole injection layer (HIL-2), a first hole transporting layer (HTL-1), a second hole transporting layer (HTL-2), a blue/green/red emission layer (BEL/GEL/REL), an electron transporting layer (ETL), an electron injection layer (EIL), and a cathode (Cthd).

Herein, HAT was a material for forming HIL-1 and HID; HI-2 was a material for forming HIL-2; HT-1 and HT-2 were respectively materials for forming HTL-1 and HTL-2; novel compounds of the Examples and ET of the Comparative Examples were materials for forming ETL; Liq was a material for forming ETD and EIL. RH/GH/BH each was host material for forming REL/GEL/BEL, and RD/GD/BD each was dopant for forming REL/GEL/BEL. The detailed chemical structures of foresaid commercial materials used in the OLED devices were listed in Table 9.

TABLE 9 chemical structures of commercial materials for OLED devices.

TABLE 9-continued chemical structures of commercial materials for OLED devices.

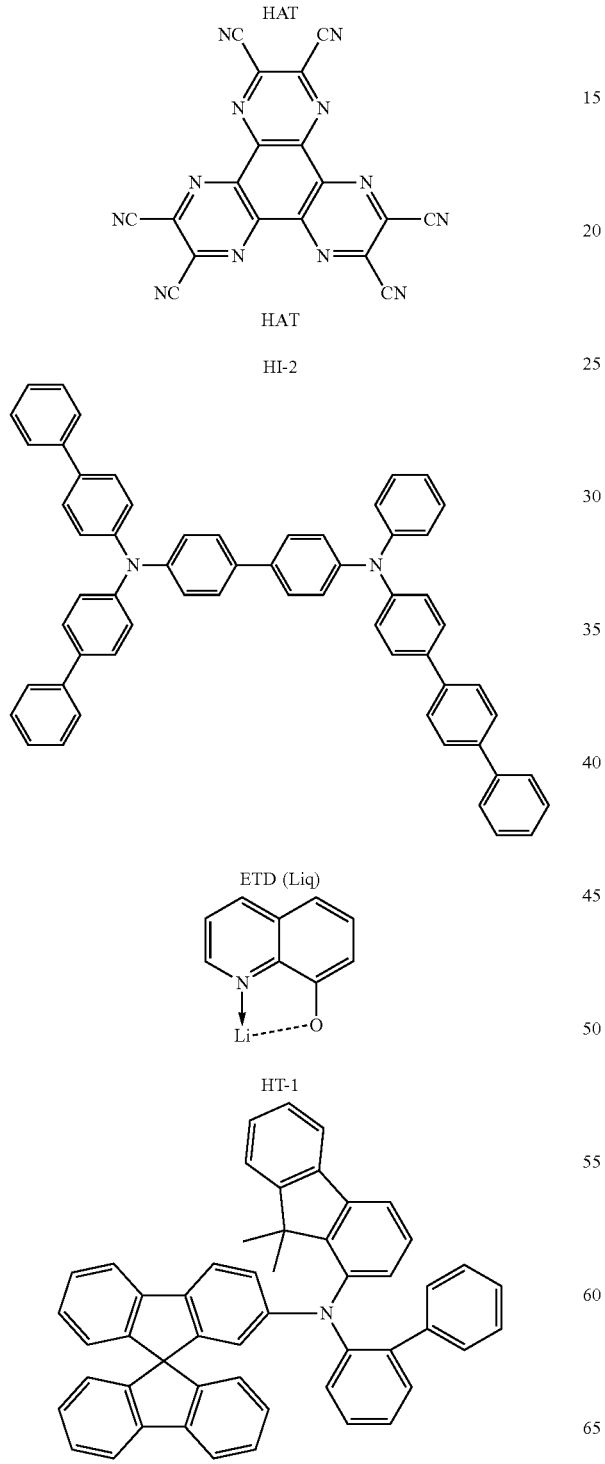
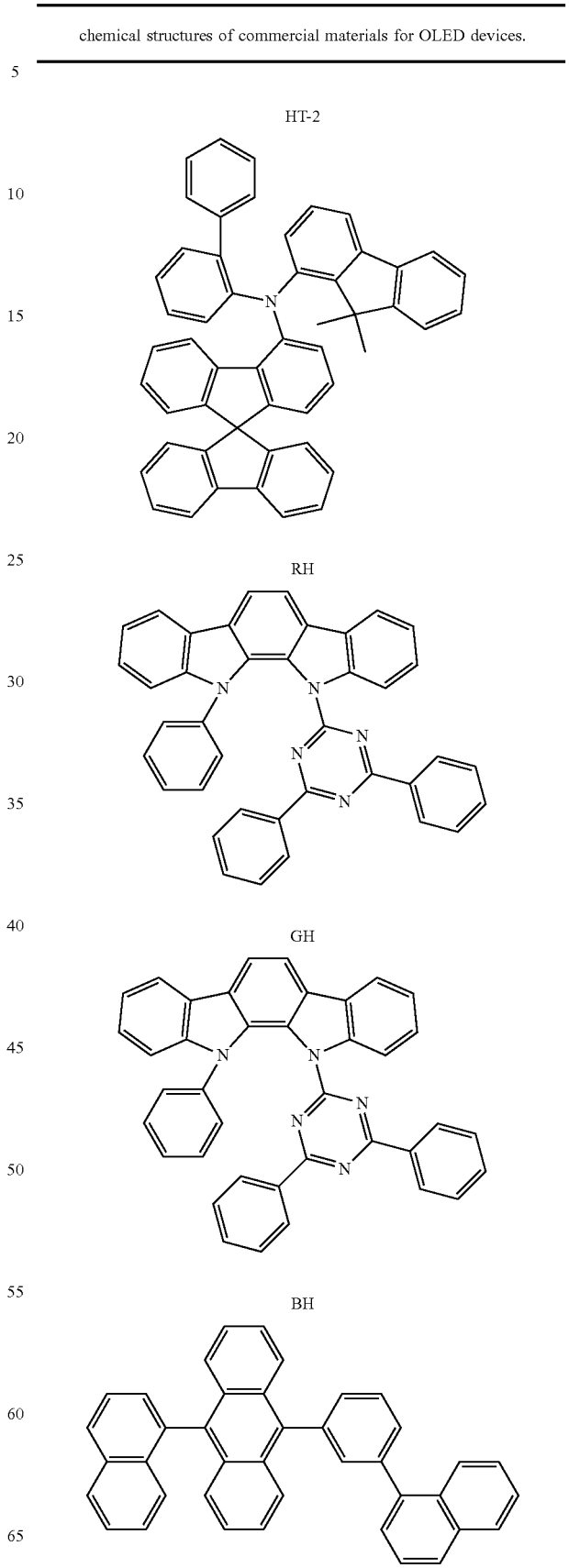

TABLE 9-continued chemical structures of commercial materials for OLED devices.

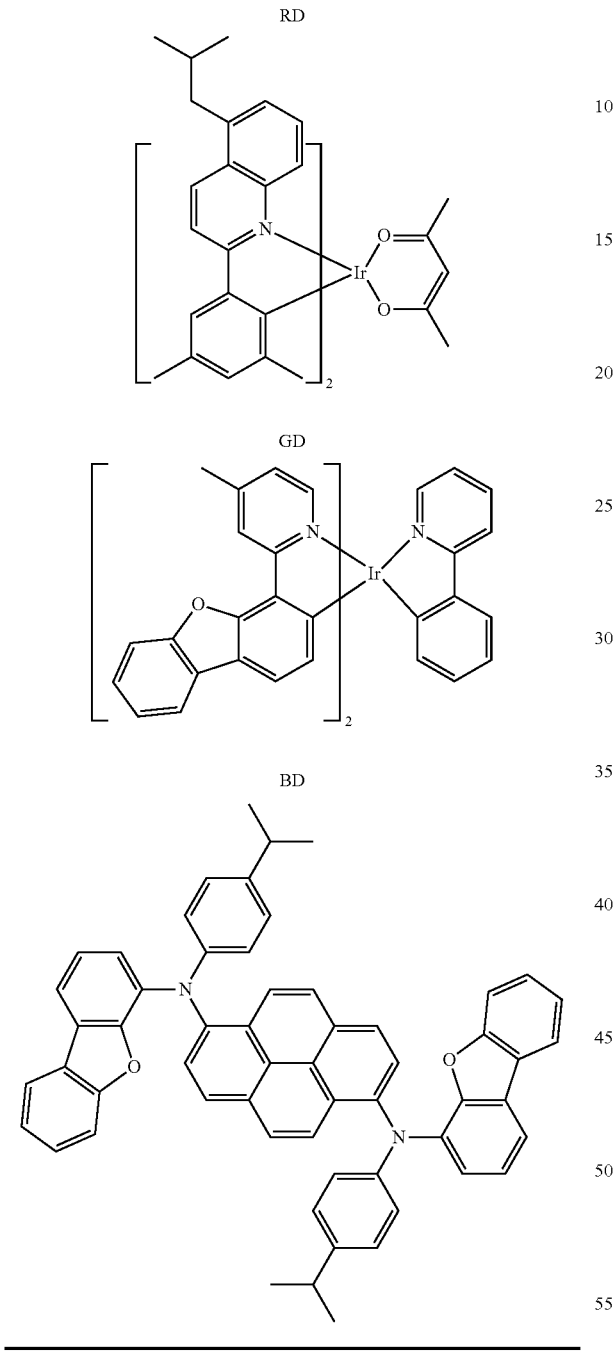

The main difference of the OLED devices between Examples and Comparative Examples was that the material of ETL of OLED in following Comparative Example was made of compounds of Comparative Examples but the material of ETL of OLED in following Examples was made of the novel compounds of the present invention were listed in Table 8. Specifically, the material of ETL of Examples 1 to 10 and compounds of Comparative Examples 1 to 4 used in OLED devices were listed in Table 10.

TABLE 10 the compounds used in ETL of OLED devices of Examples 1 to 10 and Comparative Examples 1 to 4.

Example 1
(Compound 1)
(SGM616)

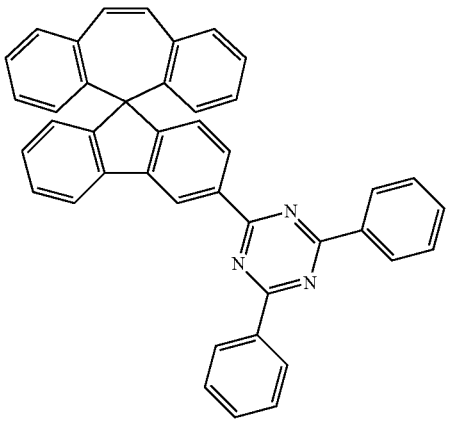 [SMILES: C1=Cc2ccccc2C2(c3ccccc31)c1ccccc1-c1cc(-c3nc(-c4ccccc4)nc(-c4ccccc4)n3)ccc12]

Example 2
(Compound 2)
(SGM619)

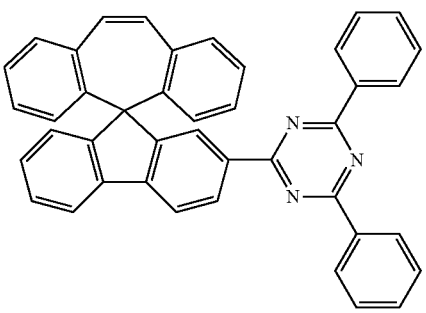 [SMILES: C1=Cc2ccccc2C2(c3ccccc31)c1ccccc1-c1ccc(-c3nc(-c4ccccc4)nc(-c4ccccc4)n3)cc12]

Example 3
(Compound 13)
(SGM183)

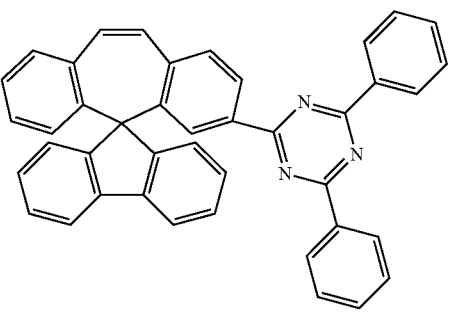 [SMILES: C1=Cc2ccc(-c3nc(-c4ccccc4)nc(-c4ccccc4)n3)cc2C2(c3ccccc31)c1ccccc1-c1ccccc12]

TABLE 10-continued
the compounds used in ETL of OLED devices of Examples 1 to 10 and Comparative Examples 1 to 4.
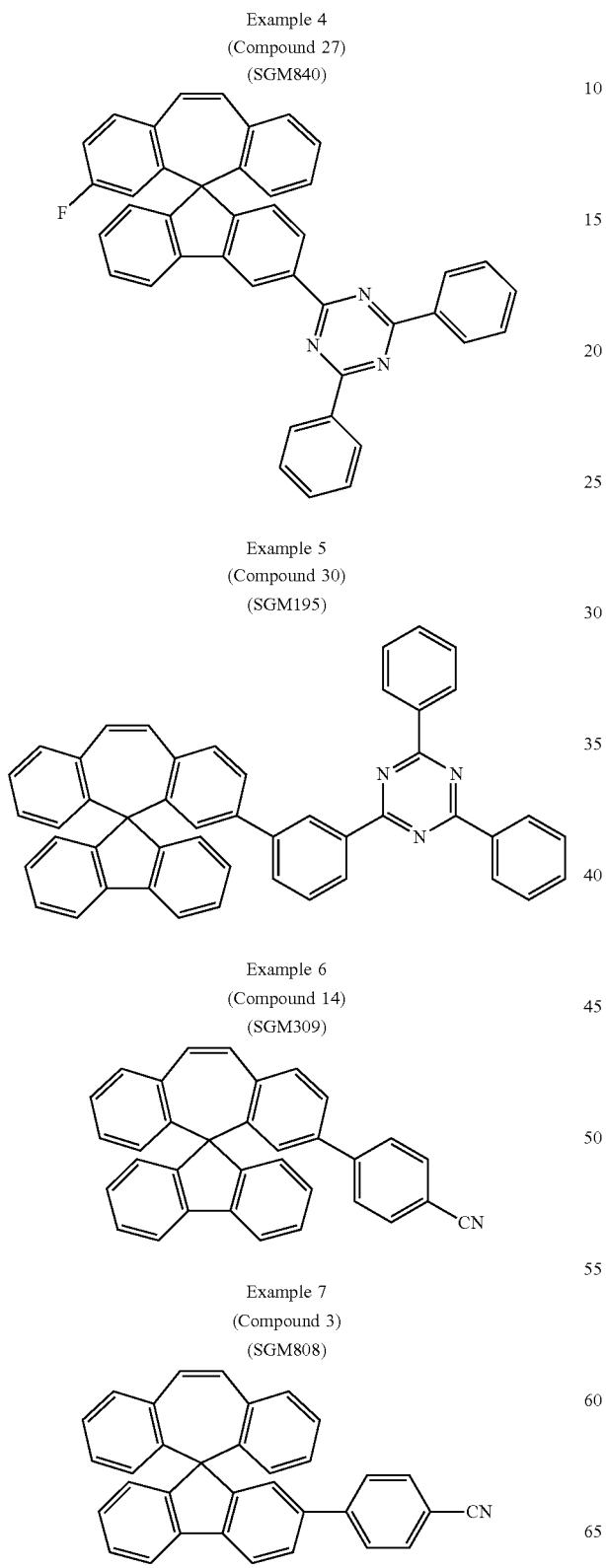
Example 4
(Compound 27)
(SGM840)
Example 5
(Compound 30)
(SGM195)
Example 6
(Compound 14)
(SGM309)
Example 7
(Compound 3)
(SGM808)
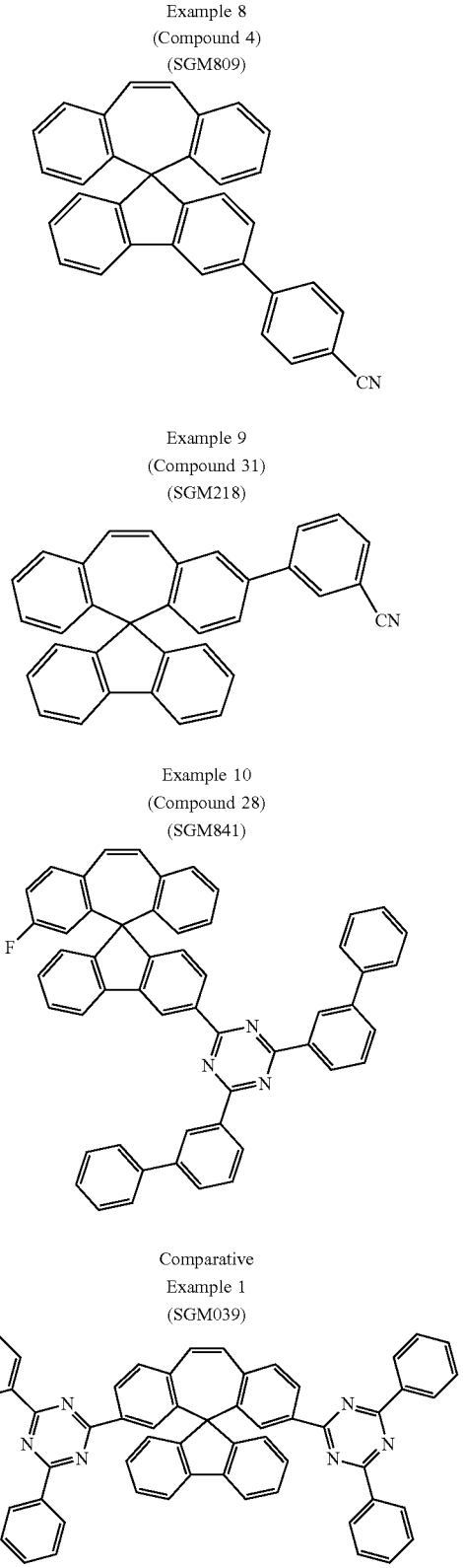
Example 8
(Compound 4)
(SGM809)
Example 9
(Compound 31)
(SGM218)
Example 10
(Compound 28)
(SGM841)
Comparative
Example 1
(SGM039)

TABLE 10-continued the compounds used in ETL of OLED devices of Examples 1 to 10 and Comparative Examples 1 to 4.

Comparative Example 2 (SGM026)

Comparative Example 3 (SGM030)

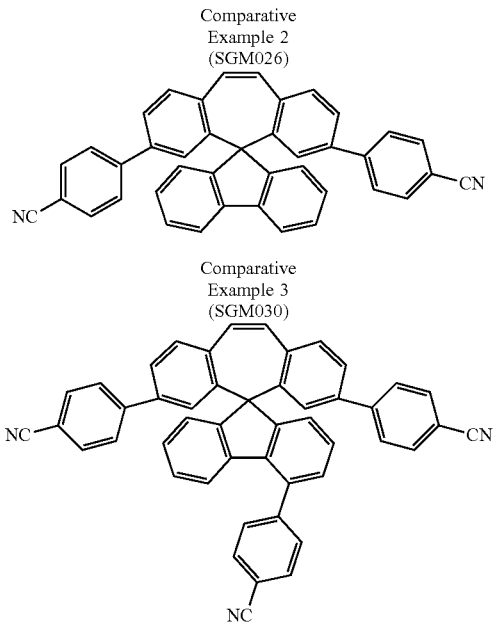

Comparative Example 4 (SGM131)

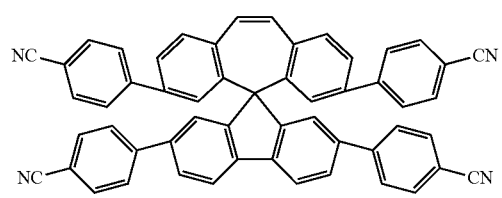 [SMILES: N#Cc1ccc(-c2ccc3c(c2)C2(c4cc(-c5ccc(C#N)cc5)ccc4C=C3)c3cc(-c4ccc(C#N)cc4)ccc3-c3ccc(-c4ccc(C#N)cc4)cc32)cc1]

To prepare the red, green, and blue OLED devices, multiple organic layers were respectively deposited on the ITO substrate according to the sequence, the materials, and the thicknesses of the organic layers in red, green, and blue OLED devices were also listed in Tables 11 to 13.

TABLE 11 coating sequence, materials, and thickness of the organic layers in red OLED device.

| | Layer | | | | | | | | | | |
|---|---|---|---|---|---|---|---|---|---|---|---|
| | HI-1 | HI-2 | HID | HTL-1 | HTL-2 | REL | RD | ETL | ETD | EIL | Cthd |
| Materials | HAT | HI-2 | HAT | HT-1 | HT-2 | RH | RD | ET | Liq | Liq | Al |
| Thickness (Å) | 100 | 2200 | — | 100 | 100 | 300 | — | 350 | — | 15 | 1500 |
| Dopant ratio | — | — | 5.0% | — | — | — | 3.5% | — | 35.0% | — | — |
| Coating Sequence | 1 | 2 | 2 | 3 | 4 | 5 | 5 | 6 | 6 | 7 | 8 |

TABLE 12 coating sequence, materials, and thickness of the layers in green OLED device.

| | Layer | | | | | | | | | | |
|---|---|---|---|---|---|---|---|---|---|---|---|
| | HI-1 | HI-2 | HID | HTL-1 | HTL-2 | GEL | GD | ETL | ETD | EIL | Cthd |
| Materials | HAT | HI-2 | HAT | HT-1 | HT-2 | GH | GD | ET | Liq | Liq | Al |
| Thickness (Å) | 100 | 1400 | — | 100 | 100 | 400 | — | 350 | — | 15 | 1500 |
| Dopant ratio | — | — | 5.0% | — | — | — | 10.0% | — | 35.0% | — | — |
| Coating Sequence | 1 | 2 | 2 | 3 | 4 | 5 | 5 | 6 | 6 | 7 | 8 |

TABLE 13 coating sequence, materials, and thickness of the layers in blue OLED device.

| | Layer | | | | | | | | | | |
|---|---|---|---|---|---|---|---|---|---|---|---|
| | HI-1 | HIL-2 | HID | HTL-1 | HTL-2 | BEL | BD | ETL | ETD | EIL | Cthd |
| Materials | HAT | HI-2 | HAT | HT-1 | H-T2 | BH | BD | ET | Liq | Liq | Al |
| Thickness (Å) | 100 | 750 | — | 100 | 100 | 250 | — | 250 | — | 15 | 1500 |
| Dopant ratio | — | — | 5.0% | — | — | — | 3.5% | — | 35.0% | — | — |
| Coating Sequence | 1 | 2 | 2 | 3 | 4 | 5 | 5 | 6 | 6 | 7 | 8 |

Performance of OLED Device

To evaluate the performance of OLED devices, red, green, and blue OLED devices were measured by PR650 as photometer and Keithley 2400 as power supply. Color coordinates (x,y) were determined according to the CIE chromaticity scale (Commission Internationale de L'Eclairage, 1931). The results were shown in Table 14. For the blue and red OLED devices, the data were collected at 1000 nits. For the green OLED devices, the data were collected at 3000 nits.

TABLE 14 materials of ETL, colors, CIEs, voltages, and current efficiencies of OLED devices of Examples 1 to 10 (E1 to E10) and Comparative Examples 1 to 4 (C1 to C4).

| | Compound No. | Color CIE (x, y) | Voltage (V) | Efficiency (cd/A) | EQE (%) |
|---|---|---|---|---|---|
| E1 | Compound 1 (SGM616) | B (0.129, 0.154) | 4.04 | 11.3 | 7.89 |
| | | G (0.310, 0.640) | 3.03 | 74.6 | 18.36 |
| | | R (0.658, 0.340) | 3.51 | 24.1 | 16.60 |
| E2 | Compound 2 (SGM619) | B (0.129, 0.148) | 3.97 | 11.0 | 7.88 |
| | | G (0.318, 0.637) | 2.93 | 74.3 | 18.54 |
| | | R (0.660, 0.339) | 3.44 | 24.2 | 17.30 |
| E3 | Compound 13 (SGM183) | B (0.129, 0.159) | 3.92 | 11.5 | 7.83 |
| | | G (0.341, 0.621) | 3.06 | 72.2 | 19.87 |
| | | R (0.666, 0.332) | 3.69 | 22.4 | 18.81 |
| E4 | Compound 27 (SGM840) | B (0.130, 0.153) | 4.4 | 8.43 | 46.25 |
| | | G (0.317, 0.637) | 3.17 | 76.2 | 16.95 |
| | | R (0.656, 0.341) | 4.45 | 25.6 | 19.02 |
| E5 | Compound 30 SGM195 | B (0.135, 0.158) | 4.86 | 11.1 | 7.80 |
| | | G (0.339, 0.624) | 3.20 | 77.9 | 19.92 |
| | | R (0.666, 0.332) | 4.21 | 20.1 | 17.8 |
| E6 | Compound 14 (SGM309) | B (0.130, 0.145) | 3.65 | 10.5 | 7.02 |
| | | G (0.330, 0.630) | 2.91 | 78.2 | 18.5 |
| | | R (0.662, 0.336) | 3.33 | 24.5 | 17.11 |
| E7 | Compound 3 (SGM808) | B (0.130, 0.146) | 4.06 | 10.1 | 6.98 |
| | | G (0.330, 0.629) | 3.06 | 77.5 | 18.85 |
| E8 | Compound 4 (SGM809) | B (0.130, 0.145) | 4.36 | 9.57 | 6.79 |
| | | G (0.319, 0.636) | 3.08 | 76.8 | 18.9 |
| | | R (0.661, 0.337) | 3.61 | 24.9 | 17.65 |
| E9 | Compound 31 SGM218 | B (0.136, 0.158) | 4.43 | 12.25 | 8.15 |
| | | G (0.318, 0.638) | 3.14 | 77.5 | 18.81 |
| | | R (0.6 6, 0.337) | 3.57 | 22.6 | 18.65 |
| E10 | Compound 28 (SGM841) | B (0.129, 0.157) | 4.78 | 9.83 | 6.83 |
| | | G (0.319, 0.636) | 5.17 | 79.4 | 17.98 |
| | | R (0.658, 0.340) | 5.15 | 25.9 | 19.21 |
| C1 | SGM039 | B (0.129, 0.164) | 5.13 | 7.83 | 6.17 |
| | | G (0.338, 0.621) | 3.36 | 71.2 | 16.73 |
| | | R (0.668, 0.330) | 4.10 | 17.4 | 15.89 |
| C2 | SGM026 | B (0.128, 0.193) | 4.97 | 7.87 | 6.25 |
| | | G (0.332, 0.629) | 3.52 | 75.9 | 18.2 |
| | | R (0.651, 0.341) | 4.01 | 16.3 | 14.78 |
| C3 | SGM030 | B (0.130, 0.145) | 4.89 | 6.08 | 4.27 |
| | | G (0.312, 0.639) | 3.23 | 71.6 | 18.04 |
| | | R (0.661, 0.338) | 3.76 | 21.0 | 12.79 |

TABLE 14-continued materials of ETL, colors, CIEs, voltages, and current efficiencies of OLED devices of Examples 1 to 10 (E1 to E10) and Comparative Examples 1 to 4 (C1 to C4).

| | Compound No. | Color CIE (x, y) | Voltage (V) | Efficiency (cd/A) | EQE (%) |
|---|---|---|---|---|---|
| C4 | SGM131 | B (0.130, 0.150) | 5.67 | 4.01 | 2.62 |
| | | G (0.316, 0.638) | 3.51 | 70.4 | 17.48 |
| | | R (0.661, 0.338) | 4.00 | 20.8 | 14.82 |

As shown in Table 14, adopting the novel compounds of the present invention as the electron transport material can reduce the driving voltage and improve the current efficiency and external quantum efficiency of the red, green, or blue OLEDs.

Comparing Examples 1 to 5 with Comparative Example 1 or comparing Examples 6 to 9 with Comparative Examples 2 to 4, it demonstrated that a compound attached with only one specific group (L-G) on the upper part or the lower part of the main skeletal structures is suitable as an electron transport material for any color OLEDs, and allows the OLEDs using the same to have low driving voltage and improved current efficiency and EQE.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A compound represented by any one of the following Formulae:

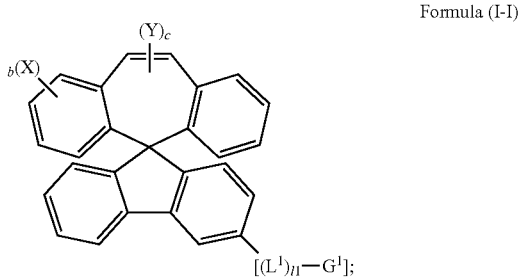

Formula (I-I)

Formula (I-II)
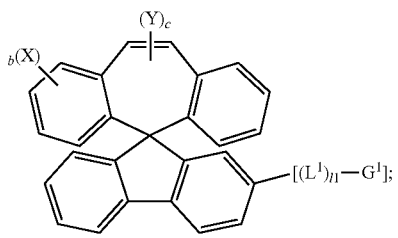

Formula (I-III)
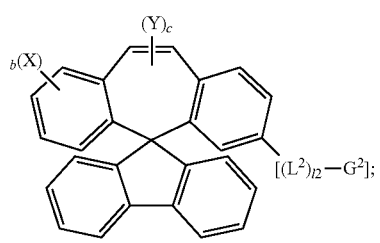

Formula (I-IV)
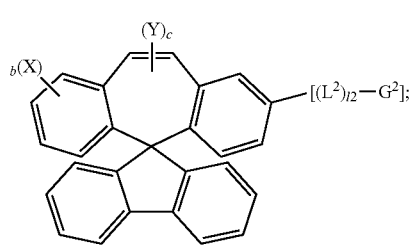

Formula (I-V)
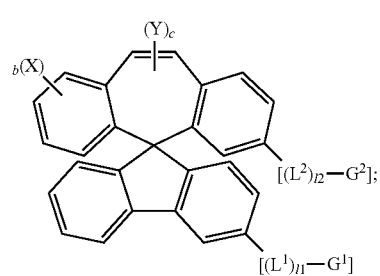

Formula (I-VI)
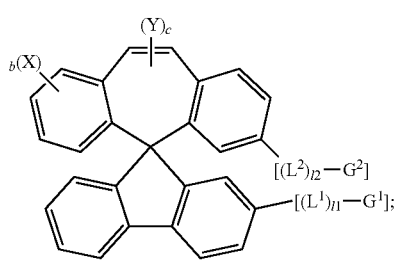

Formula (I-VII)
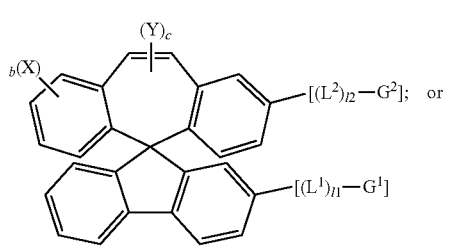 or

Formula (I-VIII)
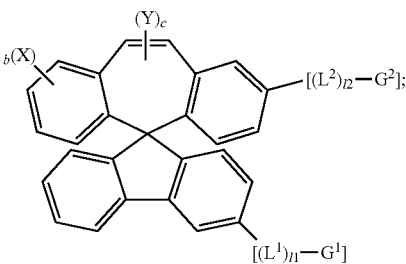

wherein, l1 and l2 are each independently an integer from 0 to 3;

$L^1$ and $L^2$ are each independently a substituted or unsubstituted arylene group having 6 to 60 carbon atoms;

$G^1$ and $G^2$ are each independently selected from the group consisting of: a heteroaryl group having 3 to 60 ring carbon atoms, an alkyl group having 1 to 40 carbon atoms and substituted with at least one functional group, an alkenyl group having 2 to 40 carbon atoms and substituted with at least one functional group, an alkynyl group having 2 to 40 carbon atoms and substituted with at least one functional group, a cycloalkyl group having 3 to 60 ring carbon atoms and substituted with at least one functional group, a heterocycloalkyl group having 3 to 60 ring carbon atoms and substituted with at least one functional group, an alkoxy group having 1 to 40 carbon atoms and substituted with at least one functional group, an aryl group having 6 to 60 ring carbon atoms and substituted with at least one functional group, an aryloxy group having 6 to 60 ring carbon atoms and substituted with at least one functional group, an alkylsilyl group having 1 to 40 carbon atoms and substituted with at least one functional group, an arylsilyl group having 6 to 60 ring carbon atoms and substituted with at least one functional group, an alkylboron group having 1 to 40 carbon atoms and substituted with at least one functional group, an arylboron group having 6 to 60 ring carbon atoms and substituted with at least one functional group, a phosphine group having 1 to 40 carbon atoms and substituted with at least one functional group, and a phosphine oxide group having 1 to 40 carbon atoms and substituted with at least one functional group, any isomeric groups thereof, and any deuterated analogs thereof, wherein the functional group is selected from the group consisting of: a cyano group, a nitro group, a trifluoromethyl group, a fluoro group, and a chloro group;

b is an integer of 0 to 4;

X is selected from the group consisting of: a deuterium atom, a fluoro group, a chloro group, a bromo group, an unsubstituted aryl group having 6 to 60 carbon atoms, an unsubstituted alkyl group having 1 to 12 carbon atoms, an unsubstituted alkenyl group having 2 to 12 carbon atoms, and an unsubstituted alkynyl group having 2 to 12 carbon atoms;

c is an integer of 0 to 2;

Y is selected from the group consisting of: a deuterium atom, a substituted or unsubstituted aryl group having 6 to 60 carbon atoms, a substituted or unsubstituted heteroaryl group having 3 to 60 carbon atoms, and any deuterated analogs thereof.

2. The compound as claimed in claim 1, wherein the heteroaryl groups having 3 to 60 ring carbon atoms of G¹ and G² are each selected from the group consisting of: a substituted or unsubstituted furyl group, a substituted or unsubstituted pyrrolyl group, a substituted or unsubstituted thiophenyl group, a substituted or unsubstituted imidazolyl group, a substituted or unsubstituted pyrazolyl group, a substituted or unsubstituted triazolyl group, a substituted or unsubstituted tetrazolyl group, a substituted or unsubstituted oxazolyl group, a substituted or unsubstituted isoxazolyl group, a substituted or unsubstituted thiazolyl group, a substituted or unsubstituted isothiazolyl group, a substituted or unsubstituted oxadiazolyl group, a substituted or unsubstituted thiadiazolyl group; a substituted or unsubstituted pyridyl group, a substituted or unsubstituted pyridazinyl group, a substituted or unsubstituted pyrimidinyl group, a substituted or unsubstituted pyrazinyl group, a substituted or unsubstituted triazinyl group; a substituted or unsubstituted indolyl group, a substituted or unsubstituted isoindolyl group, a substituted or unsubstituted benzofuranyl group, a substituted or unsubstituted isobenzofuranyl group, a substituted or unsubstituted benzothiophenyl group, a substituted or unsubstituted isobenzothiophenyl group, a substituted or unsubstituted indolizinyl group, a substituted or unsubstituted quinolizinyl group, a substituted or unsubstituted quinolyl group, a substituted or unsubstituted isoquinolyl group, a substituted or unsubstituted cinnolyl group, a substituted or unsubstituted phthalazinyl group, a substituted or unsubstituted quinazolinyl group, a substituted or unsubstituted quinoxalinyl group, a substituted or unsubstituted benzimidazolyl group, a substituted or unsubstituted benzoxazolyl group, a substituted or unsubstituted benzothiazolyl group, a substituted or unsubstituted indazolyl group, a substituted or unsubstituted benzisoxazolyl group, a substituted or unsubstituted benzisothiazolyl group; a substituted or unsubstituted dibenzofuranyl group, a substituted or unsubstituted dibenzothiophenyl group, a substituted or unsubstituted carbazolyl group, a substituted or unsubstituted biscarbazolyl group, a substituted or unsubstituted coumarinyl group, a substituted or unsubstituted chromenyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted phenothiazinyl group, a substituted or unsubstituted phenoxazinyl group, a substituted or unsubstituted azatriphenylenyl group, a substituted or unsubstituted diazatriphenylenyl group, a substituted or unsubstituted xanthenyl group, a substituted or unsubstituted azacarbazolyl group, a substituted or unsubstituted azadibenzofuranyl group, a substituted or unsubstituted azadibenzothiophenyl group, a substituted or unsubstituted benzofuranobenzothiophenyl group, a substituted or unsubstituted benzothienobenzothiophenyl group, a substituted or unsubstituted dibenzofuranonaphthyl group, a substituted or unsubstituted dibenzothienonaphthyl group, a substituted or unsubstituted dinaphthothienothiophenyl group, a substituted or unsubstituted dinaphtho carbazolyl group, a substituted or unsubstituted dibenzo[b,f]azepin group, a substituted or unsubstituted tribenzo[b,d,f]azepin group, a substituted or unsubstituted dibenzo[b,f]oxepin group, a substituted or unsubstituted tribenzo[b,d,f]oxepin group, any isomeric groups thereof, and any deuterated analogs thereof.

3. The compound as claimed in claim 1, wherein G¹ and G² are each independently selected from the group consisting of:

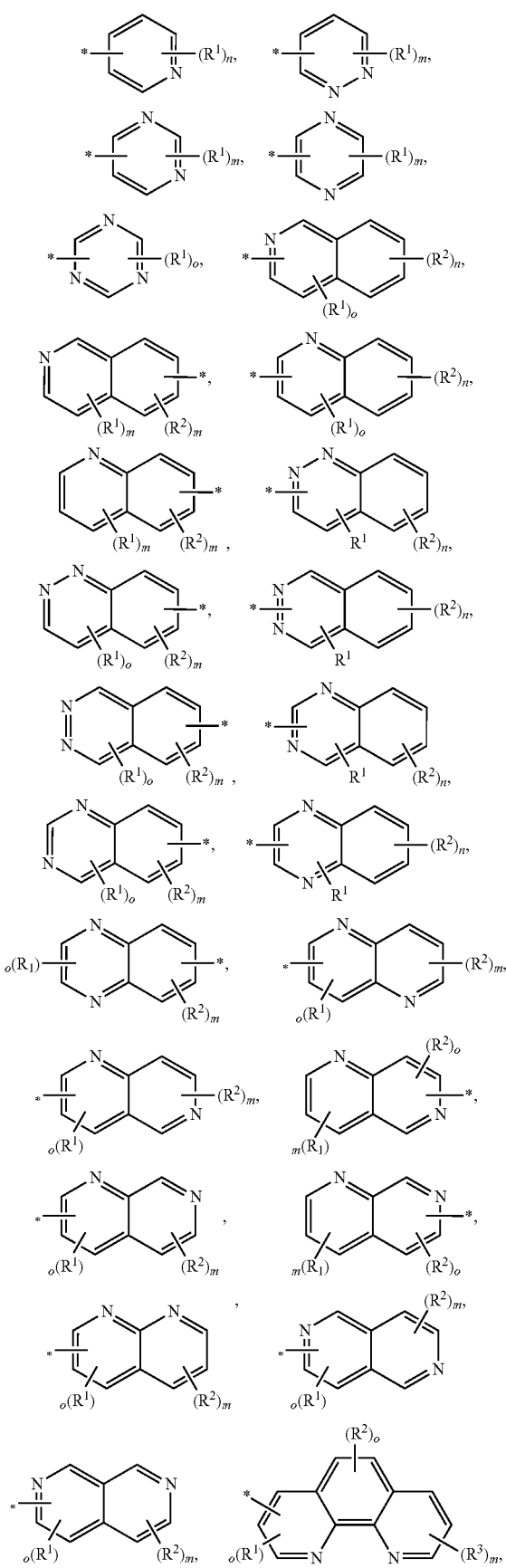

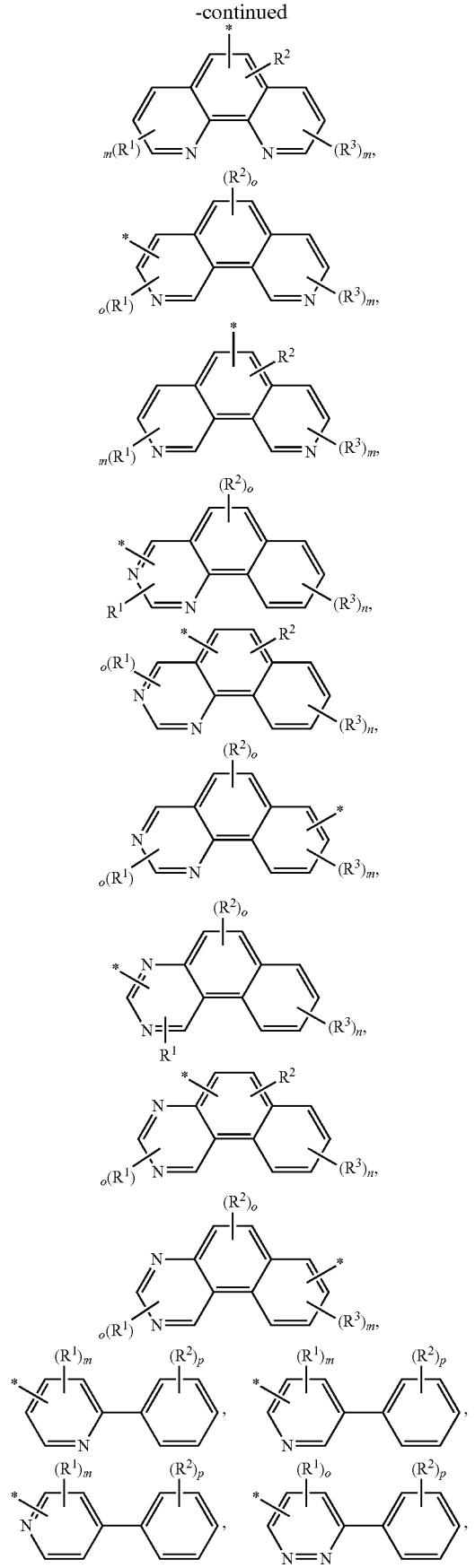
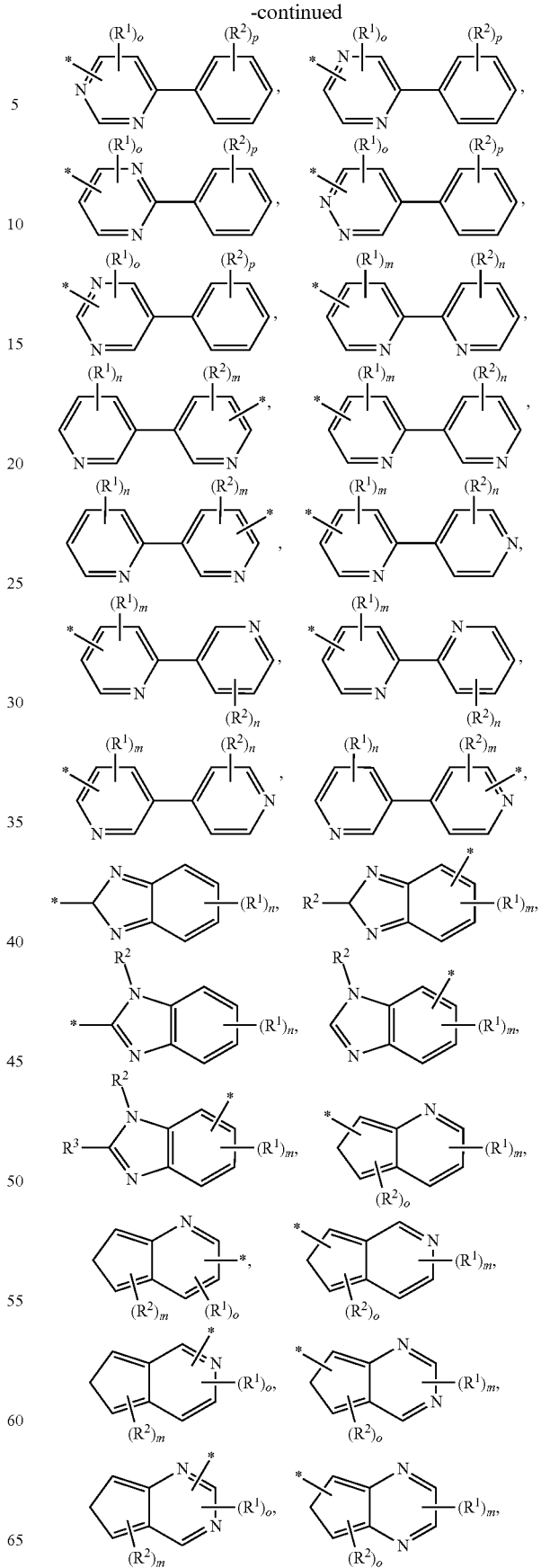

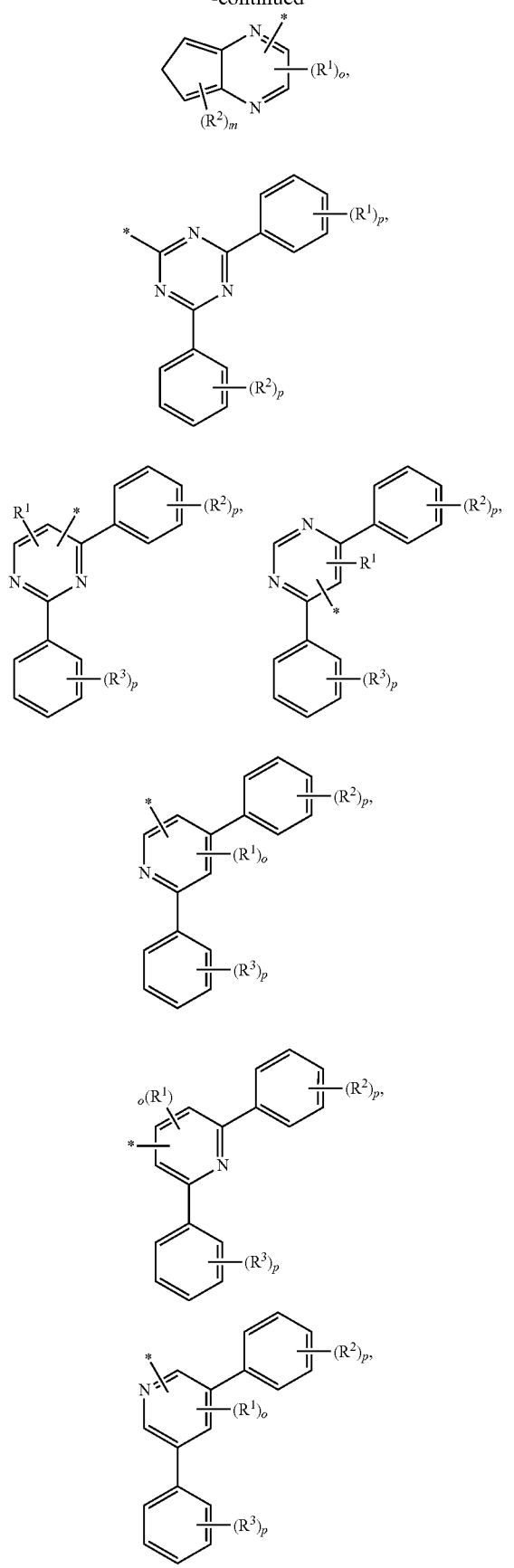
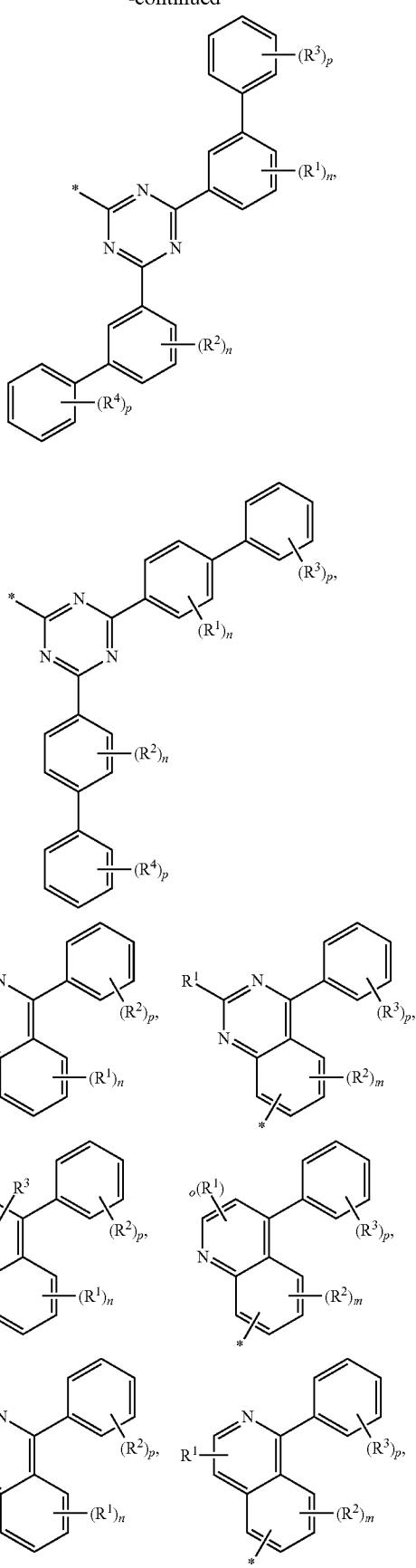

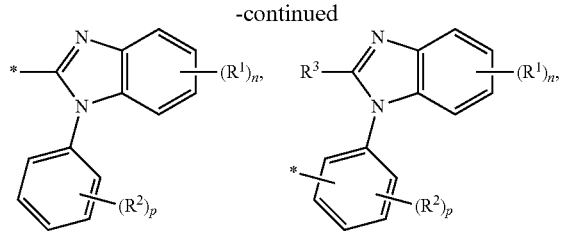
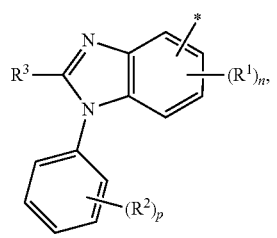
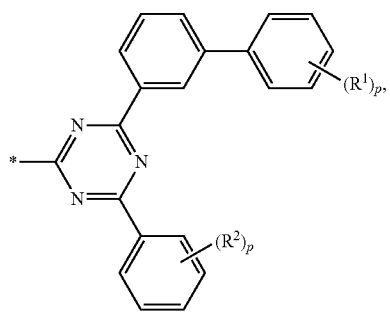
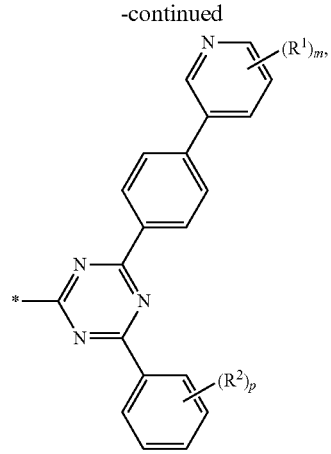
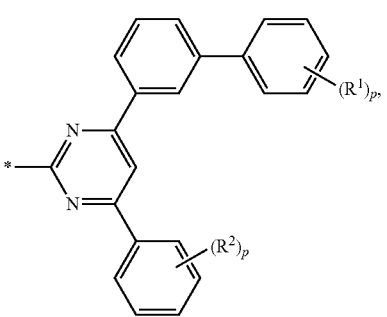
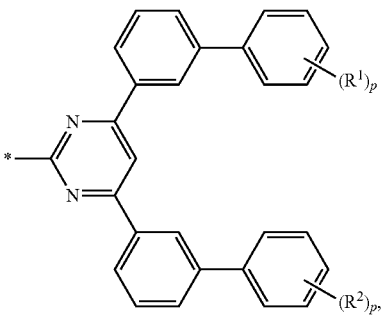
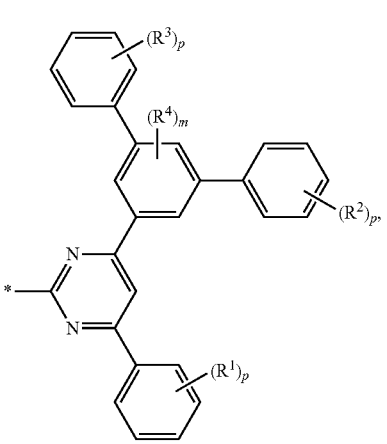

-continued
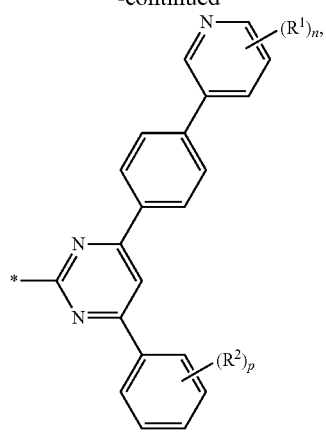
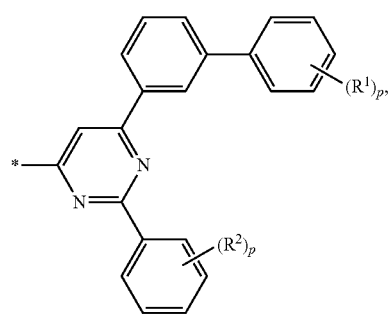
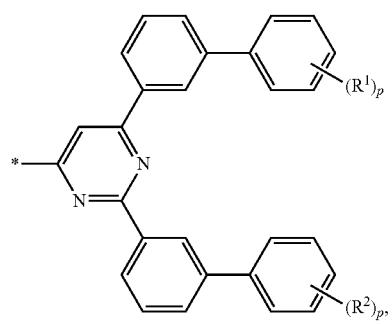
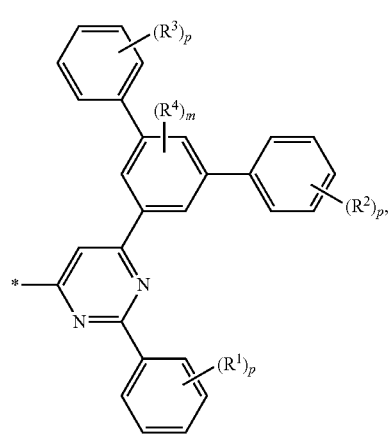
-continued
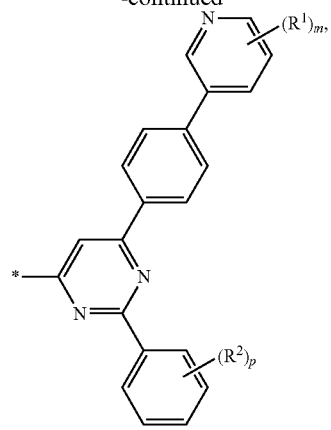
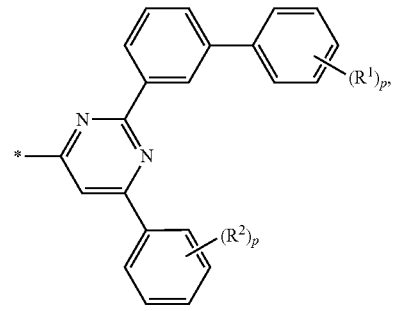
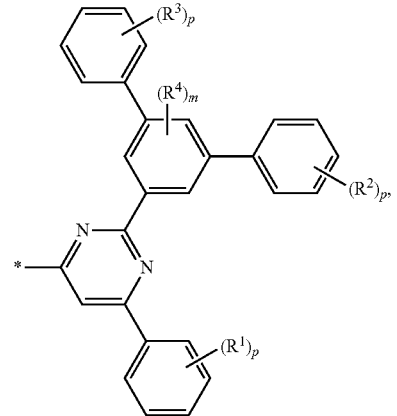
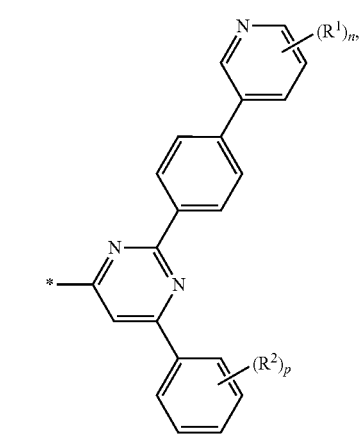

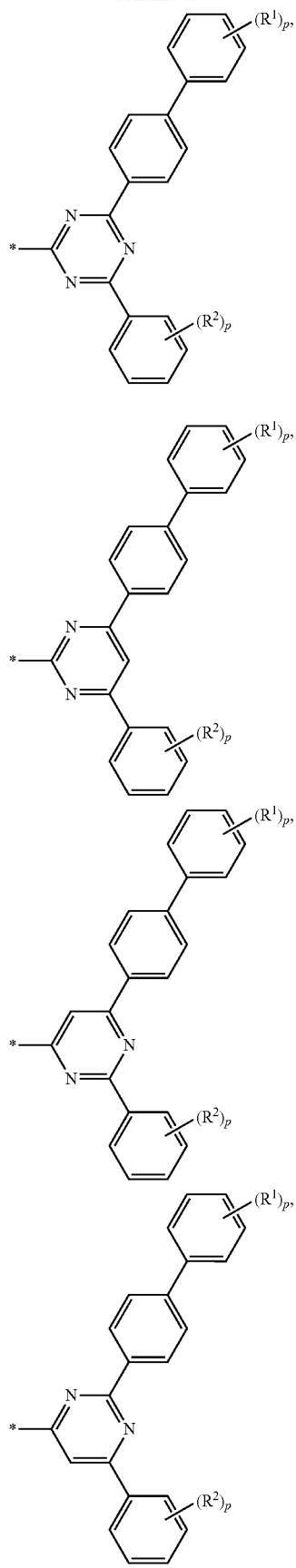
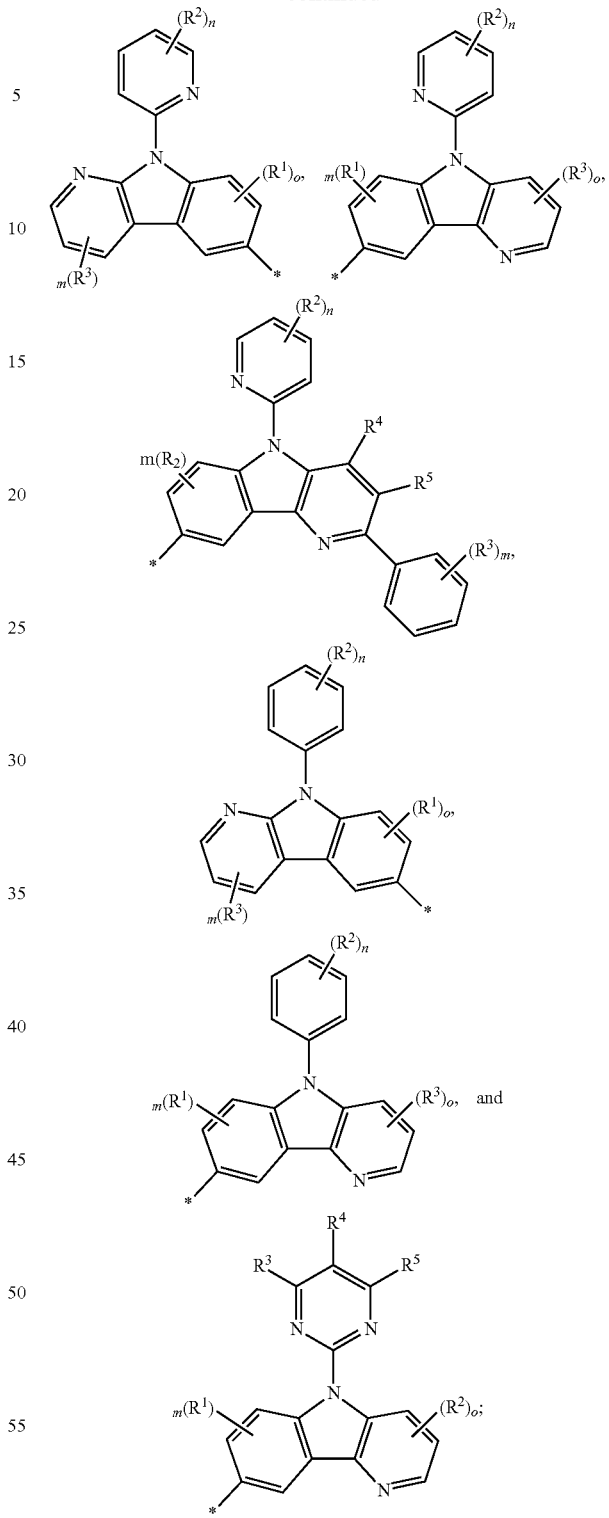
wherein o is an integer from 0 to 2; m is an integer from 0 to 3; n is an integer from 0 to 4; p is an integer from 0 to 5;
wherein $R^1$ to $R^4$ are each independently selected from the group consisting of: a deuterium atom, a halogen group, a cyano group, a nitro group, a trifluoromethyl group, an alkyl group having 1 to 12 carbon atoms, an alkenyl group having 2 to 12 carbon atoms, an alkynyl group having 2 to 12 carbon atoms, a cycloalkyl group having 3 to 30 carbon atoms, a heterocycloalkyl group having 3 to 30 carbon atoms, an aryl group having 6 to 30 carbon atoms, a heteroaryl group having 3 to 30 carbon atoms, an alkoxy group having 1 to 40 carbon atoms, an aryloxy group having 6 to 30 carbon atoms, an alkylsilyl group having 1 to 40 carbon atoms, an arylsilyl group having 6 to 30 carbon atoms, an alkylboron group having 1 to 30 carbon atoms, an arylboron group having 6 to 30 carbon atoms, a phosphine group having 1 to 30 carbon atoms, and a phosphine oxide group having 1 to 30 carbon atoms.

4. The compound as claimed in claim 1, wherein the aryl groups having 6 to 60 ring carbon atoms and substituted with at least one functional group of $G^1$ and $G^2$ are each selected from the group consisting of: a phenyl group substituted with the at least one functional group, a biphenyl group substituted with the at least one functional group, a terphenyl group substituted with the at least one functional group, a naphthyl group substituted with the at least one functional group, a phenanthryl group substituted with the at least one functional group, an anthracenyl group substituted with the at least one functional group, a benzanthryl group substituted with the at least one functional group, a fluorenyl group substituted with the at least one functional group, a chrycenyl group substituted with the at least one functional group, a fluoranthenyl group substituted with the at least one functional group, and any deuterated analogs thereof.

5. The compound as claimed in claim 1, wherein the aryl group having 6 to 60 carbon atoms and substituted with the at least one functional group of $G^1$ and $G^2$ are each independently selected from the group consisting of:

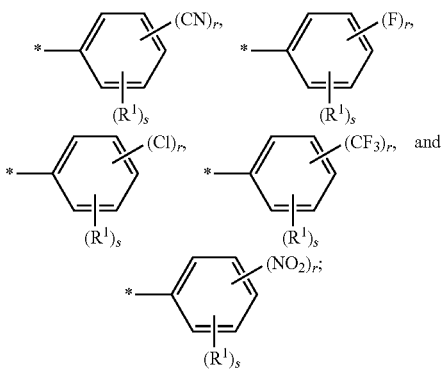

wherein r is an integer from 1 to 5; s is an integer from 0 to 4; the total of r and s is not more than 5;

wherein $R^1$ is selected from the group consisting of: a deuterium atom, an alkyl group having 1 to 12 carbon atoms, an alkenyl group having 2 to 12 carbon atoms, an alkynyl group having 2 to 12 carbon atoms, a cycloalkyl group having 3 to 30 carbon atoms, a heterocycloalkyl group having 3 to 30 carbon atoms, an aryl group having 6 to 30 carbon atoms, a heteroaryl group having 3 to 30 carbon atoms, an alkoxy group having 1 to 12 carbon atoms, an aryloxy group having 6 to 30 carbon atoms, an alkylsilyl group having 1 to 12 carbon atoms, an arylsilyl group having 6 to 30 carbon atoms, an alkylboron group having 1 to 12 carbon atoms and an arylboron group having 6 to 30 carbon atoms.

6. The compound as claimed in claim 1, wherein X is selected from the group consisting of: a deuterium atom, a fluoro group, a chloro group, a bromo group, a phenyl group, a biphenyl group, a terphenyl group, a naphthyl group, a phenanthryl group, an anthracenyl group, a benzanthryl group, a fluorenyl group, a chrycenyl group, a fluoranthenyl group, a deuterated phenyl group, a deuterated biphenyl group, a deuterated terphenyl group, a deuterated naphthyl group, a deuterated phenanthryl group, a deuterated anthracenyl group, a deuterated benzanthryl group, a deuterated fluorenyl group, a deuterated chrycenyl group, and a deuterated fluoranthenyl group.

7. The compound as claimed in claim 1, wherein Y is selected from the group consisting of: a deuterium atom, an unsubstituted phenyl group, an unsubstituted biphenyl group, an unsubstituted terphenyl group, an unsubstituted naphthyl group, an unsubstituted phenanthryl group, an unsubstituted anthracenyl group, an unsubstituted benzanthryl group, an unsubstituted fluorenyl group, an unsubstituted chrycenyl group, an unsubstituted fluoranthenyl group, a deuterated phenyl group, a deuterated biphenyl group, a deuterated terphenyl group, a deuterated naphthyl group, a deuterated phenanthryl group, a deuterated anthracenyl group, a deuterated benzanthryl group, a deuterated fluorenyl group, a deuterated chrycenyl group, a deuterated fluoranthenyl group, an unsubstituted furyl group, an unsubstituted pyrrolyl group, an unsubstituted thiophenyl group; an unsubstituted imidazolyl group, an unsubstituted pyrazolyl group, an unsubstituted triazolyl group, an unsubstituted tetrazolyl group, an unsubstituted oxazolyl group, an unsubstituted isoxazolyl group, an unsubstituted thiazolyl group, an unsubstituted isothiazolyl group, an unsubstituted oxadiazolyl group, an unsubstituted thiadiazolyl group; an unsubstituted pyridyl group, an unsubstituted pyridazinyl group, an unsubstituted pyrimidinyl group, an unsubstituted pyrazinyl group, an unsubstituted triazinyl group; an unsubstituted indolyl group, an unsubstituted isoindolyl group, an unsubstituted benzofuranyl group, an unsubstituted isobenzofuranyl group, an unsubstituted benzothiophenyl group, an unsubstituted isobenzothiophenyl group, an unsubstituted indolizinyl group, an unsubstituted quinolizinyl group, an unsubstituted quinolyl group, an unsubstituted isoquinolyl group, an unsubstituted cinnolyl group, an unsubstituted phthalazinyl group, an unsubstituted quinazolinyl group, an unsubstituted quinoxalinyl group, an unsubstituted benzimidazolyl group, an unsubstituted benzoxazolyl group, an unsubstituted benzothiazolyl group; an unsubstituted indazolyl group, an unsubstituted benzisoxazolyl group, an unsubstituted benzisothiazolyl group; an unsubstituted dibenzofuranyl group, an unsubstituted dibenzothiophenyl group, an unsubstituted carbazolyl group, an unsubstituted biscarbazolyl group, an unsubstituted coumarinyl group, an unsubstituted chromenyl group, an unsubstituted phenanthridinyl group, an unsubstituted acridinyl group, an unsubstituted phenanthrolinyl group, an unsubstituted phenazinyl group, an unsubstituted phenothiazinyl group, an unsubstituted phenoxazinyl group, an unsubstituted azatriphenylenyl group, an unsubstituted diazatriphenylenyl group, an unsubstituted xanthenyl group, an unsubstituted azacarbazolyl group, an unsubstituted azadibenzofuranyl group, an unsubstituted azadibenzothiophenyl group, an unsubstituted benzofuranobenzothiophenyl group, an unsubstituted benzothienobenzothiophenyl group, an unsubstituted dibenzofuranonaphthyl group, an unsubstituted dibenzothienonaphthyl group, an unsubstituted dinaphtho[2',3':2,3:2',3':6,7] carbazolyl group, an unsubstituted dibenzo[b,f]azepin group, an unsubstituted tribenzo[b,d,f]azepin group, an unsubstituted dibenzo[b,f]oxepin group, an unsubstituted tribenzo[b,d,f]oxepin group, a phenyl group substituted with a functional group, a biphenyl group substituted with a functional group, a terphenyl group substituted with a functional group, a naphthyl group substituted with a functional group, a phenanthryl group substituted with a functional group, an anthracenyl group substituted with a functional group, a benzanthryl group substituted with a functional group, a fluorenyl group substituted with a functional group, a chrycenyl group substituted with a functional group, and a fluoranthenyl group substituted with a functional group; wherein the functional group is selected from the group consisting of: a cyano group, a nitro group, a trifluoromethyl group, a fluoro group, and a chloro group.

8. The compound as claimed in claim 1, wherein $L^1$ and $L^2$ are each independently selected from the group consisting of:

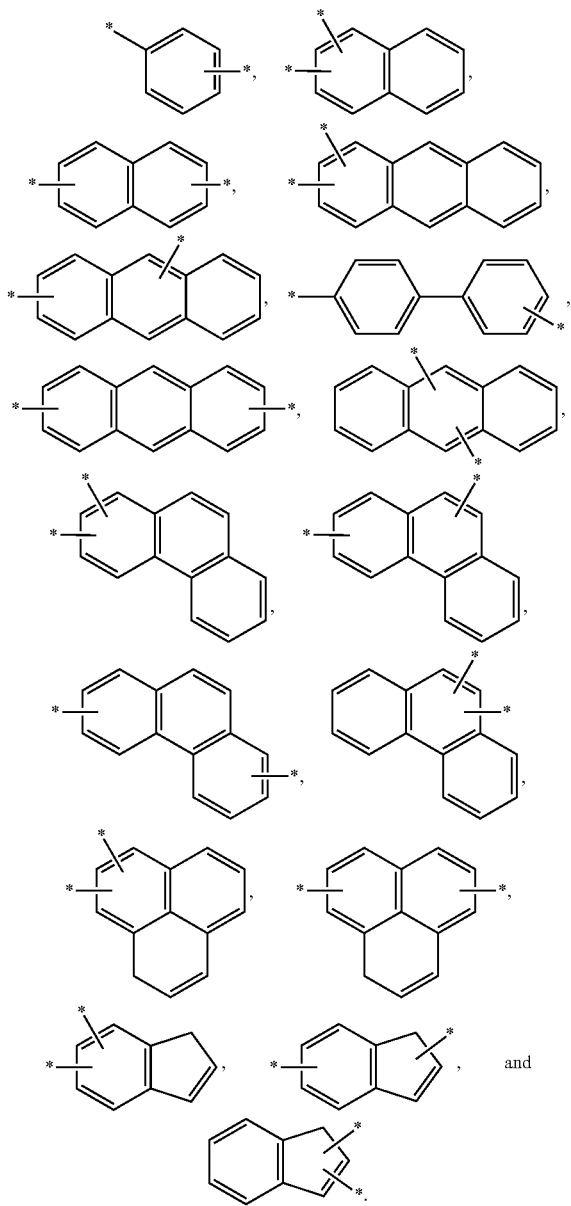

9. The compound as claimed in claim 1, wherein the compound is selected from the group consisting of:

Compound 1

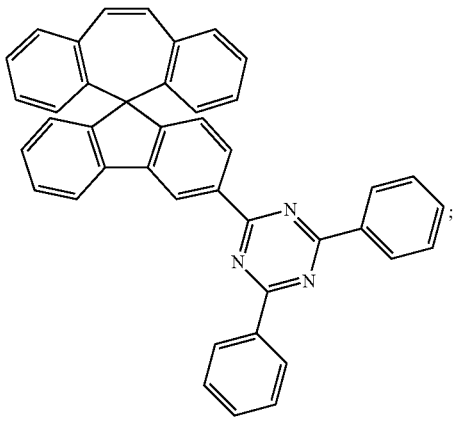

Compound 2

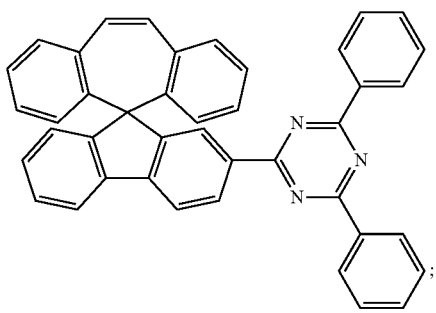

Compound 3

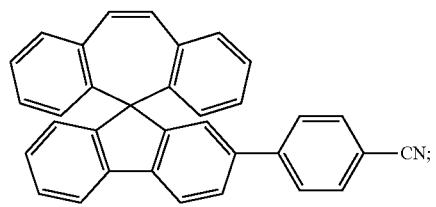

Compound 4

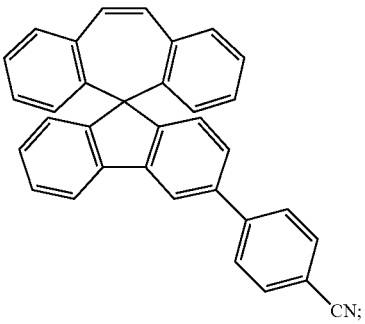

-continued
Compound 5
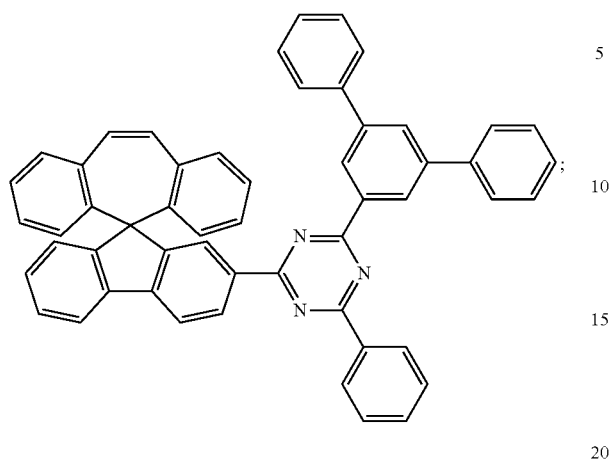
Compound 6
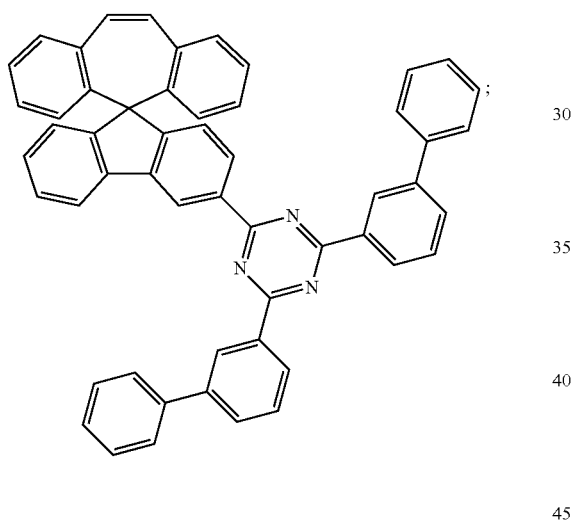
Compound 7
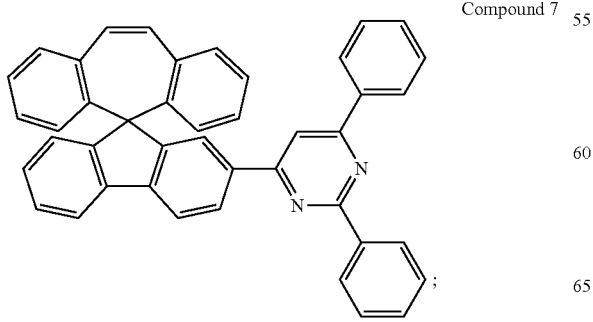
-continued
Compound 8
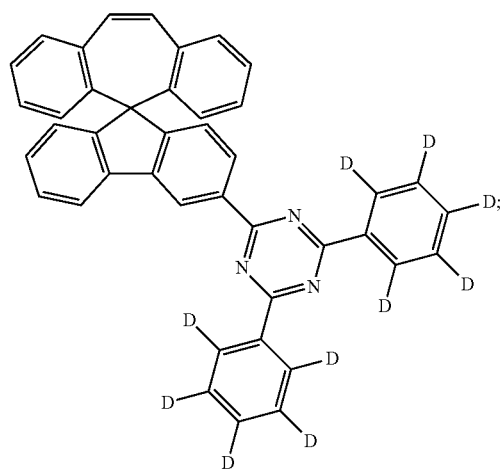
Compound 9
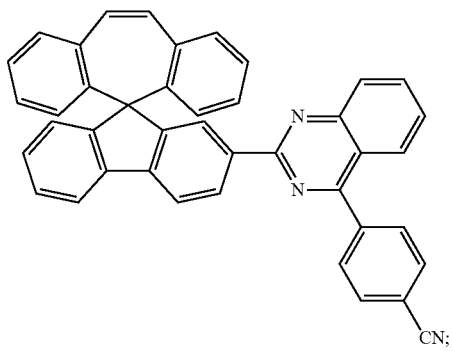
Compound 10
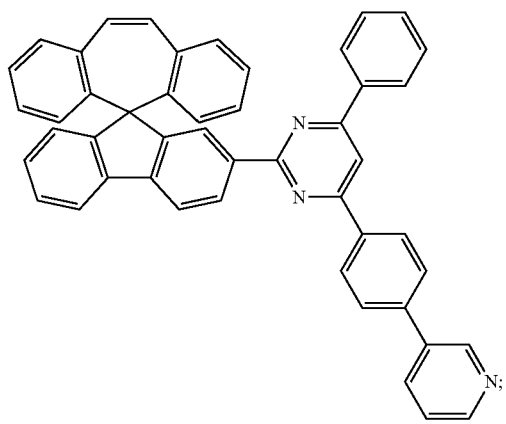

Compound 11
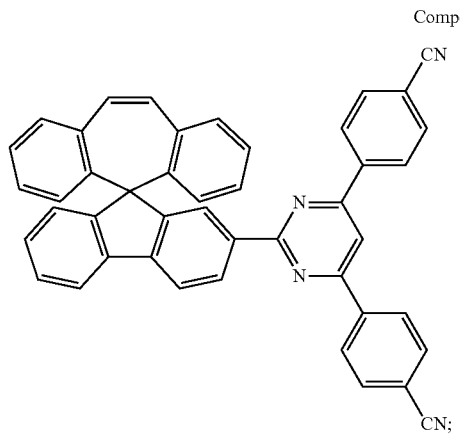
Compound 12
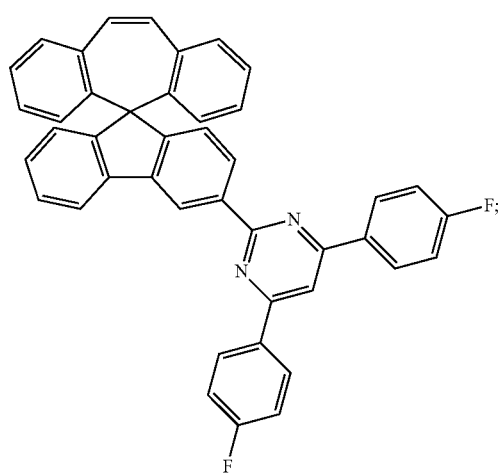
Compound 13
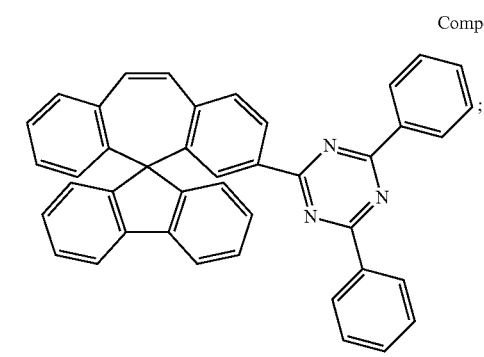
Compound 14
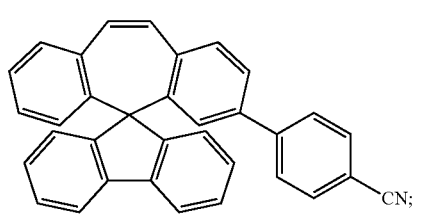
Compound 15
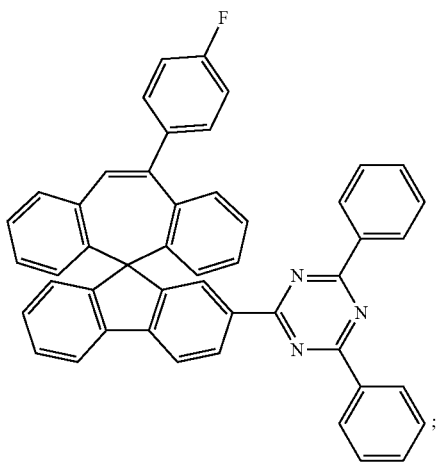
Compound 16
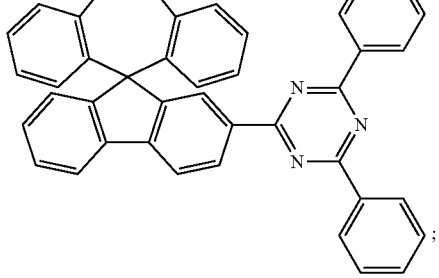
Compound 17
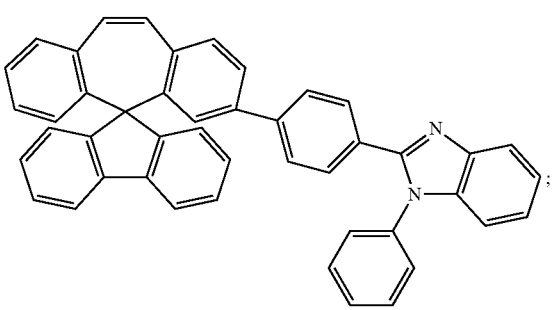
Compound 18
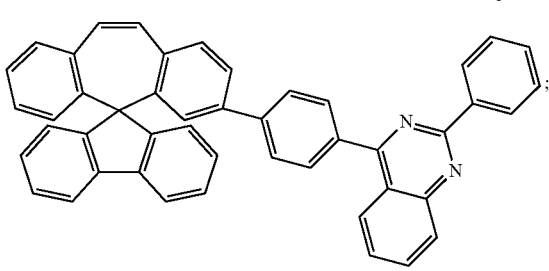

Compound 19
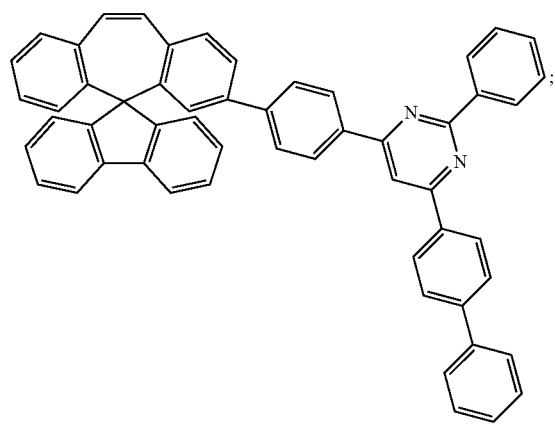
Compound 20
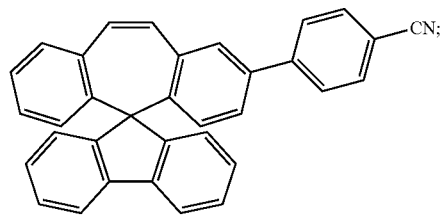
Compound 21
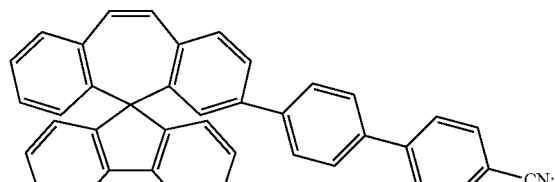
Compound 22
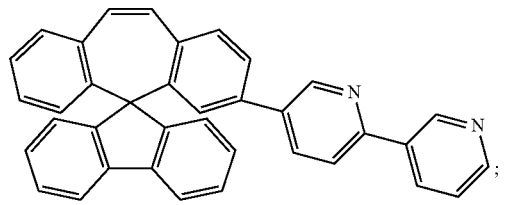
Compound 23
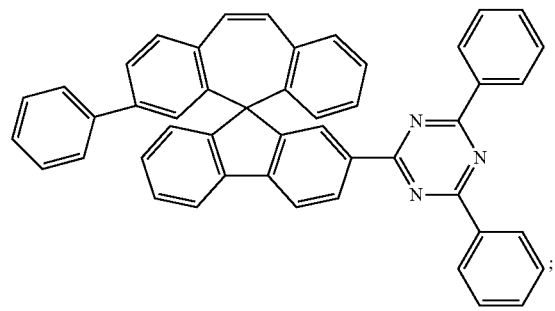
Compound 24
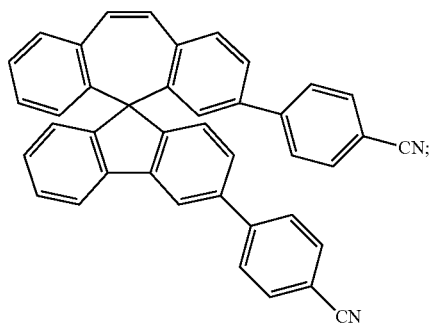
Compound 25
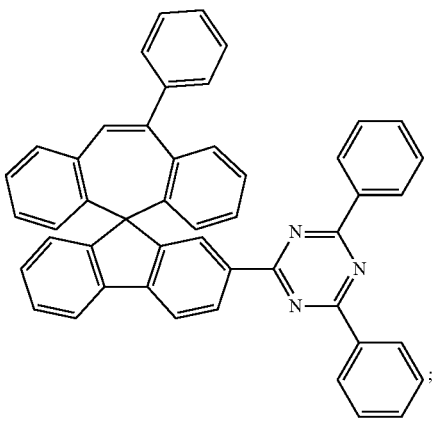
Compound 26
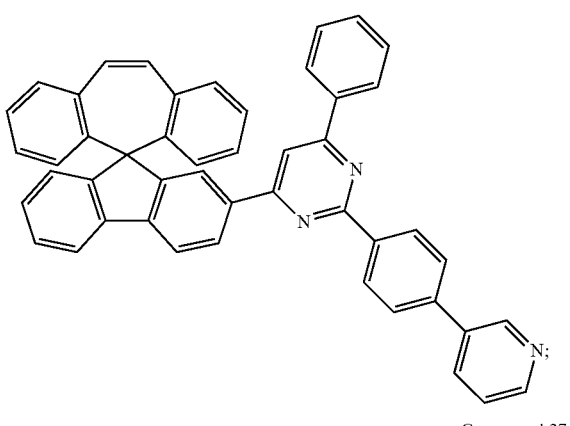
Compound 27
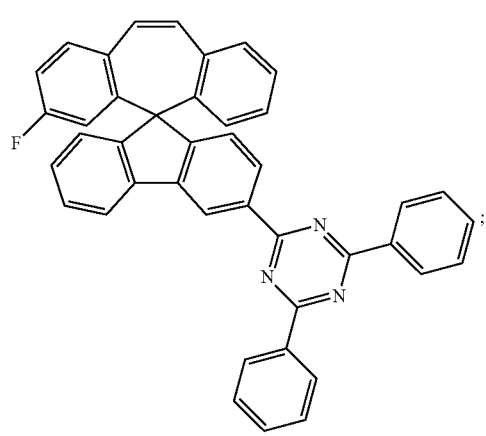

Compound 28

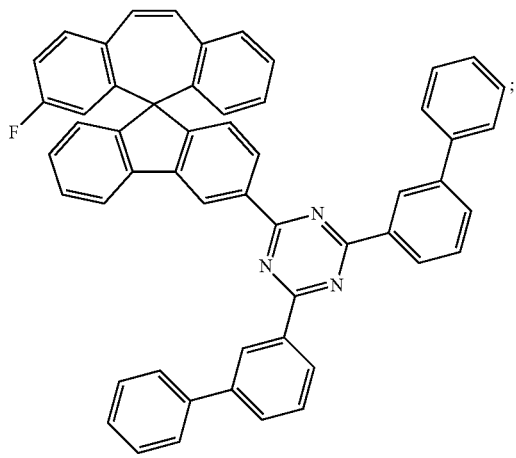

Compound 29

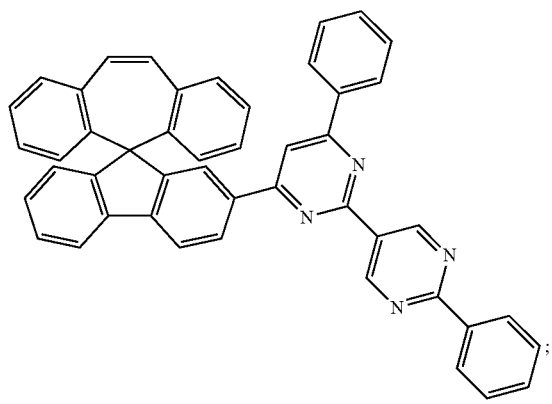

Compound 30

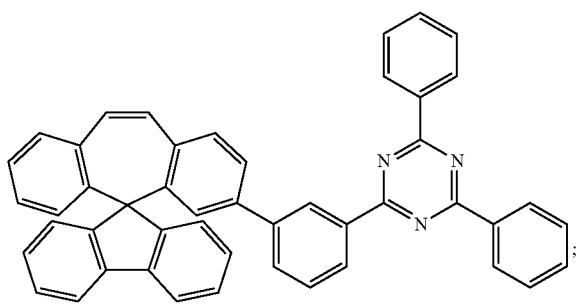

Compound 31

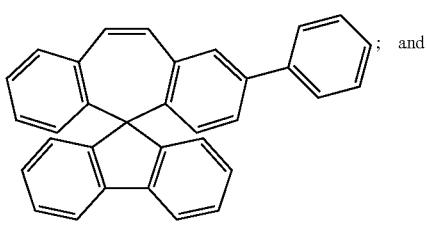; and

Compound 32

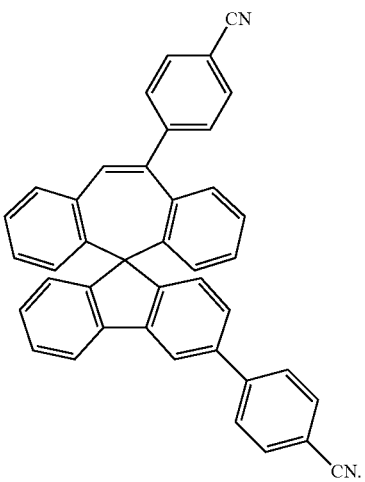

10. An organic electronic device, comprising a first electrode, a second electrode, and an organic layer disposed between the first electrode and the second electrode, wherein the organic layer comprises the compound as claimed in claim 1.

11. The organic electronic device as claimed in claim 10, wherein the organic electronic device is an organic light emitting device.

12. The organic electronic device as claimed in claim 11, wherein the organic light emitting device comprises:
    a hole injection layer formed on the first electrode;
    a hole transport layer formed on the hole injection layer;
    an emission layer formed on the hole transport layer;
    an electron transport layer formed on the emission layer, wherein the organic layer is the electron transport layer; and
    an electron injection layer formed between the electron transport layer and the second electrode.

13. The organic electronic device as claimed in claim 11, wherein the organic light emitting device comprises:
    a hole injection layer formed on the first electrode;
    a hole transport layer formed on the hole injection layer;
    an emission layer formed on the hole transport layer;
    a hole blocking layer formed on the emission layer, wherein the organic layer is the hole blocking layer;
    an electron transport layer formed on the hole blocking layer; and
    an electron injection layer formed between the electron transport layer and the second electrode.

14. The organic electronic device as claimed in claim 10, wherein the compound is selected from the group consisting of:

Compound 1
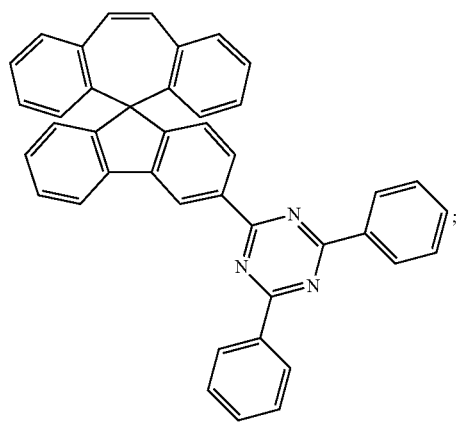
Compound 2
Compound 3
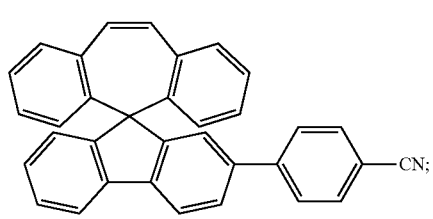
Compound 4
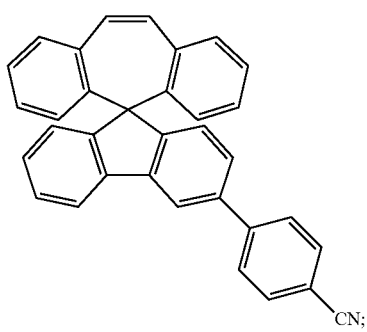
-continued
Compound 5
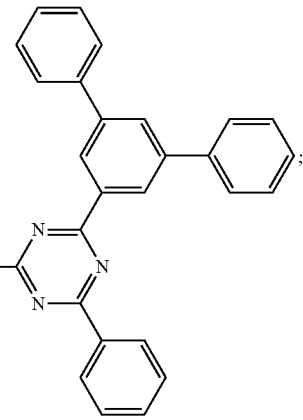
Compound 6
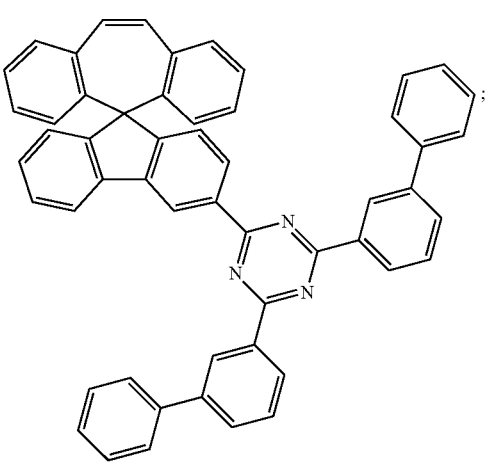
Compound 7
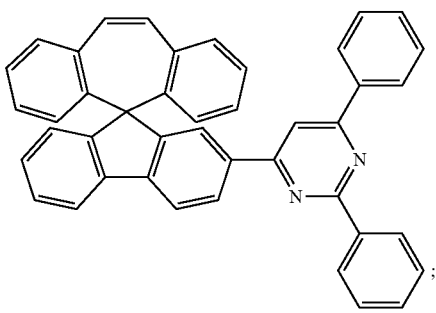

Compound 8
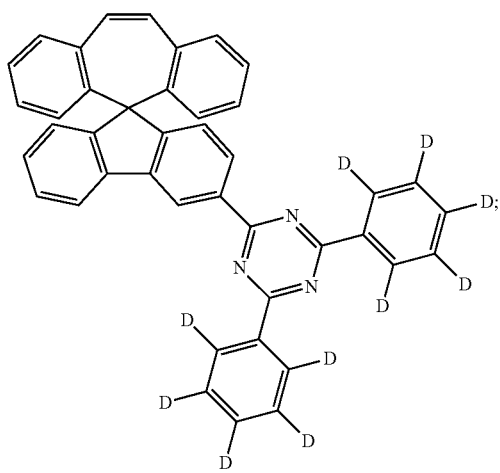
Compound 9
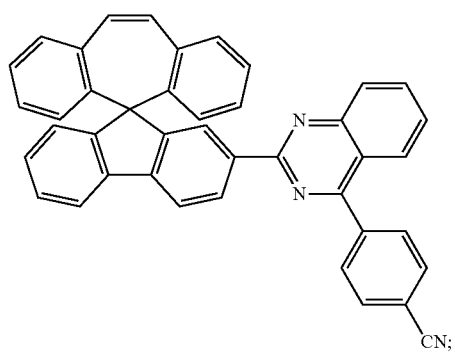
Compound 10
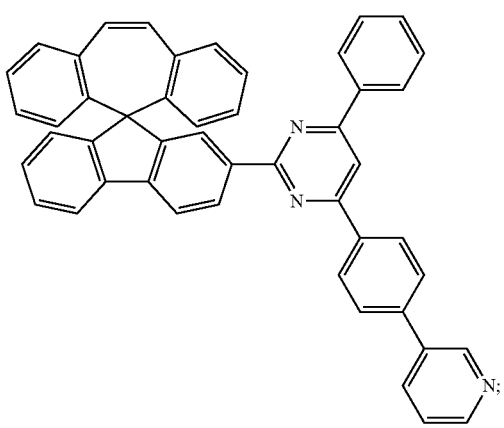
Compound 11
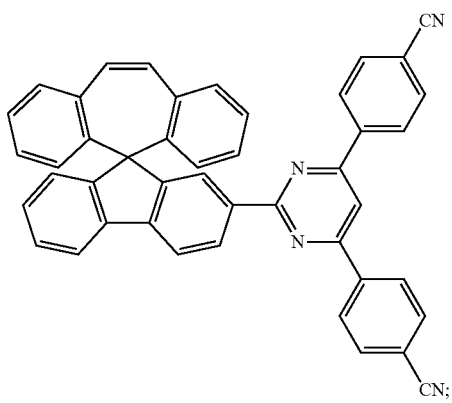
Compound 12
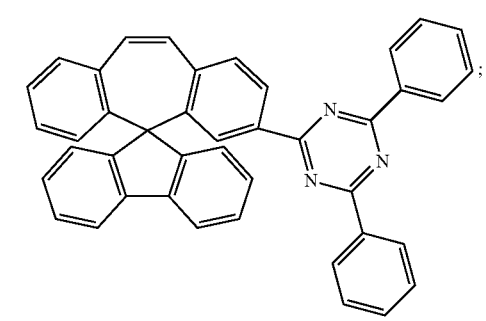
Compound 13
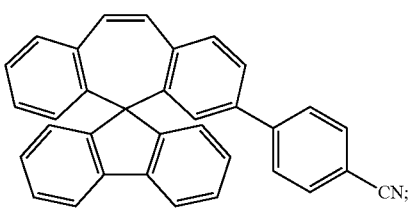
Compound 14

-continued
Compound 15
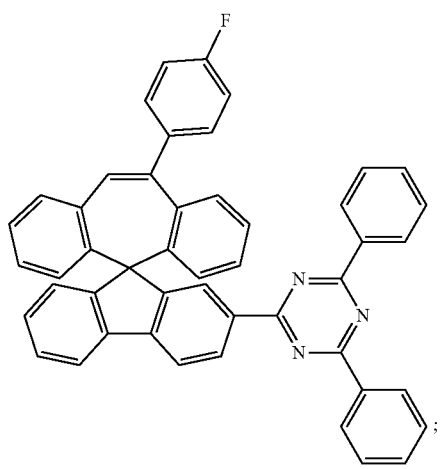
Compound 16
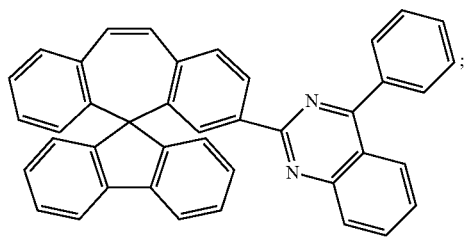
Compound 17
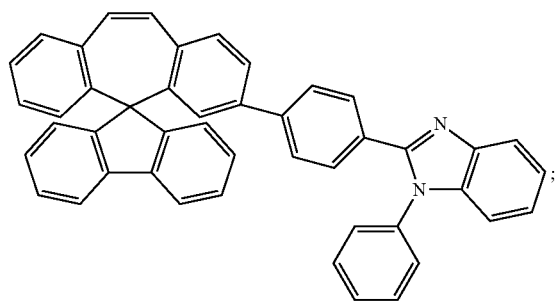
Compound 18
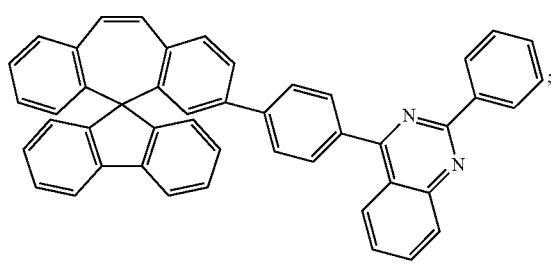
Compound 19
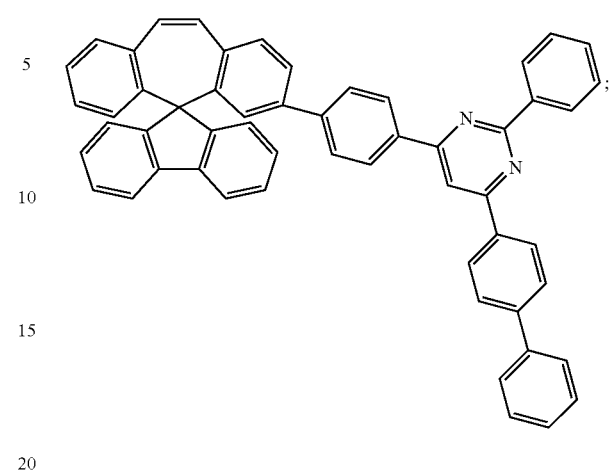
Compound 20
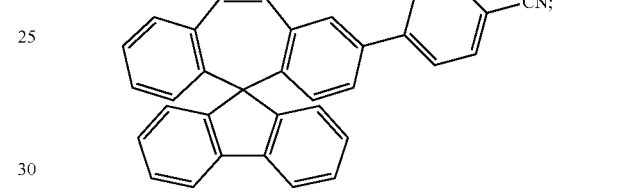
Compound 21
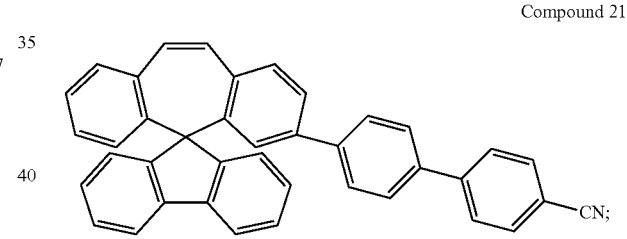
Compound 22
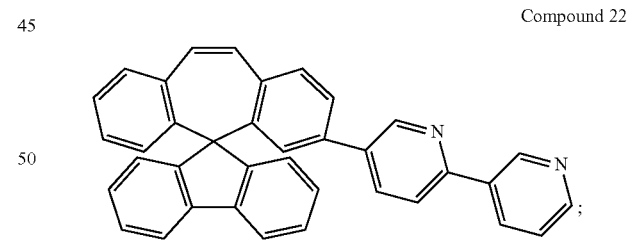
Compound 23
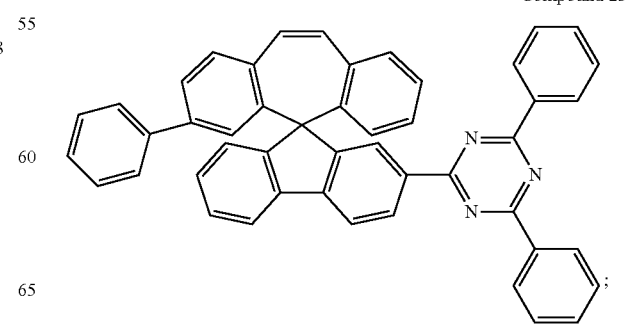

Compound 24
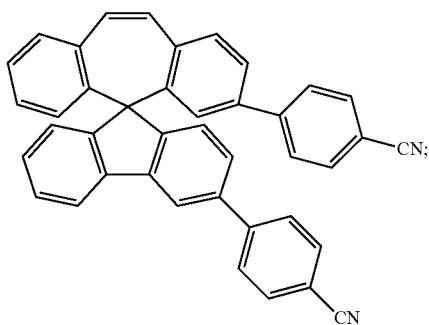
Compound 25
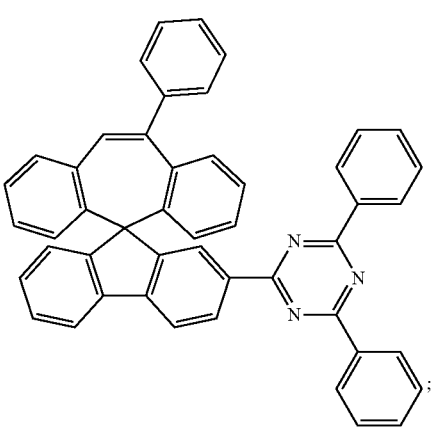
Compound 26
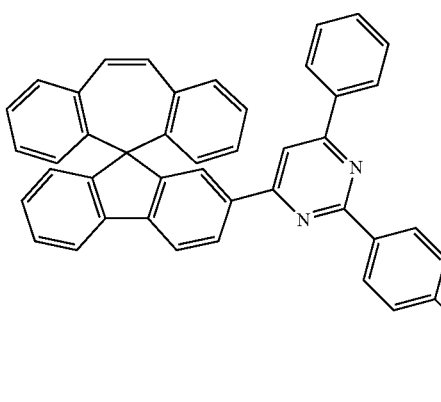
Compound 27
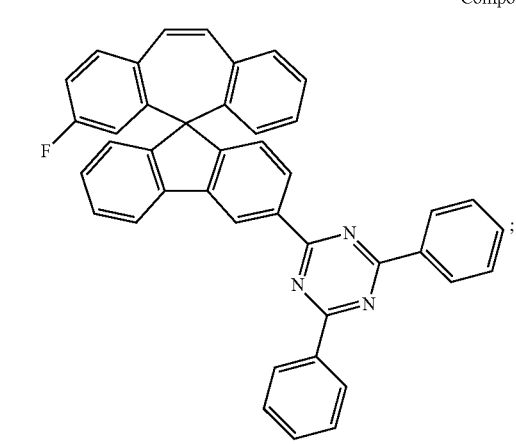
Compound 28
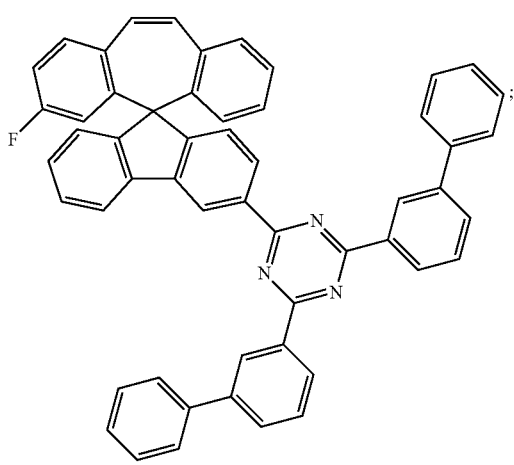
Compound 29
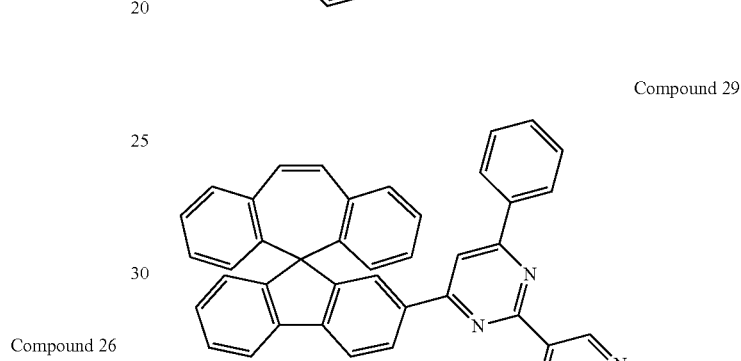
Compound 30
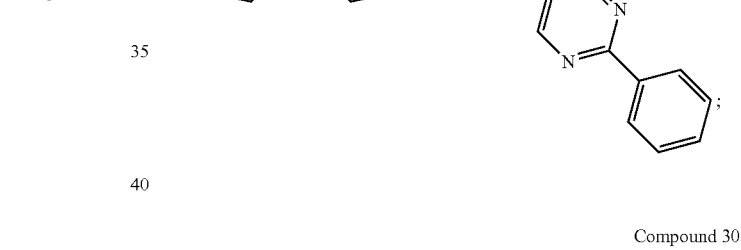
Compound 31
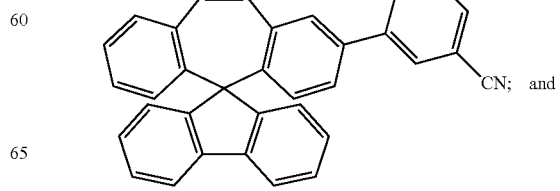

-continued
Compound 32
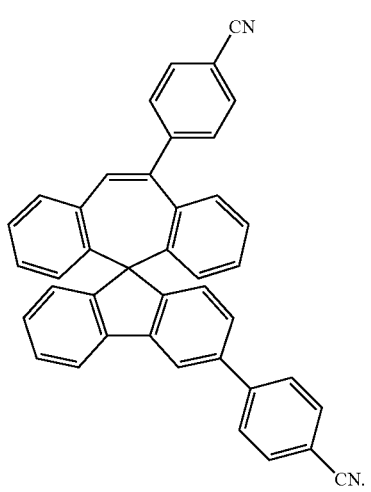
* * * * *